United States Patent [19]
Stevens et al.

[11] Patent Number: 5,340,739
[45] Date of Patent: Aug. 23, 1994

[54] HEMATOPOIETIC CELL SPECIFIC TRANSCRIPTIONAL REGULATORY ELEMENTS OF SERGLYCIN AND USES THEREOF

[75] Inventors: Richard L. Stevens, Sudbury; Shalom Avraham, Brighton, both of Mass.

[73] Assignee: Brigham & Women's Hospital, Boston, Mass.

[21] Appl. No.: 906,871

[22] Filed: Jul. 2, 1992

Related U.S. Application Data

[63] Continuation-in-part of Ser. No. 816,289, Jan. 3, 1992, abandoned, which is a continuation-in-part of Ser. No. 635,544, Jan. 18, 1991, Pat. No. 5,171,674, filed as PCT/US89/03051, Jul. 13, 1989 which is a continuation-in-part of Ser. No. 224,035, Jul. 13, 1988, abandoned.

[51] Int. Cl.$^5$ .......................... C12N 5/10; C12N 5/16; C12N 1/00; C12N 15/63
[52] U.S. Cl. .............................. 435/240.1; 435/240.2; 435/252.3; 435/320.1; 435/172.3; 536/24.1; 935/34; 935/36; 935/71
[58] Field of Search ............ 536/24.1; 435/69.1, 69.6; 435/172.3, 252.3, 240.2, 240.1, 320.1; 935/34, 36, 71

[56] References Cited

U.S. PATENT DOCUMENTS

| | | | |
|---|---|---|---|
| 4,663,281 | 5/1987 | Gillies et al. | 435/69.1 |
| 4,912,040 | 3/1990 | Kaufman et al. | 435/69.6 |
| 5,171,674 | 12/1992 | Stevens et al. | 435/69.1 |

FOREIGN PATENT DOCUMENTS

WO90/00606 1/1990 World Int. Prop. O.

OTHER PUBLICATIONS

Ornitz et al (1987) Mol. Cell. Biol. 7 3466–3472.
Schaeffer et al (1989) J. Biol Chem. 264: 7153–7160.
Toyama et al (1990) Febs Lett. 268 217–221.
Kuhl et al (1987) Cell 50 1057–1067.
Chang, L.-J. et al., "Gene Expression from Both Intronless and Intron–Containing Rous Sarcoma Virus Clones Is Specifically Inhibited by Anti–Sense RNA," Mol. and Cell. Biol. 5(9):2341–2348.
McKnight, S. et al., "Transcriptional Selectivity of Viral Genes in Mammalian Cells," Cell 46: 795–805 (1986).
Wingender, E., "Compilation of transcription regulating proteins,"0 Nucl. Acids Res. 16:1879–1902 (1988).
Johnson, P. F. et al., "Eukaryotic Transcriptional Regulatory Proteins," Annu. Rev. Biochem. 58: 799–839 (1989).
Angerth, T. et al., "Cloning and structural analysis of a gene encoding a mouse mastocytoma proteoglycan core protein; analysis of its evolutionary relation to three cross hybridizing regions in the mouse genome," Gene 93:235–240 (1990).
Tantravahi, R. V. et al., Proc. Natl. Acad. Sci. USA, 83:9207–9210 (1986).
Giacoletto, K. S. et al., J. Exp. Med., 164:1422–1439 (1986).
Bourdon, M. A. et al., Proc. Natl. Acad. Sci. USA, 82:1321–1325 (1985).
Stevens, R. L. et al., The Journal of Biological Chemistry, 260:14194–14200 (1985).

(List continued on next page.)

Primary Examiner—Robert A. Wax
Assistant Examiner—G. E. Bugaisky
Attorney, Agent, or Firm—Sterne, Kessler, Goldstein & Fox

[57] ABSTRACT

A negative transcription regulatory element (a constitutive suppressor) between residues −250 and −190 of the 5' flanking region of the mouse serglycin gene, a positive (hematopoietic cell enhancer) regulatory element located between residues −118 and −81, an equivalent of the TATA- box and a novel eukaryotic promoter that utilizes such equivalent, vectors containing such elements and hosts transformed therewith, are described. These regulatory elements, vectors and hosts are useful in gene transcription of heterologous genes in eukaryotic cells, and especially in hematopoietic cells. In addition, transcriptional factors that bind to these elements are described.

28 Claims, 25 Drawing Sheets

OTHER PUBLICATIONS

Avrahamn, S. et al., *Proc. Natl. Acad. Sci. USA*, 86:3763–3767 (1989).

Bourdon, M. A. et al., *Molecular and Celular Biology*, 7:33–40 (1987).

Luikart, S. D. et al., *Chemical Abstracts*, 103:647 Abstract No. 212337K (1985).

Tantravahi, R. V. et al., *Fed. Proc.*, 45:626 Abstract No. 2740 (1986).

Hassell, J. R. et al., *Ann. Rev. Biochem.* 55:539–567 (1986).

Krusius, T. et al., *Proc. Natl. Acad. Sci. USA* 83:7683–7687 (1986).

T. F. Bumol and R. A. Reisfeld, *Proc. Natl. Acad. Sci. USA* 79:1245–49 (1982).

Rettig, J. et al. *Science* 231: 1281–1884 (1986).

Stevens, R. L., "Intracellular Proteoglycans in Cells of the Immune System," in *Biology of Proteoglycans*, Academic Press, Inc. (1987) pp. 367–385.

Razin, E. et al., *J. Biol. Chem.* 257(12):7229–7236 (1982).

Levi-Schaeffer, F. et al., Proc. Natl. Acad. Sci. USA 83:6485–6488 (1986).

Stevens, R. L. et al., *J. Immunol.* 133(5):2674–2680 (1984).

Bourdon, M. A. et al., "Identification form cDNA of The Precursor Form of A Chondroitin Sulfate Proteoglycan Core Protein," *J. Biol. Chem.* 261:12534–12537 (1986).

Berger, S. L. et al. (ed), *Methods In Enzymology* 152:Academic Press (1987).

Stevens, R. L. et al., *J. Biol. Chem.* 263:7287–7291 (1988).

Alliel, P. M. et al., *FEBS Lett.* 236:123–126 (1988).

Perkins, A. S. et al., *Mol. Cel. Biol.* 3:1123–1132 (1983).

Avraham, S. et al., *J. Biol. Chem.* 264:16719–16726 (1989).

Humphries, D. E. et al., *J. Biol. Chem.* 267:13558–13563 (1992).

Avraham, S. et al., *J. Biol. Chem.* 267:610–617 (1992).

Ghildyal, N. et al., *J. Biol. Chem.* 267:8472–8477 (1992).

Nicodemus, C. F. et al., *J. Biol. Chem.* 265:5889–5896 (1990).

```
  1  GTGCAGCTGGGAGAGCTAGACTAAGTTGGTC ATG ATG CAG AAG CTA CTC AAA TGC
                              ***    M   M   Q   K   L   L   K   C     8

56  AGT CGG CTT GTC CTG GCT CTT GCC CTC ATC CTG GTT CTG GAA TCC TCA
      S   R   L   V   L   A   L   A   L   I   L   V   L   E   S   S   24
                  ↓

104  GTT CAA GGT TAT CCT ACG CAG AGA GCC AGG TAC CAA TGG GTG CGC TGC
      V   Q   G   Y   P   T   Q   R   A   R   Y   Q   W   V   R   C   40

152  AAT CCA GAC AGT AAT TCT GCA AAC TGC CTT GAA GAA AAA GGA CCA ATG
      N   P   D   S   N   S   A   N   C   L   E   E   K   G   P   M   56

XmnI
200  TTC GAA CTA CTT CCA GGT GAA TCC AAC AAG ATC CCC CGT CTG AGG ACT
      F   E   L   L   P   G   E   S   N   K   I   P   R   L   R   T   72

248  GAC CTT TTT CCA AAG ACG AGA ATC CAG GAC TTG AAT CGT ATC TTC CCA
      D   L   F   P   K   T   R   I   Q   D   L   N   R   I   F   P   88

296  CTT TCT GAG GAC TAC TCT GGA TCA GGC TTC GGC TCC GGC TCC GGC TCT
      L   S   E   D   Y   S   G   S   G   F   G   S   G   S   G   S  104

344  GGA TCA GGA TCT GGG AGT GGC TTC CTA ACG GAA ATG GAA CAG GAT TAC
      G   S   G   S   G   S   G   F   L   T   E   M   E   Q   D   Y  120

AccI
392  CAA CTA GTA GAC GAA AGT GAT GCT TTC CAT GAC AAC CTT AGG TCT CTT
      Q   L   V   D   E   S   D   A   F   H   D   N   L   R   S   L  136

440  GAC AGG AAT CTG CCC TCA GAC AGC CAG GAC TTG GGT CAA CAT GGA TTA
      D   R   N   L   P   S   D   S   Q   D   L   G   Q   H   G   L  152

488  GAA GAG GAT TTT ATG TTA TAA AAGAGGATTTTCCCACCTTGACACCAGGCAATGTA
      E   E   D   F   M   L  ***                                     158

544  GTTAGCATATTTTATGTACCATGGTTATATGATTAATCTTGGGACAAAGAATTTTATAGAAAT
607  TTTTAAACATCTGAAAAAGAAGCTTAAGTTTTATCATCCTTTTTTTT(T)CTCAT
```

FIG.2

```
  -621                            GCCACTGCTCTCCAGCCTGGGTGACAGAGTGAGACTCCATCTCAAAAAAAAAAAAAAAAAAAAA
  -557 AAAAAGAAGAAAAAGAAGAAGAAGAAGAAACTGTTCATCTGAAATCCGACAACTCATTCTTGAAGGTTAGAGCTCAGC
  -479 TTTGAAGTTTCACTTCACGAGCTTGGCTCAGTGAGGTATGTTACTCCCGGTGAAAAAGAAAATGAAGAGAATGTTTT
  -401 ATGTTGAAAGTGCTTGGTGACGAAAAGGCAGCACCTAGATCCCTTATCTCATAAAAAATGCAGCAGATTCTTAATATT
  -323 AGCAATCTAGTATTTAGATTGTTACCTGAAGAAAGGAAAAACAAACTGTCCCAAATGCTGATTCTACTGTTTCGGTGG
  -246 GAAAAAAAAATGTCTTGCAGGCAAGTGGCAAACAACAAAACTTTTGAAAAAGCAGGCCTGGGGGGAGTCCAGTACAGT
  -168 TTCATAATGGGTATGAATAGTTATTTTACTGTGTTCCCCCCACCCCCTTTCTTTCTGGGTTTTGATGTGGATGTCTTT
   -89 CTATTTGTTCAGGAAATTGTGACGTGTGTTCTGGGCAGGGTTTGAGGTTTTGGAACATTTTCTAAAAGGGACAGAGAG
                         ┌──exon 1
   -11 CACCCTGCTACATTTCCTAATCAAGAAGTTGGCGTGCAGCTGGGAGAGCTAGACTAAGTTGGTC
```

|     |     |     |     |     |     |     |     |     |     |     |     |     |     | start |     |
|-----|-----|-----|-----|-----|-----|-----|-----|-----|-----|-----|-----|-----|-----|-------|-----|
|     |     |     |     |     |     |     |     |     |     |     |     |     |     | ATG   | ATG |
|     |     |     |     |     |     |     |     |     |     |     |     |     |     | Met   | Met |
|     |     |     |     |     |     |     |     |     |     |     |     |     |     | 1     |     |
| CAG | AAG | CTA | CTC | AAA | TGC | AGT | CGG | CTT | GTC | CTG | GCT | CTT | GCC | CTC   | ATC |
| Gln | Lys | Leu | Leu | Lys | Cys | Ser | Arg | Leu | Val | Leu | Ala | Leu | Ala | Leu   | Ile |
|     |     |     |     |     |     |     | 10  |     |     |     |     |     |     |       |     |

```
                                          exon 1──┤
CTG GTT CTG GAA TCC TCA GTT CAA Ggt aagactcaggagtcttgttccccagccatcttc
Leu Val Leu Glu Ser Ser Val Gln (Gly)
             20
                                          ┌──exon 2
-( 8 kb)-tacttagtaacaatgtgggttcctcgggca gGT TAT CCT ACG CAG AGA GCC AGG
                                        (Gly) Try Pro Thr Gln Arg Ala Arg
                                                          30

TAC CAA TGG GTG CGC TGC AAT CCA GAC AGT AAT TCT GCA AAC TGC CTT
Tyr Gln Trp Val Arg Cys Asn Pro Asp Ser Asn Ser Ala Asn Cys Leu
                        40

GAA GAA AAA GGA CCA ATG TTC GAA CTA CTT CCA GGT GAA TCC AAC AAG
Glu Glu Lys Gly Pro Met Phe Glu Leu Leu Pro Gly Glu Ser Asn Lys
                                60
```

FIG.4A

```
                                                    exon 2
ATC  CCC  CGT  CTG  AGG  ACT  GAC  CTT  TTT  CCg taagtggacttttctctaattaattaatt
Ile  Pro  Arg  Leu  Arg  Thr  Asp  Leu  Phe  (Pro)
                    70 exon 3
-(-6 kb)-tccactggttttttttcccattttttctttcatacttc agA AAG  ACG  AGA  ATC  CAG  GAC
                                               (Pro) Lys  Thr  Arg  Ile  Gln  Asp
                                                                        80

TTG  AAT  CGT  ATC  TTC  CCA  CTT  TCT  GAG  GAC  TAC  TCT  GGA  TCA  GGC  TTT
Leu  Asn  Arg  Ile  Phe  Pro  Leu  Ser  Glu  Asp  Try  Ser  Gly  Ser  Gly  Phe
                              90

GGC  TCC  GGC  TCC  GGC  TCT  GGA  TCA  GGA  TCT  GGG  AGT  GGC  TTT  CTA  ACG
Gly  Ser  Gly  Ser  Gly  Ser  Gly  Ser  Gly  Ser  Gly  Ser  Gly  Phe  Leu  Thr
               100                                           110

GAA  ATG  GAA  CAG  GAT  TAC  CAA  CTA  GTA  GAC  GAA  AGT  GAT  GCT  TTC  CAT
Glu  Met  Glu  Gln  Asp  Try  Gln  Leu  Val  Asp  Glu  Ser  Asp  Ala  Phe  His
                              120                                           130

GAC  AAC  CTT  AGG  TCT  CTT  GAC  AGG  AAT  CTG  CCC  TCA  GAC  AGC  CAG  GAC
Asp  Asn  Leu  Arg  Ser  Leu  Asp  Arg  Asn  Leu  Pro  Ser  Asp  Ser  Gln  Asp
                                             140

TTG  GGT  CAA  CAT  GGA  TTA  GAA  GAG  GAT  TTT  ATG  TTA  TAA  AAGAGGATTTTC
Leu  Gly  Gln  His  Gly  Leu  Glu  Glu  Asp  Phe  Met  Leu  stop
                    150                                      160

CCACCTTGACACCAGGCAATGTAGTTAGCATATTTTATGTACCATGGTTATATGATTAATCTTGGGACAAAGAATTTT
ATAGAAATTTTTAAACATCTGAAAAAGAAGCTTAAGTTTTATCATCCTTTTTTTTCTCATGAATTCTTAAAGGATTAT
GCTTTAATGCTGTTATCTATCTTATTGTTCTTGAAAATACCTGCATTTTTTGGTATCATGTTCAACCAACATCATTAT
GAAATTAATTAGATTCCCATGGCCATAAAATGGCTTTAAAGAATATATATATATTTTTAAAGTAGCTTGAGAAGCAAA
TTGGCAGGTAATATTTCATACCTAAATTAAGACTCTGACTTGGATTGTGAATTATAATGATATGCCCCTTTTCTTATA
AAAACAAAAAAAAAAATAAT
```

FIG.4A(cont.)

```
                                    GCCACTGCTCTCCAGCCTGGGTGACAGAGTGAGACTC
-584  CATCTCAAAAAAAAAAAAAAAAAAAAAAAAAAGAAGAAAAAGAAGAAGAAGAAGAAACTG
      TTCATCTGAAATCCGACAACTCATTCTTGAAGGTTAGAGCTCAGCTTTGAAGTTTCACTT
      CACGAGCTTGGCTCAGTGAGGTATGTTACTCCCCGGTGAAAAAGAAAATGAAGAGAATGT
-404  TTTATGTTGAAAGTGCTTGGTGACGAAAAGGCAGCACCTAGATCCCTTATCTCATAAAAA
      ATGCAGCAGATTCTTAATATTAGCAATGTAGTATTTAGATTGTTACCTGAAGAAAGGAAA
      AACAAACTGTCCCAAATGCTGATTCTACTGTTTCGGTGGGAAAAAAAAATGTCTTGCAGG
-224  CAAGTGGCAAACAACAAAACTTTTGAAAAAGCAGGCCTGGGGGAGTCCAGTACAGTTTC
      ATAATGGGTATGAATAGTTATTTTACTGTGTTCCCCCCACCCCCTTTCTTTCTGGGTTTT
      GATGTGGATGTCTTTCTATTTGTTCAGGAAATTGTGACGTGTGTTCTGGGCAGGGTTTGA
-44   GGTTTTGGAACATTTTCTAAAAGGGACAGAGAGCACCCTGCTAC
```

```
                                                      1
                                          ATTTCCTAATCAAGAA
        GTTGGCGTGCAGCTGGGAGAGCTAGACTAAGTTGGTCATGATGCAGAAGCTACTCAAATG   EXON 1
        CAGTCGGCTTGTCCTGGCTCTTGCCCTCATCCTGGTTCTGGAATCCTCAGTTCAAG
```

```
                                                                GTAA
137   GACTCAGGAGTCTTGTTCCCCAGCCATCTTCTCTGTAAGCCCTGTGGTCCATGCAAGTCA
      TTATATTCATTTTAAGGCATAGAATGTATAATATTGTGAGAAAGGAGGCAAAGAAGAAGG
      ATTTGGGGTCGCTGAACCCTTTAATATGAGTTCTGTTAAGTTTGGTACCAAGAAAAATTA
317   AACTCTGTGGCGTGTGCAGTCTTGTAAACTCTTACAATGATTGAAATGTGCTATTTTGGG
      ATGAAAATGTGAGGTTTATAAATTTTAAAAGCTCAAAAAAGGAATCTAGAAAATGACTCC
      TGTGCCTGTTGCATGGAGGAGATGGCACCTTTGACTGTTGGGGGGTGTCTGCCTACCCCT
497   AAGTGTCTACATCAGCCCCAAGTTTTAGTGCGCTGTGACGGTGTCATTGTTATTTTAACA
      CTGGGAGACGTTATATTCCAATTGGGGTGAATCTGACTGTGTGTATTTTCTTTTCTTTTT
      TTTTTTTTAAAGATAAACTTGGTTCTTACTGAAAACTCAATTATGGTTAGACATAGTTC
677   ATGTAAAACCTCTCAGATTTTAAAGAGAAGGCCAAATAATTTGGTATTTGTGCTCTTGCT
      CAGAGAAGCATCATATTCGGAAATATCTTCCTAGGTTTATCTACCATTTAGTGTTGTTTA
      GTCAGACTGAAACAACTTAAAACCTGTAATGACTAAGACAATGAAAATGATAGGCTTGTA
857   AGAAAAATACAATTTGTTATTCTTTGGCAAATAAGGAATCATGTCTAAATAAGACGGAGG
      TCATGGCTTGATAGAGAGATGGCTGAACCTATAGTAGAAAAACACTAGGTTCCGCCAAAT
      GGTAAGGGAAATGTTGAGTCACAATGACACACATGTCCTAGATTTGTTTCGTCAAAGCGA
```

FIG.4B 1,037 CTTTTGGTTGTCATGATCTTACTTCCGGTGGAGATGAAATCTTACAGATGATCGCAGAGA
CATTCATTTTATGTTGGAAATTTATAAAATCATTTTCTTCTAGTTATGCTAATGCTGAAA
AAAGAGCAAGTAATGTTTCTGGAACGTTATTAATTTATGTATTTTTAAAATATAAAACAT
1,217 TGTCAATTGTAGGGAACAGGCTTCACTGGGATCTTTTAGGGAATATCTTCAGCTTGATGA
AATAATTCCCGAATAGCCAAGTGGTCTGACAAGATCGAGAGTAATGAGGCCCATACTTTA
GTACAGTCTTGAATGGCCAGATGGTGCTGGGCATACCCCAACCAGAGATATGTAAGTCTT
1,397 TATGTTGTCAAAATTTCCCAGAAACATGAATTTCCCACTAAGATTCATTAAGGAAAACTA
GAATGAAAACAAAAACGTTCCTTGTATAATATTCATTAGAAAGAAATGAAGAAGGCCGGG
CATGGTGGCTCACGCCTGTAATCCCAGCACTTTGAGAGGCCAAGGTAGGCAGATCATGAG
1,577 GTCAGGAGTTTGAGACCAGCCTGGCCAACATAGTGAAATCCCGTCTCTACCAAAAATACA
AAAAAATTAGCCGGGCATGGTGGCACACACCTGTCATCCCAGCTACTCAGGAGGCTGAGG
CAGGAGAATTGCTTGAACCTGGGAGGTGGAGGTTGCAGTGAGCTGAGATTGCACCACTGT
1,757 ACTACAGCCTAGGTGACAGTGCAAGACTCTGTCAGAAAGAAAGAAAGAGAGAGAGAGAGA
AAGAAAGGAAAGAAAGAAAGAGAAGGAAAGAAAATAATTCATCATGAAATTGTATAGAAT
ACTAGCATTTATGTCATGACCTCGTAGGTTTAGCTCTTTGTTAGAAAAGGAAACCATAGA
1,937 AAGAGACAAGGGAGAAACTGACAAACTAGGGTGTTTCCGAAAAAAGGCTCTCAGTATCGG
GCTCAAGGGCTTGTGCCCACATCTGAGCATGCAGGGAAATAGATGTCCCCCACTGGCTGC
ACATGTGAGTGACTGCGGCACAAGGCTGTGATGTGAAGAGTCATGACACCATTTCCTCAC
2,117 ACCTCCACGCAATGCCAGATATGATTCGACAACATTCTTCCTGTCTTATAAAAGTGTTTA
TCTAGCCCGTTGGTTTGGCAGATGAAATCAACTAGGCTTTTGGCTTGCTTTTACTGAGCA
TATTCAAAACCATTTCAGGTCACTATAGTGGTTTGCTCGGGTTGCCATAACAAAGTACCA
2,297 CGGACTGAGTGGCTTAAATAACAGAAATGTATTTCCTGACAGTTCTGGAGATGGGAGTCC
AAGATCAAGGTGCTGGCAGGGTCGATCGCATTCTGAGGCCTCTCTCCTTGGCTTATAGAT
GGCGCCTTCTCCCTTGTCTGCACATGGCCTTTCCTCCATGCATCCGTGTCTTAATACCAT
2,477 CTTCTTAGAGGGTCACCAGGCATTGGATCAGGGCCACCCTAATGGCCTCATCTTAACTAC
CTATATCTGCAATGACCCTATTTCTGAACAATTTCACATTGTGAGATTCTGTGGGTTAGA
ACTGGAACATATGAATTTGGTGGTGGTATATTTTTATTATAAGTCAAACCCAAGTAAAGA
2,657 TGTGGGGTAAGATTGTGTTTACCAAGCACAAAGAAATGGAAATTTGGGGATGTGTAACTC
TGGAGAGCACAGATGACTAATCTATTTAATGTAGGGCTCCAGGGGATTTGATGAGGCCTG
TGAATCTTCCACTTTTATTGCCTCTCTTTTCCAATGACACCCATAAAGAAAAAAATGGA
2,837 ATATCCATGAACAGGTGCAGCCAAGGAGGCCAGGCCCGCCATGTGTCCACTGTATACTGT
CTCCTAGCTCACAGGAATGATACTGATCCACTCCTTGTGCTGCTCTTTGTAAAGTGATTT
CACATCCATTCTCTGGTAATCATCATCACATTCCCTGTGATGAGGAATTAGCACCAATTA

FIG.4C 3,017 TAGAGGAGAAAACTGGATCTGACATTTCTCATCTCATTTGCTCTATACATTAACCTCTTG
CAAAAAATTTGTGAGTCTTGCCCAAGACCCATTACAACTAATTAACGGCTGAACTGGTCG
TCTGATTTCAAGGCCAGAATTAACTTTCTACTGCAGCTCATGGATCAGAGGTTTTCTTTA
3,197 TTTAAACAAACAAACAAAAAATCCTTTGACCGTAGCCCTTGCTATAACATTTCCCACTGA
GTTGAGGGAGAAATTGAAAGTAAACTTAGGAGCTTTTTATAGCTTGTCAAACCATGCAAG
AGTGGGGAAGCTTATCCATCTTGTGGAATTGATAGACCAGGAGGAAGTAACTCCGGCTT
3,377 AGATAATGCTACCATTTTGAATAAATCAAATGGTCTTCTTTTCCCCTTCATGGTAGTTGC
TGCTTAAGTTTCTCTAACATGCCTGCAGTAAGTTTCCATTAAGAATAGGAAATTAGGCTC
GGTACAGTGGCTCACGTCTGTAGTCTTAGCACTTTGGGAGACCGAGGAGTGTGGATCACT
3,557 TGAGGTCAGGAGTTCAAGACCAGCCTGGCCAACATGGTGAAACCCCATCTCTACTAAAA
ATACAAAAATTAGCCAGGCATAGTGGCATGCACCTGTAATCCCAGCTACTCGAGAGGCTG
AGGCAGGAGAATCACTTGAACCAGGGAGATGGAGGTTGCAGTGAGCCAAGATCATGCCAC
3,737 TGCACTCCAGCCTGGGCGATAGACTGAGACTCTGTCTCAAAAAAAAAAAAAAAAAAAAGA
AAAAAGAAAAGAAAAAAAAAAGAAATTAGTATATTGTGATTATGTTGAGGGAAAAGTTAG
TACCATAATATAAAAAGGTATGGACTATTGGAGAAAGTTGTTTGCTTTGGTAACATTTAC
3,917 TCATAGAAAGTATTTTGGTAAAGCAGGACTCAGGGTGGTGGGGGAGGTGGGCAGTGAGGG
ATAGGATTCAAATAAAAACCATTCTTTCCCTTGGAATCCACTACACAATTAACCAACAAA
TCCCATAAGTGGACCTTTTAGGAAGATAACATTTCTATCCATGAGCATAGCCACTATAAT
4,097 CACAAGACATTTATCTCAAGCAAGATAGAGTCAAGATACTCTCACAACCTCAGGGGCTGG
AACTGTAAATTTTCACATCCTGCCAACACCCTTGAATAGCTATGTCAAGAATTTAGTGTC
TGTAACTTGTTCTTTATTTTAAAGTACATTTAACATCATCGGCCCCAAATTAGATAGGCT
4,277 TTTGGAGTGGGATCCCTTCTACTTTTGATTTCTTTATAAAATTTTAAAATAGCTTTGTTG
AGATAGTGTTCACATACCATACAGTTCACCCATTAAAAGTGTTCAATTCAGTGATTAGGC
CAGGTGTGGTGGCTCATGCCTGTAATCCCAGCATTTTGGGAGGCCAAGGCAAGTGGATCA
4,457 CTTGAGGTCAAGAGTTTGAGACTAGCCTGGCCAACATGGTGAGAACTTGTCTCTACTAAA
AATACAAAAATTAACTGGGCATGGTGGTGTGCACCTGTAATTCCAGCTACTTGGGAGGCT
GAGGCAGGAGAATCACTTGAACCTGGGAGGTGGAGGTTGCAGTGAGCTGAGATTGCACCA
4,637 CTGCACTCCAGCCTGGATGACGGAGCAAGACTCTGTCTCCAAAAAAAAAAAAAAAAAAAG
TGTTCAATGTTTTTTAGTATATTCACAGAGTCATGCAACCATCACTATAATTGCTTCTAG
AACATTTTCATCATCCCCCAAAAGAAAGCCTTCGTTACGAATTTTAATTAGCTGAGATTC
4,817 TGAACTCTGGGGGAATTTTGTATTCTAGAAATATTTTTTACTAATATGCTACAGTTGTAT
TTGTCATGCTGGTGAAAAGATGTGGTCTTTCACCTGGATGCTTTCTCATTAAGCATTATT
TTTCTGTTTAGCTTCCTGTGTGAGCAAACATTTTCTCAGCTTGATACTCAGTGCATCAGC

FIG.4D

```
4,997  GGCTTGCAGAAGAGACTGCCTAGGCCTGCTCTGTCCAGTACGGTAGCCACAAGTCACTTG
       TGGCTACTGAACACTTGAAATGTGGCCAAGGCAAATTGGGACAGGCTGTGAATGCAAAAT
       ATACAAGATTTGGAACCCTTAGTATGAAGAAAAGAATGCAAAATATCCCAGTAATAACTT
5,177  TTACATTGATGATATGTTAAAGGACAATATTTGAATATGTTAGGTTAAATAAAATTAATT
       TCACCTGTTTCTTTTTACTTTTAAAAATATGGCCGCTGGAACATTTAAAACTCCCTATGT
       GGTTTGCTTTGTGTTTCTATTGGACAAAGTTGGTCTAGACAGTACAAGGTGTGAAGACAC
5,357  CGCCCTCTGCTGGAGAAGATGCTGGATTTTTATTTCACCTACAGGAAGAGACGTCTAAGT
       AGCAATTAGATGCTAAACTAATGCTGCCTCAGGAAAGAATCAAAAGAGAAAGAGTGAAAC
       CAGGCCGGGCGCGGTGGCTCACGCCTATAATCTCAGCNACTTTGGGAGGCCAAGGCGAGG
5,537  GGATCACGAGGTCAGGAGATCGAGACCTTCCTGGCTAACCCCGTCTCTATTAAAACTACA
       AAAAATTAGCCGGGCATGGTGGCACGTGCCTGTAATTCCAGCTAGTCGGGAGGCTGAGGC
       AGGAGAATAGCTTAAACCCAGGTGGCGGAGGGTGCAGTGAGCTGAGATGTGCCACAGCAC
5,717  TCCAGCCTGGGCAACAGAGCCAGACTCTATCTCAAAATAAGGAAAAATAAAAAAGAAAAG
       AAAGAAAGTCCATAAATTGAGACTCCTAGAGATACTAAATGGTAGAATGGGAATTTGAAT
       TTAAATTTATAAGATGTTCACTCTCGGAGATCATAGGTCATTGTTGTCCTCCTCCTTTTC
5,897  ATGACAGGAACTAGCAATGAAGAGCTCTGACTATGTGCTAGGTACTACTCTGAGAACCTA
       ACATTTGTATCTCCTTATTAACTCTATTACTGCCCCATCCTACAGATGAGAAAATTGAGG
       CACAGGAAGTTTAAGTTGGCCAAGATCACACAGCCAGTAAGGGGCAGACATTGAAAGGTC
6,077  ATTTTGCCTGCCTTATCCCCAGCCTCCAGGCAGTGGCAGAGTTAGCTCATTTTGGACAAA
       CAGCTCTCCCAGACCAGACATTGTAAGCTATACTCAGGAATCATAGGAAAGATTATGATA
       GAATAATATATAGTTACAAAGAAAAGAAAGAAAATCCAATGGGAGAATATTTACTGTTTT
6,257  CTATATTAAAGTGTTTAATGTTTATGTTTTAGAGGAATATTGTTTATTATAGCAATTTA
       GAAAACAAAATGAGAAAAAAAATCACCAAAGATTCTACCTCCAGTTATTTTTGTGTATTT
       CCTTCCATTTTTCCCCCCATGTCTGTTTATATAATTGAAACTATTATTCATGCAAAGAGG
6,437  TATTCTGATTTTCTCAGTTATTTTTATTTATTTTTAATTTTGTAAATAAACTTTTTTCTT
       CTGAGACAGTCTCGCTGTGTCACCCAGGCTGAAGTGCAGCCGTGCAATCTTGGCTCACTG
       TGACCTCCCAGTCTCAAGCAATCTTCCTGCCTCAGCCTCCTAAGTAGCTGGGACTGCAGA
6,617  TGTGTGCTACCACATCCAGCTAATTTTTAAAATCTTTTTTCTCTTTTTTGGTAGAAATGG
       GAGTCTCTCTATGTTGCCCAGCCTGTATTGAACTCCTGGGCTCAAGTGATCCTCCCACCT
       CAGTCTCCCAAAGTGCTGGGATTTCAGGCATGAGCTACCACACCCAACCTAATTTTTATT
6,797  TTTATTTTATTAAAAAAAAAAGTTTTGCCTACCCGCCTCTCACCCTCTCACTCATTTTT
       AAGTATAGGTTTTTCTACAATGCCACATTGTCTTTTCCATAAAAAGTACTTTCGGCCGGG
       TGTGGTGGCTCACACCTGTAATCCCAGCACTTTGGGAGACTGAGGCGGGTGGATCACCTG
```

FIG.4E

```
6,977  AGGTCAGGAGTTCGAGACCAGCCTGGCCAACATGGTGAAACCCCATCCCTACTAAAAATA
       CAAAAATTAGCTGGATATGATTGTGGGCACCTGTCATCCCAGCTACTCGGGAGGCTGAGG
       CAGGAGAATCGCTTGAACCTGGGAGGCAGAGGTTGCAGTGAGCCGAGATTGTGCCACTGC
7,157  ATCCCAGCCAGGGCAACAGAGCGAGACTTCATCTCAAAAAAAAAAAAAAAAAAGTACTTTT
       CTTCATTTGGTTAGTATTCTCTTATGAGTTGATGCCTTGTAATTTATCTGAATGTTTTCC
       ATTATTTTGTGGTGAGCTTTAAAACTACCCTTCCTGACTTTCAAGAATCCTAGACATGCT
7,337  CCTTGTTGCTAGGTAATTATTAGTTGCACTCATTAGAATAAAGTATATGCTTGGAGTGGG
       GAGGAGATGAACTTTTTGAAGGGCGGTGAAGTATTTCTCACCACCAGGCCTTTGTCTTTG
       CTAAACTGAGGAAGGAAGATTTTATTTCATTAGCTAACAAAGAACCTCCTATATAGGCCG
7,517  GGCATGGTGGCTCACGCCTGTAATCCTCACATTTTCAGAGGCCAAGGTGGGTGGATTGCC
       TGAGCTCAGGAGTTTGAGACCAGCTTGGGCAACATGGCAAAACCCCATCTCTACTAAAAA
       TACTAAAAATTAGCTGGGCGTGGTGGTGAGTGCCTGTAATCCCAGTTACTCCAGAGGGTG
7,697  AGGCAGAAAATTGCTTGAACCCGGGAGGTGGAGGTTGCCATGAGCCGAGATCGTGACAGT
       GCACTCCAGCCTGGGCGACACAGCAAGACTCTCTCTCAATAAAATAAAATAAAATAAAAT
       AAAATAAATACATAAATAAATCTCCTATATAACCTCATAATATCAGATTTGGAGCCTTTT
7,877  CCATAGAAATGAAATTCAGAAGAAGCTGAGACTCAGATATTCCAAGCTGCCTGGTGCTCT
       GTGAATAGAGGAGACTTGTTCTTGTGAAATCTGAGTGCAAAGACACAGGACAAATTGTTA
       TCTACTTTTCATTCCTAAGGATACTGTATGGCCCTAAAACACAAGAACTAGAATTCTGTG
8,057  ATACCACGGGTACTCCACAGTGTGTTCCTTCCCCTTTCTGAACCTGATTTGTCTCATCTC
       TATGAAAAGATGTGGGCTTTGGGGTCAGATGTGGGTTGGAATCCTAGCGCCTGTGTGGCT
       GCAATTTTCTTTTGTGTAAAATTGAGATAATAGTACAAAAGTAACAACAGTTAATATTAT
8,237  CAAGTGCTTACTGTGTGCCTGGCACTGTGTTAAATTCTCTAAGTGTATTTTCTCATTTAA
       TTTTTGTGATAGGCTTATGACACTATTAGTATCTTCATATTACAGTGAGGGTTCAGAGAA
       GTTAAGGTTCCATAACTAGTCAGCAGACCTGGGACTTCACTCCAGGCAGCTGATTCCAAA
8,417  GCCTATTCTAACTTTAAACTGCTACTTTTTGGAGTGTTGTAAGAAGGACAATTTATATAA
       AATGTTGGCACATAGTGGGTGCTGCTGTTATATGAATGGGCACAAAATCTGTCTACATTT
       TGCCTTTTACCAAATTTAGAATCTATTTAGTTAAAACCTTCTTAGGGCGGGTGGAGTGCA
8,597  GTTGCTCATTCCTGTAATCTCAGCACACTGGGAGGCCAAGGCAGGAGGATTGCTTGAGCC
       CAGGTGTTTGAGACCAGCCTGGGCACATAGTGAGACCCCATCTCTCCAAAAAACAAACA
       AACAAACAAAAACAAAACAAAACTAGCTGGGCGTTGTGGTGCCCCTGTATTCCCAGCTAC
8,777  TCAAGAGGCTGGGGTGGGAGAATGGCTTGAGCCCAGGAGTTCAAGGTTGCAGTGAGCTAT
       GATCACAGTACTGCACTCCAGCTTGGGCAGCCGACTGAGACCCTGTCTCGAAAAAAAAAT
       AAAAATAAAAACTTCTTAGGACAGAGTGATTAGAAGCTCTCTAGTAGATACTTAGTAACA
8,957  ATGTGGGTTCCTCGGGCAG
```

FIG.4F

```
                    GTTATCCTACGCAGAGAGCCAGGTACCAATGGGTGCGCTGC
      AATCCAGACAGTAATTCTGCAAACTGCCTTGAAGAAAAAGGACCAATGTTCGAACTACTT    EXON 2
      CCAGGTGAATCCAACAAGATCCCCCGTCTGAGGACTGACCTTTTTCC

GTAAGTGGACTTT
 9,137 TCTCTAATTAATTAATTAATTACTTATTTATTTGAGACGGAGTTTCACTTTTCTTGCCCA
       GGCTGGAGTGCAATGGCGCAATCTTAGCTCACTGCAACCTCCGCCTCCTGGGTTCAAGCG
       ATTCTCCTGCTTCAGCCTCTGGAGCAGCTGGGATTTCAGGCGCCTGCCACCATGCCCAGC
 9,317 TAATTTTTTTTTTTTTTTTTTTTGAGACGGAGTCTCACTCTGTTGCTCAGGCTGGAGTG
       CAGTGGCGCAATCTCGGCTCACTGCAAGCTCCACCTCCTGGATTCACGCCATTCTCCCGC
       CTCAGCCTCCCGAGTAGCTGGGACTACAGGCACCCGCCACCACGCCCGGCTAATTTTTTT
 9,497 GTATTTTTAGTAGAGACGGGGTTTCACCTTATTAGCCAGGATGGTCTCGATCTCCTGACC
       TAGTGATCCGCCCGCCTTGACCTCCCAAAATGCTGGGATTACAGGCGTGAGCCACTGCGC
       CTGGCCTAATTTTTTGTATTATTAGTAGAGACGGGCTTTCATCATCTTGGCCAGGCTGGT
 9,677 CTCAAACTCCTGACCTCAGGTGATCCACCCACCTTGGCCTCCCAAAGTGTTGGGATTACA
       AGCATGAGCCACTGTACCCGGCCTTTTCTCTAATTTTAAAGTGTCTGTAATTTCACAACC
       TCTTGGCACAGATGTGGGAGTGTTTTTCTTCAAGCTGTCCAGAGTGTTTTGCTTCGAGCT
 9,857 CTTGCTTTGGTAGTTTGGCTCTTACTCTGCAGTACATGGTAAAAGTGTACTGTATATACT
       GGCATATGACATGTGCGAGTATACATGATTCACCTATGTTTTTGAAATTTTTTTTGTGGA
       TGGTAGAGAGGAGCATTGAGGACTTTTCATCAACAGGTATTGAAAATGATTGAACATTGT
10,037 TTTATTTGTGTAAACAGAACACACTATATATAAAAATCCAATAATTAACTGAATGGATAA
       GCAAAATGTGGTATAAGCATACAAAGGAATATTATTGGGTCATAAAAAGAATGAAGTACT
       GATACATGCTACAACATAGATAAACCTTGGAAACATTATGCAGAGCGAAGGAAGGCCAGA
10,217 CACCAAAAGCCACATATTGTATGATTCCATTTAGATGAAATGTCCAGAATAGGCAAATCC
       CTAGAGGCAGAAAGTAGATTAGTGGGTTACAGGGGCTGGGGAAAGGGAGGAATAAGGAGT
       GACTGCTAATGGGTATGAGGGTTTTTTTTGGAGGAGGTGATTAAAATGTTCTTCTGCCAG
10,397 GTGTGGTGGCTCATGCCTGTAATCCCAGCACTTTGGGAGGCCGAGGCGGGAGGATTGTTT
       GAGCCCAGGAGTTTGAGGCCAGCCTGGGCAACATAGTGAGACCCTATCTCTATTTCAAAT
       ACATTTTTTATATTAAAAAAATGTTCTTCAAGTAGTTGGTAATTATTTTTAAAAATGGCC
10,577 AGGTGCAGAGGCTCATGCCTGTAATCCCAGCACCTTGGGAGGCTGAGGTGGGAGGATCCC
       TTGAGCCCAGGAGGTTTGGGACCAGCCTGGGCCATACAGCAAGACCCTGTCTCTACAAAA
       AATACAAAAATTAGCTAGGCATAGTGATGTGCACCTGTGGTCCCAGCTACTCGGGAGGCT
```

FIG.4G 10,757 GAGGTAGGAGAATCTCTTGAGCCTATGTTGAGCCTGCAGTGAACCCTATTTATGCCATTG
CACTCCAGCCTAGGCAACAGAGTAAGACTCTGTCTCAAAAAAAGAAAAAAAAAATTAGGG
AAAGGAAGAATAATTAGCCAAGACTTGTAAAACAAAAATCAAATCTCTTCTTTTGATCAC
10,937 ATAAAACTTGCTTTAAACTTGCAAAAAAGACCTGATATAAATTCATAAGTAACAAAAAAT
TGAATTATATTAGAAACCATTAATTCAATGAATACTAAAGCTATGTAGGATGTAGCAAAA
TATACATATTAAGAAAAGGATTATCATAAAAGTTTTAATCTCCAGGCTCAAACCTAGAAA
11,117 ATCACTCTCCTCAAAGCCAGGGTTAATCATCATGCTCCAAACCAGGTACATTTCACATCA
CTTTGGGATCCTGGCAACTTTCTCTTTTGTTTTTTTTTTTTTTGAGACAGGGTCTCCT
CTGTCACCCAGGATGGAGTGCAGTGGTGTGATCATAGCTCACTGCAGCCTGCAACTCCTC
11,297 AAGTGATCTTCCTGCCTCAGCCTCCCAAGTAGCGGGACCACAGGCACACAGCACCATGCC
CATCTAATTAAAAAAATTTTTTTTTGTAGAGACAGGGGTCTCTGTACATTTCCCAGGCTG
GTCATGTACTCCTAAGCTCAAGCAGTCCTCCCACCTCAGCCTCCCAAAGTGCCGGAATTA
11,477 CAGTCATGAGCCACCATTCCCAGCGCTGGTGACTTTCTCCATCACTGGTGACTTTCTCCA
TCACTGGTATTCACTGCATTAGTGATGACATCATTACAATCTTCAATATGCAACTTTGTA
GTCCTACTCTTGCATTCTTACTTTAAAGCCTCAGCATTAAGTTTGAATGTAATATTACAG
11,657 CATCCTTCATTACTTTAAATCATTGGTTTCAATAGTAATTCATTTAAATCTAAAATGTTA
GGCTGCAGTGGCTCATGCCTGTAATCCCCCCAGTTTGGGAGACTGAGGTGGGAGAATCAC
TTGAGGCCAAGAATTTGAGACCAGCCTGGGCAACACGGCAAGACCCCATCTCTAAAAATT
11,837 AGTGGCCCGGCGCCTGTGCCTCACGCCTGTAATCCCAACACTTTGGGAGGCCGAGGCGGA
TAGCTTGAGGTCAGGAGTTCAAGATCAGCCTGGCCAACATGGCGGAAACCCATTTCTACT
AAAAATACAAAAATTAGCTGGGCATGGTGGCACGCCTGTAATCCCAGCTATTGAGAGGCC
12,017 GAGGCAGGCAGACTGGGAGGCCAAGGCAGGCAGATTGCTTTGAGACCTGCCTGGGTAACA
TGGAGAAATCCTGTCTCTACAGAAAAATACAAAAATTAGCCAAGCATGGAGAAACCTCGT
CTCTATAGAAAGACACAAAAACTAGCCATGCATGCCTGTGGTCCAGCTACTCGAAAGGCT
12,197 GAGATGGGAGGATTGCTTGATCCTGAGAGGTCAAGGCTGAAGTGAGCCATGGTGTGGCAC
TGCACTCCAGCCAGGGTGACAGACTAAAACCTTGTCTCAAAATAAATAAACACATTTAAA
ATAAATAAATACAATTAAAACTAAAATTAAAAAATAAAATAAAATGTTAAGAGAATAGCT
12,377 CAAATTCTCCAAAAGAACTCTTGCACACCATTCCTCCTCTTCTCAAATCTCTATTTTCCT
TCCCCAAAGCCAGTAACTGCTTCTCACCCTGACCCTGTGCTTTCTTTCCCGTCATTGCGA
AAGAATGGTCCTTGCTTCTGTGCTGATCCCAAACCCTTTTGCCCTCAGATCCTCCTGTCC
12,557 TTCCCTGGCCCTGCTCTGTATTGGCTGTGGGGTGGGGGTGGCGGTGGAACTGACCCCTGG
GGTCTGCATTTCTCAGGCTCCCAGGGCTGTGGCTGACTTTGGCCAATGGGAGGCAAGGAC
GGGAGACTGAGAGCTTGGGAGGAAGGGAGAGAGGTATGTTTCTTCTCCTTACTCCCTGCC

FIG.4H 12,737 TGGGGTGGCACCTTGGGCAGGACTCTGTTTTGCCCATGGCCTCAGCTCCCACCAGATGCC
TCTAGTCCCTGGGCTCAGGAAATAGACAACCTCCTTCCACTATCGCTGTAGCCCAAGGAG
GGAAGTATTTTTTTTCTTTCTTTCTTTCTTTCCTTTTTTTTTTTACAGAGTCTCACTCT
12,917 TGTTGCCCAGGCTGGAGTGCAGTGGTGCGATCTCAGCTCACTGCCACCTCTGCCTCCCGG
GTTCAAGTGATTCTCCTGCCTCAGCCTCCAGGGTGTGCCACTATGCCCAGCTAATTTTTG
TATTTTTGGTAGAGACGGGGTTTTGCCATGTTGACCAGGCTGGTCTTGAACTTCTGACCC
13,097 CAAATGATCTGCCTGCCTCGTCCTCCCAAAGTGCTGGGATTACAGGCATGAGCCACTGTG
CCTGGCCGAAGGAAATATTTTCTTGCTATTGCTAATCTCTGGGTTACCTCGCTATCCCCC
ATTTAGCTTCACTTCTCCTCCATCACCTGTATGAGGAATTCCCTCTGTGTTAAATATCTG
13,277 GAGAAGTTTCCTGATTGGACCCTGGCTGTTGCAGCTTCCAAGGCCACCTCTCTTTGTGGC
TGGTATCCTTTTCCCATGCATCTTCTCCAGGACTTCCATTCTGCAGTTATCTCTCTGAAC
TCAGTGTCTTCTTCCCATCAGTATAGGGGTGGACTTTAGTATCTCCTATGTTTAGGCAAC
13,457 ATCTCTCCTTTGACTCTGCGTCTTCTCCAGTGGTTGCCCTTCTCTGCTCCTCTTCACAAT
AACACCTCCTGAAAGGGCCACCCATGCCTGCCCCCTCCTTTCCTCACCCCCTCTGTGGCT
GGACTTCTGTTCCTACACTCCACCCTGGTTGACAAAGTCACTGATTACTTCTCTATTTTC
13,637 AGCTTACTTGATCCTTAATTGCCTTCAAAAACAGCTAACTGGGCCATGCATGTAATCCCA
GCACTTCGGGAGGCCAAGGCAGGAGGATCACTTGAGCCCAGGAGTTCAGGACCAGCCTGC
CTGGGCAACATAGTGAGACCCTATCTACAAAAAATAGAAAAATTAGCCGGGCGTTGTGAC
13,817 TCATGCTTGTGGTCCCAGCTACAAAGGAAGCTGAGGTGGGAGGATGGCTTGAGTCCGGGA
GGGTGAGGCTGCAGTGAGCCATGATCACGCCACTGCACTCCAGCCTGCACAACAGAAGGA
GGCCCTTTCTGTAAAAAAAAAAATGGTTGACCACTCCTTCCTTGAAATGCTTTTTTCTTG
13,997 AGGCTTCCATGCCCTGCCTTATCCTGTTTCTTCCTACTTCTCTGGTTGTGCTTTTTCCTC
TGCTCAGTATTTAACATGTTGGTGTGACCCTGGCTCTGGCCTGGGCCCCCTTCTCTATCT
ACGTGCTTTCTCTCGACGACCTCCATCGGTTGCATGGGTTTAACTACCAAATCTGTGATT
14,177 CTAGCTCCGACACCCCAGGCTAAAGTAGCCACCTGGTCACTCCCTATTACATTGGTCAAT
TTCATTTCTCTGTGCCACCTATGATTTTCCTGATTTATTTATTCACTTTTCATTGTCTGT
CTTCCCCACTAAAATAAAAACTTCTTGAGAAGGGGCTTCATCGATCTGCCTCTGTTCTAT
14,357 CCCAGGCCCTCAAAACAAGGACCAGATATTCAACAAATATTTATTGAATGCGTACATGAA
TTAAAACTCTAATTGGTTGTATGCTGGTGGTTTATTATTTTCATGGAGGAAATGACTTGT
AGGCTGTGACACTCAGCTTTTGTCTCTGATGCTTTGTTGCCCTGTTCTGTCACCGAGGGC
14,537 TGTCGTCATTGCTCTGGCCATTTTGTGCTCTTTGAATTTCTAATCATCACACTCAACCCA
GAAGGCAGCCTTACCTTTCAGCACTCTTCAGCTGAATGAGTGCAAGTTGGAGGCAGGGTC
ATTTTTTGATAGGAAATTGAATGTTTATATGCTGGTAAATATAAAGCTTAGCTTTTTACA

FIG.41

14,717 AAGAATTTCTCAAAAGTGAGCTTTGTTGAAGCCCTGTAAATTGTTAGAACTTTTATGGAA
ATTTTAATTTAGGAAAAAATGTCATCTGTTTGGGCTGACTTAGTTGTTAGTTGTTTGTCC
TTTCTTTTTTTTGGTGGAGGGTATGGAGTTTTGCTCTTGTAACCCAGGCTGGAGTGCAGT
14,897 GGCGCGATCTCGGCTCACTGCAACCTCCGCCTCCTGGGTTCAAGCGATTCTCTCACCTCA
GCCTTCCGAGTAGCTGGGATTACAGGCATGCACCACCACACTTGGCTAATTTTTGTATTT
TAAGTAGAGACCGGGTTTCACTATGTTGGTCAGGCTGGTTTCGAACTCCTGACCTCAAGT
15,077 GATCACCCACCTTGGCCTCCCAAAGTGCTTGGATTACAGACATGAGCCACCACACCCGGC
CAAGAGGACTTCTTTTAAAAATGATTTCTTGGGCCGGGTGCAGTGGCTCACACCTGTAAT
CCCAGCACTTTGGGAGGCTGAGGTGGGTGGTTCACAAGGTCAGGAGTTTGAGATCAGCCT
15,257 GGCCAATATGGTGAAACTCCATCTCTACTAAAAATACAAAAATTAGCCAGGCATGGTGGC
GCACCCCTGTTGTCCCAGCTACTCGGGAGGCTGAGGCAGGAGAATCACTTGAACCTGGGA
GGTGGAGGTTGCAGTGAGCCGAGATGGCACCACTGCACTCCAGCCTGGGCAACAGAGCAA
15,437 GACTCTGCCTCCAAAAATAAAAATTAAAATGATTTCTTAAGTAAATTTCAAATATAGAAT
GTATATGCTAGTGATAACAAAATTAACACTGTTTATGCAAGTCTGCAATAGGTAGATGTG
AAGTTGATAGGTGCAATAAGTATAGGCAAACACATAGGAACATTTGACCTGTTTTTTTGT
15,617 TGATTTTAAAACATTGAATAATTGGGAAGCTTTTAAATCTCTTAATTTGAGCAACTAGAT
GGCTGTATTTATCTCCTTATATTAAAAAAACTATTATAATTATCTTTCCCACATATCAAA
CTCCACTGGTTTTTTTCCCATTTTTCTTTCATACTTCAG 15,797 GAATCGTATCTTCCCACTTTCTGAGGACTACTCTGGATCAGGCTTCGGCTCCGGCTCCGG AAAGACGAGAATCCAGGACTT
CTCTGGATCAGGATCTGGGAGTGGCTTCCTAACGGAAATGGAACAGGATTACCAACTAGT
AGACGAAAGTGATGCTTTCCATGACAACCTTAGGTCTCTTGACAGGAATCTGCCCTCAGA
15,977 CAGCCAGGACTTGGGTCAACATGGATTAGAAGAGGATTTTATGTTATAAAAGAGGATTTT
CCCACCTTGACACCAGGCAATGTAGTTAGCATATTTTATGTACCATGGTTATATGATTAA   EXON 3
TCTTGGGACAAAGAATTTTATAGAAATTTTTAAACATCTGAAAAAGAAGCTTAAGTTTTA
16,157 TCATCCTTTTTTTTCTCATGAATTCTTAAAGGATTATGCTTTAATGCTGTTATCTATCTT
ATTGTTCTTGAAAATACCTGCATTTTTTGGTATCATGTTCAACCAACATCATTATGAAAT
TAATTAGATTCCCATGGCCATAAAATGGCTTTAAAGAATATATATATATTTTTAAAGTAG
16,337 CTTGAGAAGCAAATTGGCAGGTAATATTTCATACCTAAATTAAGACTCTGACTTGGATTG
TGAATTATAATGATATGCCCCTTTTCTTATAAAAACAAAAAAAAAATAATGAAACACAGT
GAATTTGTAGAGTGGGGGTATTTGACATATTTTACAGGGTGGAGTGTACTATATACTATT
16,517 ACCTTTGAATGTGTTTGCAGAGCTAGTGGATGTGTTTGTCTACAAGTATGATTGCTGTTA
CATAACACCCCAAATTAACTCCCAAATTAAAACACAGTTGTGCTGTCAATACCTCATACT
GCTTTACCTTTTTTTCCTGGATATCTGTGTATTTTCAAATGTTACTATATATTAAAGCAG
16,697 AAATATAACC

FIG.4J

```
-504 AATTCTAGCAGACTCTGGACGTTAACGGAGACCGCTCATCCTGGGGGCTGAGAACCCAGCTCGGCTCGGAATGTT
-429 CCCTGCTTGTGCCTGACTCTGTGCGCGCCCAGCTTCTCTTTGATGTGCGCTGTGGATGAGCCGAGCTCAGTTCTG
-354 GAACAGCTGAGTCCTCCTGTCTGTTTAGATTGTTACCTGAAGGAAGGGAGGGGGAAGAAAGTGCTGATTCGACTT
-279 TTTGATGGGGAAAACTTTTTTTTTAAACATGCAAATGACAGATGGCAGAGCTTTTTGGAAAAAGAAAAAATAATA
-204 ACCACACAGCAAACGCCTAGGGGGAGTCCGGTGGAGTTTCATCATGGGTATGAACAGTTGTTGTTTTTTTCAACT
-129 TTCTTCTTCTTTCTGGGTGTTGATGTGGATCTCTTTCTATTTGTTCAGGAAACTGTGACGTGTGTTCTTGGGCAG
                                                              ┌→ exon
-54  GGTCTGAGGTTTTGGAACCTCTTTCTAAAAGGGACAGAAAGAGCACCCTGCTACATTTGCTAATCCAGAGGCTGA
                                 START                        1
     GTGGAGCCGAGCTGGTCAGG ┌ATG CAG GTT CCC GTC GGC AGC AGG CTT GTC CTG GCT CTC
                         │MET GLN VAL PRO VAL GLY SER ARG LEU VAL LEU ALA LEU
                                                        exon 1-│
     ┌GCC TTC GTC CTG GTT TGG GGA TCT TCA GTG CAA G│gt aagagacccaggatctttaattc-
     │ALA PHE VAL LEU VAL TRP GLY SER SER VAL GLN(GLY)│
               │-exon 2
     -( 8 kb)- ggttccttgttcgcaca g│GT TAT CCT GCT CGG AGA GCC AGG TAC CAG TGG GTC
                                  (GLY) TYR PRO ALA ARG ARG ALA ARG TYR GLN TRP VAL CGC TGC AAA CCG AAT GGC TTT TTT GCG AAC TGC ATC GAG GAG AAG GGA CCA CAG TTT
     ARG CYS LYS PRO ASN GLY PHE PHE ALA ASN CYS ILE GLU GLU LYS GLY PRO GLN PHE
                                                                       exon 2 ┤
     GAC CTA ATA GAT GAA TCC AAT AAC ATC GGC CCT CCC ATG AAT AAT CCT GTT TTg taa
     ASP LEU ILE ASP GLU SER ASN ASN ILE GLY PRO PRO MET ASN ASN PRO VAL(LEU)
                                                       │- exon 3
     gtagacttcatcgat -( 4 kb)- tttttctttgtattt ag│G ATG GAA GGA CCC TCA AAA GAT
                                                (LEU)MET GLU GLY PRO SER LYS ASP
```

FIG.5A

```
TTC ATC TCC AAT TAT GAT GAC TAT GGG TCA GGT TCG GGC TCC GGC TCT GGC TCC GGC
PHE ILE SER ASN TYR ASP ASP TYR GLY SER GLY SER GLY SER GLY SER GLY SER GLY

TCT GGC TCG GGT TCC GGC TCC GGA AGT GGC TTC CTA GGT GAC ATG GAA TCC GAA TAC
SER GLY SER GLY SER GLY SER GLY SER GLY PHE LEU GLY ASP MET GLU TRP GLU TYR

CAG CCA ACA GAT GAA AGC AAT ATT GTC TAT TTC AAC TAT AAG CCT TTT GAC AGG ATT
GLN PRO THR ASP GLU SER ASN ILE VAL TYR PHE ASN TYR LYS PRO PHE ASP ARG ILE

CTC ACT GAG CAA AAC CAA GAC CAA CCA GAA GAC GAT TTT ATT ATA TGA
LEU THR GLU GLN ASN GLN ASP GLN PRO GLU ASP ASP PHE ILE ILE STOP

ATGTGACGGTCTCTGTCTCCCCACCTCCATGTGGAACAATGTATTCAGTATACTTAGTGTACCACGTTTAAATGA
CCAGTCTCAGGATAAAGAGTTTTACAGAAAATTTAAAATGCCTGGAAAAGACTCTTGAATCCTGTTACCCCTTTC
CTCATTAACTCGTAAGGAATTATGCTTTAATGCTGTTACCTATCTTGTTGTTCTGGAAAATGCCTGCATTTATGT
GTATTGAATCAACATTTAAGAAATTAACACACACCCCCATTATTATACAATAACTTTCAAAGCCATACTGGTTTT
GAAAATTTTAATTTGATAGCAAGTTGATGAACAATCTTTCATACCTAAAGTGTTCAGGAACCCAACTCGCATTGT
GAATTACAAATATATTCCTTTATGTGATTAAAAAGAAAATAAAGTG
```

FIG.5B

| CONSTRUCT | | RELATIVE hGH EXPRESSION | |
|---|---|---|---|
| | | RBL-1 CELL | Rat-1 FIBROBLAST |
| pPG(-504/+24)hGH | −504 ▬▬▬▬▬▬▭▭▭▭ | 0.89 ± 0.15 (18) | 0.05 ± 0.02 (18) |
| pPG(-423/+24)hGH | −423 ▬▬▬▬▬▭▭▭▭ | 0.82 ± 0.13 (6) | ND |
| pPG(-333/+24)hGH | −333 ▬▬▬▬▭▭▭▭ | 0.79 ± 0.11 (6) | 0.03 ± 0.01 (6) |
| pPG(-250/+24)hGH | −250 ▬▬▬▭▭▭▭ | 1.24 ± 0.23 (8) | 0.05 ± 0.02 (8) |
| pPG(-190/+24)hGH | −190 ▬▬▬▭▭▭▭ | 2.52 ± 0.49 (8) | 1.06 ± 0.27 (8) |
| pPG(-118/+24)hGH | −118 ▬▬▭▭▭▭ | 3.21 ± 1.61 (14) | 1.21 ± 0.65 (14) |
| pPG( -81 /+24)hGH | −81 ▬▭▭▭▭ | 0.46 ± 0.16 (10) | 0.22 ± 0.12 (10) |
| pPG( -63 /+24)hGH | −63 ▬▭▭▭▭ | 0.34 ± 0.12 (8) | 0.20 ± 0.10 (8) |
| pPG( -40 /+24)hGH | −40 ▭▭▭▭ | 0.41 ± 0.12 (8) | 0.32 ± 0.09 (8) |
| pPG( -20 /+24)hGH | −20 ▭▭▭▭ | 0.00 (8) | 0.00 (8) |

HEMATOPOIETIC CELL SPECIFIC TRANSCRIPTIONAL REGULATORY ELEMENTS OF SERGLYCIN AND USES THEREOF

STATEMENT OF GOVERNMENT INTEREST

The research underlying this invention was supported with U.S. government funds; the U.S. government has certain rights in this invention.

CROSS REFERENCE TO RELATED APPLICATIONS

This application is a continuation-in-part of U.S. application No. 07/816,289, filed Jan. 3, 1992, now abandoned which is a continuation-in-part of U.S. application No. 07/635,544, filed Jan. 18, 1991, issued as U.S. Pat. No. 5,171,674, which is the U.S. National Phase of PCT/US89/03051, filed Jul. 13, 1989, which is a continuation-in-part of U.S. application No. 07/224,035, filed Jul. 13, 1988, now abandoned; the contents of each of these priority applications are fully incorporated herein by reference.

FIELD OF THE INVENTION

The invention is in the area of recombinant DNA technology. Specifically, the invention is directed to a hematopoietic cell-specific transcriptional enhancer element, a transcriptional suppressor element, and a promoter element, all present in the 5' flanking region of the serglycin gene; the invention is further directed to recombinant vectors containing such elements, hosts transformed with such vectors, and the use of vectors and hosts for recombinant gene transcription. The invention is also directed to purified protein factors that specifically bind to the transcriptional elements of the invention.

BACKGROUND OF THE INVENTION

The rat connective tissue mast cell was the first cell conclusively shown to store proteoglycans in an intracellular secretory granule compartment (Benditt et al., J. Histochem. Cytochem 4:419 (1956)). Rat connective tissue mast cells contain up to 25 pg/cell of an acidically charged ~750 kDa (kilodalton) proteoglycan that possesses a very small peptide core to which approximately seven heparin glycosaminoglycans of 75-100 kDa are attached (Yurt et al., J. Biol. Chem. 252:518 (1977); Robinson et al., J. Biol. Chem. 253:6687 (1978); Metcalfe et al., J. Biol. Chem. 255:11753 (1980)). Because the peptide core of mature rat heparin proteoglycan consists almost entirely of equal amounts of serine and glycine (Robinson et al., J. Biol. Chem. 253:6687 (1978); Metcalfe et al., J. Biol. Chem. 255:11753 (1980)) and because heparin glycosyaminoglycan is O-glycosidically linked to serine at serine-glycine sequences within its peptide core (Lindahl et al., J. Biol. Chem. 240:2817 (1965)), it was first postulated by Robinson and coworkers (Robinson et al., J. Biol. Chem. 253:6687 (1978)) that the mature peptide core of this proteoglycan is predominantly an alternating sequence of serine and glycine.

It is now known that many cells of hematopoietic origin (including serosal mast cells, mucosal mast cells, basophils, natural killer cells, cytotoxic T lymphocytes, eosinophils, macrophages, and platelets) store a family of proteoglycans in a cytoplasmic granule compartment that is distinct from the plasma membrane-localized and extracellular matrix-localized families of proteoglycans (Stevens et al., Cur. Topics Microbiol. Immunol. 140:93-108 (1988)). These intracellular proteoglycans (known as "serine-glycine rich proteoglycans," "SG-PG," "secretory granule proteoglycan," or "serglycin proteoglycans") have five to seven highly sulfated glycosaminoglycans attached O-glycosidically to a common 18,600 to 16,700 $M_r$ peptide core possessing a protease-resistant glycosaminoglycan attachment region that is a repeat of serine and glycine amino acids (Yurt et al., J. Biol. Chem. 252:518-521 (1977); Robinson et al., J. Biol. Chem. 253:6687-6693 (1978); Razin et al., J. Biol. Chem. 257:7229-7236 (1982); Stevens et al., J. Biol. Chem. 260:14194-14200 (1985); Seldin et al., J. Biol. Chem. 260:11131-11139 (1985); Bourdon et al., Proc. Natl. Acad. Sci. USA 82:1321-1325 (1985); Bourdon et al., J. Biol. Chem. 261:12534-12537 (1986); Avraham et al., J. Biol. Chem. 263:7292-7296 (1988); Avraham et al., Proc. Natl. Acad. Sci. 86:3763-3767 (1989); Stevens et al., J. Biol. Chem. 263:7287-7291 (1988); Alliel et al., FEBS Lett. 236:123-126 (1988); Stellrecht et al., Nuc. Acids Res. 17:7523 (1989)). The peptide core of this family of proteoglycans has also been referred to by a variety of names, such as "secretory granule proteoglycan peptide core protein," but most recently has simply been called "serglycin." Thus, the gene encoding this peptide is the serglycin gene.

Serglycin proteoglycans (serglycin with attached glycosaminoglycans) are stored inside cells as a macromolecular complex bound to basically charged proteins. Because these proteoglycans are bound by ionic linkage in the secretory granules of mouse and rat mast cells to positively charged endopeptidases and exopeptidases that are enzymatically active at neutral pH, it has been assumed that the serglycin proteoglycans prevent intragranular autolysis of the proteases. The proteoglycan/protease macromolecular complexes remain intact when they are exocytosed from activated mast cells (Schwartz et al., J. Immunol. 126:2071-2078 (1981); Serafin et al., J. Biol. Chem. 261:15017-15021 (1986); Serafin et al., J. Immunol. 139:3771-3776 (1987); Le Trong et al., Proc. Natl. Acad. Sci. USA 84:364-367 (1987)), presumably attenuating diffusion of the proteases from inflammatory sites and facilitating concerted proteolysis of protein substrates.

cDNAs that encode serglycin have been isolated from rat (Bourdon et al., Proc. Natl. Acad. Sci. USA 82:1321-1325 (1985); Bourdon et al., J. Biol. Chem. 261:12534-12537 (1986); Avraham et al., J. Biol. Chem. 263:7292-7296 (1988)), mouse (Avraham et al., Proc. Natl. Acad. Sci. 86:3763-3767 (1989)), and human (Stevens et al., J. Biol. Chem. 263:7287-7291 (1988); Alliel et al., FEBS Lett. 236:123-126 (1988); Stellrecht et al., Nuc. Acids Res. 17:7523 (1989)) cDNA libraries. These cDNAs encode 1.0-, 1.0-, and 1.3-kb transcripts in the mouse, rat, and human, respectively. The mouse serglycin gene resides on chromosome 10, is approximately 15 kb in size, and consists of three exons (Avraham et al., Proc. Natl. Acad. Sci. 86:3763-3767 (1989)).

Bourdon and coworkers (Bourdon et al., Proc. Natl. Acad. Sci. USA 82:1321 (1985); Bourdon et al., J. Biol. Chem. 261:12534 (1986)) isolated and characterized a cDNA from a rat yolk sac tumor cell that encoded an unusual 18.6 kDa proteoglycan peptide core with a 49 amino acid glycosaminoglycan attachment region of alternating serine and glycine. Because of the preponderance of these two amino acids, it was proposed that the peptide core of this proteoglycan (designated serglycin) was related to the peptide core of rat mast cell-derived heparin proteoglycan. Numerous molecular biology studies have been carried out on the cDNAs and genes that encode mouse, rat, and human serglycin. Using a 3' gene-specific fragment of a rat serglycin cDNA (Avraham et al., J. Biol. Chem. 263:7292 (1988)), it was demonstrated that this gene is expressed at relatively high levels in a variety of mouse and rat mast cells irrespective of what type of glycosaminoglycan is polymerized onto the peptide core (Tantravahi et al., Proc. Natl. Acad. Sci. USA 83:9207 (1986)). This gene is also expressed in many other hematopoietic cells that possess secretory granules (Tantravahi et al., Proc. Natl. Acad. Sci. USA 83:9207 (1986); Stevens et al., J. Immunol. 139:863 (1987); Stevens et al., J. Biol. Chem. 263:7287 (1988); Rothenberg, M. E., Pomerantz, J. L., Owen, W. F., Avraham, S., Soberman et al., J. Biol. Chem. 263:13901 (1988); Stellrecht et al., Nucleic Acids Res. 17:7523 (1989); Perin et al., Biochem. J. 255:10017–1013 (1988); MacDermott et al., J. Exp. Med. 162:1771 (1985); Nicodemus et al., J. Biol. Chem. 265:5889 (1990)) and it appears that the same peptide core is used in all of these cell types. The selection of the type of glycosaminoglycan that will be synthesized onto this peptide core therefore appears to be a cell-specific event that is not exclusively dependent on the translated peptide core.

Although serglycin is specifically expressed in hematopoietic cells, no tissue specific hematopoietic cell transcriptional regulatory elements have yet been identified. A need exists for such elements as they would allow, for the first time, the regulated induction or expression of recombinant genes in hematopoietic cells, especially in hematopoietic cell culture systems.

SUMMARY OF THE INVENTION

Recognizing the importance of understanding tissue specific gene expression in hematopoietic cells for the expression of recombinant genes in cells of hematopoietic cell linage, and cognizant of the need for DNA regulatory elements or motifs capable of specifically stimulating or inhibiting transcription for the controlled expression of genes in such cells, the inventors investigated the 5' flanking region of the serglycin gene in an attempt to identify such motifs. These studies have culminated in the identification of three motifs in the 5' flanking region of the mouse serglycin gene that regulate the constitutive transcription of that gene.

According to the invention, there is first provided, in isolated form, a genetic sequence of approximately the proximal 500 nucleotides of the 5' flanking region of human and mouse serglycin gene, such flanking region providing transcriptional regulatory elements sufficient to direct expression of operably linked recombinant genes in hematopoietic host cells in a constitutive manner.

The invention further provides, in isolated form, genetic sequences encoding a positive transcriptional regulatory element, herein termed an enhancer element, such element corresponding to nucleotides −118 through −81 of the mouse serglycin gene (5TCTGGGTGTTGATGTGGATCTCTTT-CTATTTGTTCAGG-3' [SEQ ID No. 16]), and an equivalent position of the human serglycin gene, nucleotides 508–545 of SEQ ID No. 11) and such element being dominantly active to stimulate transcription of operably linked genes in hematopoietic host cells.

The invention further provides, in isolated form, genetic sequences encoding a unique and atypical eukaryotic promoter element, such promoter element corresponding to nucleotides −40 through −20 of the mouse serglycin gene (5'-GAACCTCTTT-CTAAAAGGGAC-3' [SEQ ID No. 17], and an equivalent position of the human serglycin gene nucleotides 585–604 of SEQ ID No. 11), and such element being dominantly active for the promotion of transcription in operably linked genes in hematopoietic host cells.

The invention further provides, in isolated form, genetic sequences encoding a negative transcriptional regulatory element, herein termed a suppressor element, such element corresponding to nucleotides −250 through −190 of the mouse serglycin gene (5-TGCAAATGACAGATGGCAGA GCTTTTTGGAAAAAGAAAAAA TAATAAC-CACACAGCAAACG-3' [SEQ ID No. 18], and an equivalent position of the human serglycin gene nucleotides 396–432 of SEQ ID No. 11), and such element being dominantly active to inhibit transcription of operably linked genes in fibroblast host cells.

The invention further provides expression vectors containing such genetic sequences, such expression vectors providing such genetic sequences in a manner that permits a gene of interest to be operably linked to the regulatory element encoded by the genetic sequence such that transcriptional expression of the gene of interest is under the control of the genetic sequence of the invention.

The invention further provides expression vectors containing such genetic sequences operably linked to a gene of interest.

The invention further provides host cells transformed with such expression vectors.

The invention further provides methods for the production of a peptide of interest, or for inhibiting the production of a peptide of interest, using the genetically engineered genetic sequences, vectors and hosts of the invention.

The invention further provides methods for the inhibition of the expression of a gene of interest, using the genetically engineered genetic sequences of the invention to direct the transcription of an anti-sense RNA complementary to the gene of interest.

The invention further provides cell-free preparations of $B/F_{(-250/-161)}$-I, a trans-acting factor extractable from the nuclei of rat basophilic leukemia-1 cells and rat-1 fibroblasts, such factor specifically binding to the suppressor element of the invention.

The invention further provides cell-free preparations of $B_{(-250/-161)}$-II, a trans-acting factor extractable from the nuclei of rat-1 fibroblasts, such factor specifically binding to the suppressor element of the invention.

The invention further provides cell-free preparations of $B_{(-118/-81)}$-I, a trans-acting factor extractable from the nuclei of rat basophilic leukemia-1 cells, such factor specifically binding to the enhancer element of the invention.

The invention further provides cell-free preparations of $F_{(-118/-81)}$-I, a trans-acting factor extractable from the nuclei of rat-1 fibroblast cells, such factor specifically binding to the enhancer element of the invention.

The invention further provides cell-free preparations of $B/F_{(-40/+24)}$-I a trans-acting factor extractable from the nuclei of rat basophilic leukemia-1 cells and rat-1 fibroblast cells, and to $F_{(-40/+24)}$-II, $B_{(-40/+24)}$-II, trans-acting factors extractable from the nuclei of rat-1 fibroblast cells or rat basophilic leukemia-1 cells, respectively, such factors specifically binding to the enhancer element of the invention.

BRIEF DESCRIPTION OF THE FIGURES

FIG. 2. Consensus nucleotide sequence of the HL-60 cell-derived cDNAs and the predicted amino acid sequence of the translated proteoglycan peptide core (serglycin) [SEQ ID Nos. 9 and 10]. The arrow indicates the putative site of cleavage of the signal peptide. Stop codons are indicated by * * * . The number on the right and left indicate the amino acid and the nucleotide in the respective sequence. The XmnI and AccI restriction sites are indicated. The 5' end of the cDNA-H12 was 4 bp longer, and the 5' end of cDNA-H19 was 14 bp shorter than cDNA-H4. cDNA-H8 differed from the cDNA-H4 in that it had an extra thymidine (shown in parentheses) at the 3' end of its cDNA.

FIG. 4. A Nucleotide sequence of the human serglycin gene [SEQ ID Nos. 11 (nucleotide sequence and 12 (protein sequence)]. The nucleotide sequences of the 5' flanking region, the exon/intron junctions, and the three exons are depicted. The hydrophobic signal peptide of the translated proteoglycan peptide core in exon 1 and the serine-glycine rich glycosaminoglycan attachment region in exon 3 are boxed. The polyadenylation site in exon 3 is underlined.

FIGS. 4B–4J. The complete nucleotide sequence of the human serglycin gene, including introns [SEQ ID No. 15].

FIGS. 5(A and B). Nucleotide sequence of the mouse serglycin gene [SEQ ID Nos. 13 (nucleotide sequence) and 14 (protein sequence)], Avraham, S. et al., J. Biol. Chem. 264:16719–16726 (1989). The nucleotide sequence of the 5' flanking region, the exon/intron junctions, and the three exons are depicted. The arrow indicates the probable transcription-initiation site. The hydrophobic signal peptide of the translated proteoglycan peptide core is boxed in exon 1. The di-acidic amino acid sequence that has been proposed to dictate glycosaminoglycan addition to proteins and the serine-glycine rich, glycosaminoglycan attachment region are boxed in exon 3. The polyadenylation site in exon 3 is underlined.

The numbers on the right are the hGH values obtained at 4 d relative to those cells transfected with the control plasmid, pSV40-hGH. The indicated hGH activities represent the mean ±SD values of data from 5 to 6 experiments of 4-d duration, with each experiment performed on 2-3 replicate dishes of cells.

Figure 10:
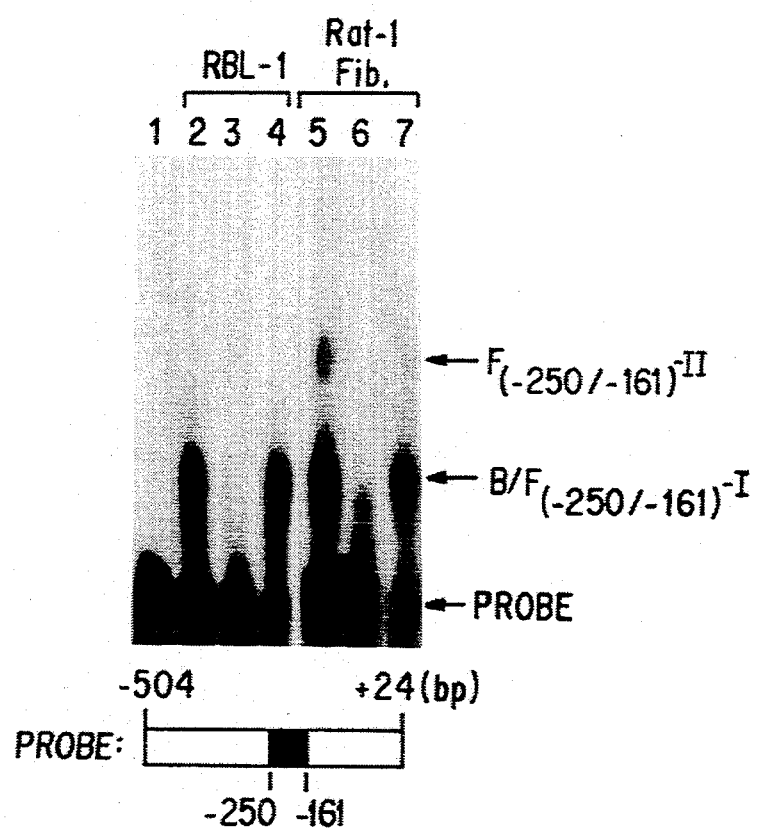

FIG. 10. Detection of trans-acting factors in the nucleus of rat basophilic leukemia-1 cells (RBL-1) and rat-1 fibroblasts (Rat-1 Fib.) that bind cis-acting elements in the putative suppressor region of the 5' flanking region of the mouse serglycin gene. Gel mobility shift assays were performed with the diagrammatically depicted nucleotide sequence in the 5' flanking region of the mouse serglycin gene. In lane 1, 1 ng of the $^{32}$P-labeled DNA fragment (residues −250 to −161) was electrophoresed in the gel in the absence of nuclear extracts. In lanes 2 to 4 and lanes 5 to 7, the probe was incubated before electrophoresis with nuclear extracts from rat basophilic leukemia-1 cells and rat-1 fibroblasts, respectively. Competition assays were performed using 5 ng of the same nonradioactive DNA probe (lanes 3 and 6) or 100 ng of sonicated salmon sperm DNA (lanes 4 and 7). The probe and the trans-acting factors present in fibroblasts ($F_{(-250/-161)}$-II and $B/F_{(-250/-161)}$-I) and rat basophilic leukemia-1 cells ($B/F_{(-250/-161)}$-I) are indicated on the right.

Figure 11:
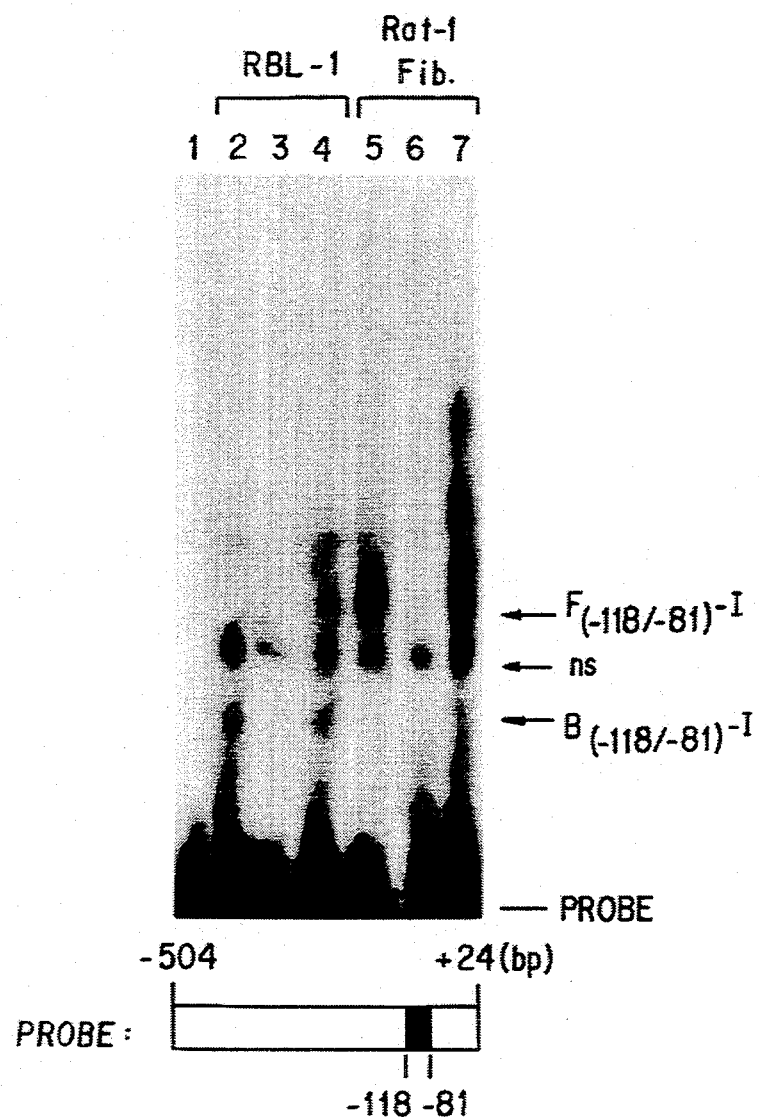

FIG. 11. Detection of trans-acting factors in the nucleus of rat basophilic leukemia-1 cells and rat-1 fibroblasts that bind cis-acting elements in the putative enhancer region of the 5' flanking region of the mouse serglycin gene. Gel mobility shift assays were performed with the diagrammatically depicted nucleotide sequence in the 5' flanking region of the mouse serglycin gene. In lane 1, 1 ng of the $^{32}$P-labeled DNA fragment (residues −118 to −81) was electrophoresed in the gel in the absence of nuclear extracts. In lanes 2 to 4 and lanes 5 to 7, the probe was incubated before electrophoresis with nuclear extracts from rat basophilic leukemia-1 cells and rat-1 fibroblasts, respectively. Competition assays were performed using 5 ng of the same nonradioactive DNA probe (lanes 3 and 6) or 100 ng of sonicated salmon sperm DNA (lanes 4 and 7). The probe, nonspecific (ns) bound probe, and the trans-acting factors present in fibroblasts ($F_{(-118/-81)}$-I) and rat basophilic leukemia-1 cells ($B_{(-118/-81)}$-I) are indicated on the right.

Figure 12:
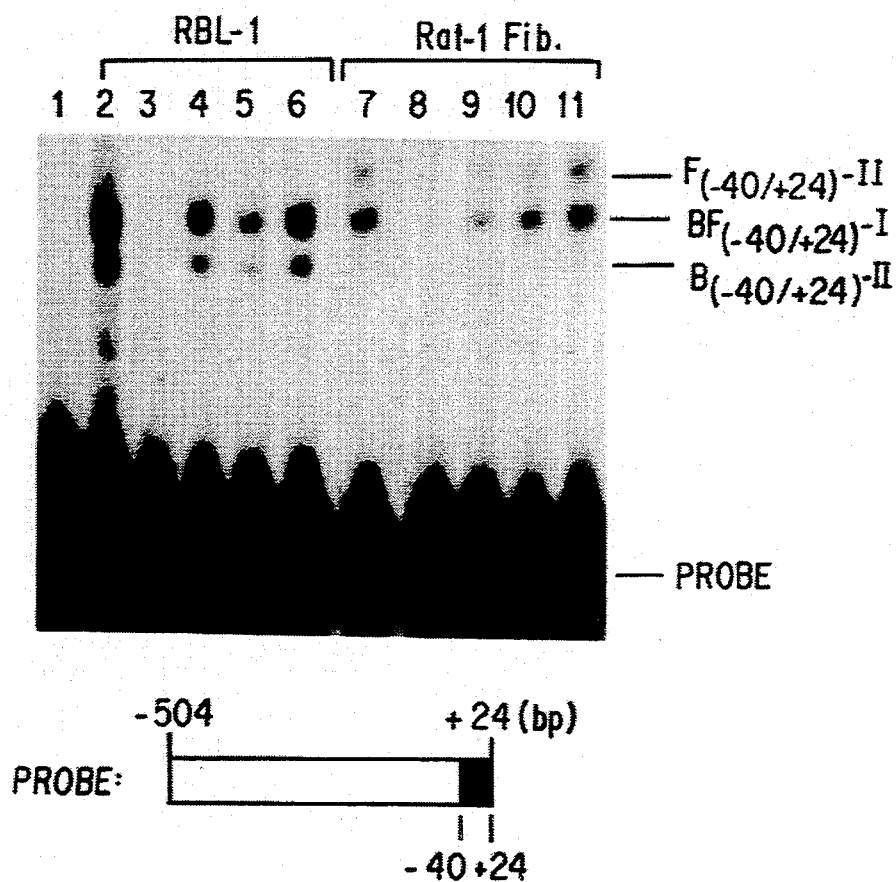

FIG. 12. Role of residues −28, −30, and −38 in the proximal promoter region of the mouse serglycin gene in its interaction with trans-acting factors in the nuclei of rat basophilic leukemia-1 cells and rat-1 fibroblasts. Gel mobility shift assays were performed with the diagrammatically depicted 64 bp nucleotide sequence in the 5' flanking region of the mouse serglycin gene (residues −40 to +24) prepared with and without point mutations. In lane 1, 1 ng of the $^{32}$P-labeled oligonucleotide was electrophoresed in the gel in the absence of nuclear extracts. In lanes 2 to 6 and lanes 7 to 11, the probe was incubated before electrophoresis with nuclear extracts from rat basophilic leukemia-1 cells and rat-1 fibroblasts, respectively. Competition assays were performed with 5 ng of nonradioactive DNA that corresponded to the probe (lanes 3 and 8) or 50 ng of nonradioactive DNA that had a mutated residue −30 (lanes 4 and 9), −28 (lanes 5 and 10), or −38 (lanes 6 and 11). The probe and the retarded trans-acting factors present in fibroblasts ($F_{(-40/+24)}$-II and $B/F_{(-24/+24)}$-I) and rat basophilic leukemia-1 cells ($B_{(-40/+24)}$-II and $B/F_{(-40/+24)}$-I) are indicated on the right.

Figure 13A:
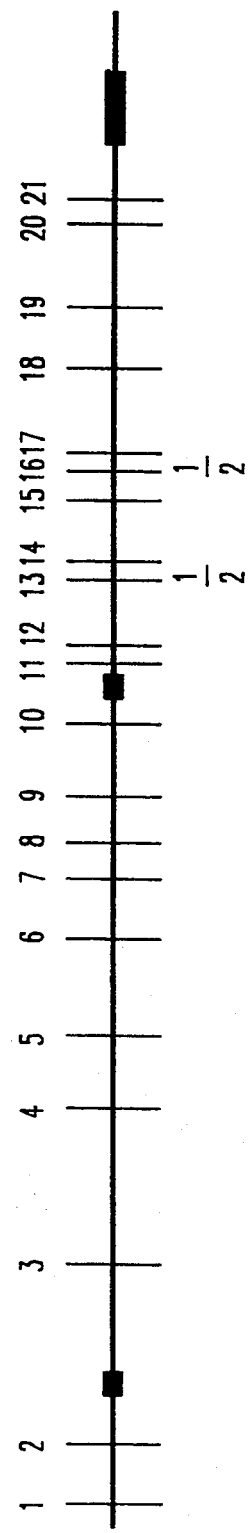
Figure 13B:
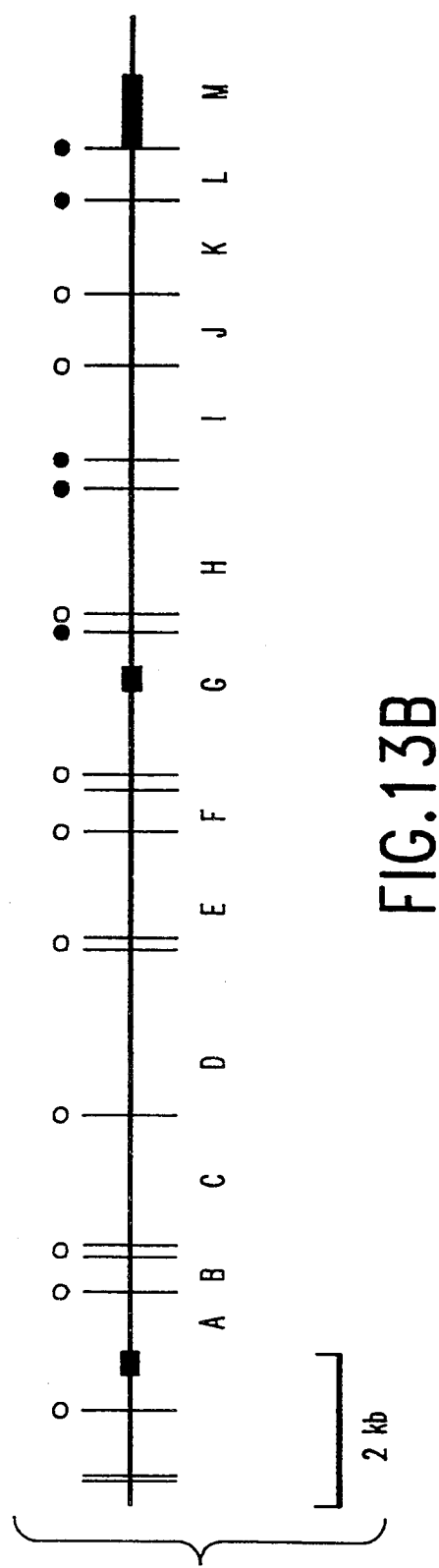

FIGS. 13(A and B). Location of the Alu Elements and the HpaII/MspI Sites in the Human Serglycin Gene. FIG. 13A: the locations of the 21 Alu elements in the 5'-flanking region, intron 1, and intron 2 of the serglycin gene are depicted. The locations of the two Alu elements containing only the left arm are identified with ½. The three exons are boxed (■). FIG. 13B: the locations of the HpaII/MspI sites (5'-CCGG-3') in the serglycin gene are indicated by the vertical lines. The letters depict the location of the probes used to determine the extent of methylation of these sites. Sites in the serglycin gene in HL-60 cells that are at least partially methylated are indicated by closed circles, and nonmethylated sites are indicated by open circles.

DETAILED DESCRIPTION OF THE PREFERRED EMBODIMENTS

I. Definitions

In the description that follows, a number of terms used in recombinant DNA (rDNA) technology are extensively utilized. In order to provide a clear and consistent understanding of the specification and claims, including the scope to be given such terms, the following definitions are provided.

Gene

A DNA sequence containing a template for a RNA polymerase. The RNA transcribed from a gene may or may not code for a protein. RNA that codes for a protein is termed messenger RNA (mRNA) and, in eukaryotes, is transcribed by RNA polymerase II. However, it is also known to construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA." Antisense RNAs are not normally translatable due to the presence of translational stop codons in the antisense RNA sequence.

A "complementary DNA" or "cDNA" gene includes recombinant genes synthesized by reverse transcription of mRNA and from which intervening sequences (introns) have been removed.

Cloning Vehicle

A plasmid or phage DNA or other DNA sequence which is able to replicate autonomously in a host cell, and that is characterized by one or a small number of endonuclease recognition sites at which such DNA sequences may be cut in a determinable fashion without loss of an essential biological function of the vehicle, and into which DNA may be spliced in order to bring about its replication and cloning. The cloning vehicle may further contain a marker suitable for use in the identification of cells transformed with the cloning vehicle. Markers, for example, are tetracycline resistance or ampicillin resistance. The word "vector" is sometimes used for "cloning vehicle."

Expression Vehicle

A vehicle or vector similar to a cloning vehicle but which is capable of expressing a gene that has been cloned into it, after transformation into a host. Accordingly to the invention, the cloned gene or coding sequence (the gene of interest) is usually placed under the control of (i.e., operably linked to) certain control sequences such as the promoter sequences and/or regulatory elements of the invention. Expression control sequences will vary and may additionally contain transcriptional elements such as enhancer elements, termination sequences, tissue-specificity elements in addition to those of the invention, and/or translational initiation and termination sites.

Proteoglycan

This term as used throughout the specification and claims means mammalian and especially human "hematopoietic cell proteoglycan" that contains glycosaminoglycan chains covalently bound to the proteoglycan's core protein.

Serglycin

Serglycin is the peptide core of hematopoietic cell secretory granule proteoglycan. The term is meant to include peptide fragments of hematopoietic cell secretory granule proteoglycan wherein the peptide core protein contains less than the naturally-occurring number of amino acids, but which retains biological (functional or structural) activity. Example of the functional activity serglycin is the ability to induce a specific biological response in the same manner that the native non-recombinant protein does, such as the ability to be conjugated into a specific proteoglycan form. An example of a structural activity is the ability to bind antibodies which also recognize the native non-recombinant protein.

The term is also used to include serglycin fusion proteins, that is, a peptide which comprises the sequence of a naturally-occurring serglycin or a biologically active fragment thereof together with one or more additional flanking amino acids, but which still possesses hematopoietic cell secretory granule proteoglycan biological (functional or structural) activity.

Transcriptional Regulatory Element

A transcriptional regulatory element (or DNA regulatory element) is a DNA sequence that, when operably linked to a gene of interest, is capable of altering the transcription of such gene of interest in a specific way characteristic of such element. Transcriptional regulatory elements include promoters, enhancers, suppressors, transcriptional start sites, transcriptional stop sites, polyadenylation sites, and the like.

Functional Derivative

A "functional derivative" of the DNA regulatory elements of the invention is a DNA sequence that possesses a least a biologically active fragment of the sequence of the regulatory elements of the invention; by "biologically active" fragment is meant that the fragment retain a biological activity (either functional or structural) that is substantially similar to a biological activity of the full-length DNA element. A biological activity of a DNA regulatory element of the invention is its ability to alter transcription in a manner known to be attributed to the full-length element. Hence, biologically active fragments of the suppressor element of the invention will retain the ability to inhibit or repress transcription; biologically active fragments of the enhancer element of the invention will retain the ability to stimulate transcription; and biologically active fragments of the promoter sequence of the invention will retain the ability to promote transcription.

The term "functional derivative" is intended to include the "fragments," "variants," "analogues," or "chemical derivatives" of a molecule.

Fragment

A "fragment" of a nucleotide or peptide sequence is meant to refer to a sequence that is less than that believed to be the "full-length" sequence.

Variant

A "variant" of a molecule is meant to refer to allelic variations of such sequences, that is, a sequence substantially similar in structure and biological activity to either the entire molecule, or to a fragment thereof.

II. Genetic Engineering of the Regulatory Elements of the Invention

Provided herein are transcriptional cis-acting elements of hematopoietic cells: an enhancer element, a suppressor element and a novel promoter element. The transcriptional cis-acting elements of the invention are naturally found in the 5' regulatory region of the serglycin gene. In addition, provided herein are trans-acting factors, such factors specifically binding to the cis-acting elements of the invention. The process for genetically engineering the genetic regulatory elements of the invention, or the trans-acting factors of the invention, is facilitated through the cloning of genetic sequences that contain the sequence for such regulatory elements or factors. The 333 base pair (bp) nucleotide sequence 5' of the transcription-initiation site of the mouse gene is nearly identical to the corresponding region of the human gene (Nicodemus et al., J. Biol. Chem. 265:5889–5896 (1990)). Thus, the mouse or human sequence may be used interchangeably for the cloning of the alternate species, or the cloning of similar sequences in other species.

The regulatory elements may be cloned directly, using, for example, promoter probe vectors and the like. For the identification of those regions of the serglycin gene that provide the cis-acting enhancer, suppressor, and/or promoter, rat basophilic leukemia-1 cells, mouse WEHI-3 cells, rat-1 fibroblasts, and mouse 3T3 fibroblasts may be transiently transfected with plasmid constructs containing various lengths of the 504-bp 5' flanking region of the mouse serglycin gene linked to a gene of interest, for example, the human growth hormone (hGH) gene, so as to provide a reporter, expression of which indicates transcriptional activity. Rat basophilic leukemia-1 cells and mouse WEHI-3 cells are preferred because they contain cytoplasmic granules and express large amounts of serglycin, whereas no serglycin transcript is present in either fibroblast line (Tantravahi et al., Proc. Natl. Acad. Sci. USA 83:9207–9210 (1986)).

The hGH transient expression system is preferred because it is at least 10-fold more sensitive than the CAT system (Selden et al., Mol. Cell Biol. 6:3173–3179 (1986)) or other systems that are based on the expression of $\beta$-galactosidase (An et al., Mol. Cell. Biol. 2:1628–1632 (1982)) and xanthine-guanine phosphoribosyl transferase (Chu et al., Nucleic Acids Res. 13:2921–2930 (1985)). This increased sensitivity enables hGH levels to be measured after transfection with a very small amount of plasmid, thus avoiding potential problems of competition (Selden et al., Mol. Cell Biol. 6:3173–3179 (1986)). The hGH transient expression system is well-suited for use because the plasmids are known in the art (such as pXGH5 for example) that can be used as an internal positive control for normalizing the efficiency of transfection, thereby facilitating the interpretation of data from separate experiments.

The specificity of the transcriptional regulatory elements of the invention is such that reporter mRNA expression using the transcriptional regulatory elements of the invention may be detected in rat-1 fibroblasts transfected with appropriate promoter probe plasmids that contain the desired regulatory elements operably linked to the reporter gene. For example, construct pPG(−118/+24)hGH, containing the promoter and enhancer element of the invention will provide high levels of reporter expression in such host cells.

In addition, high levels of reporter expression will be detected in rat basophilic leukemia-1 cells transfected with constructs containing the suppressor, enhancer, and promoter of the invention, (for example, pPG(−504/+24)hGH) or just the enhancer and promoter of the invention (for example pPG(−118/+24)hGH).

In contrast, lesser amounts reporter mRNA will be detected in rat basophilic leukemia-1 cells and rat-1 fibroblasts transfected with promoter probe vectors containing only the promoter of the invention (for example, pPG(−40/+24)hGH). No reporter mRNA will be detected in rat basophilic leukemia-1 cells transfected with pΦGH or in rat-1 fibroblasts transfected with constructs containing the suppressor, enhancer and promoter of the invention (for example pPG(−504/+24)hGH) or pΦGH. Because large amounts of hGH are detected in the culture media of rat basophilic leukemia-1 cells and rat-1 fibroblasts that contain abundant levels of hGH mRNA and because lesser amounts of hGH are detected in the culture media of cells containing intermediate levels of hGH mRNA, transcription and translation of the hGH gene are related in both transfected cell types.

The results of the transfections should be normalized to that obtained with a reference plasmid, such as, for the growth hormone reporter, pXGH5. Rat basophilic leukemia-1 cells produce more reporter (18-fold more hGH) than transfected rat-1 fibroblasts. Likewise, mouse WEHI-3 cells produce more reporter than transfected mouse 3T3 fibroblasts (pPG(−504/+24)hGH produced 20-fold more hGH in mouse WEHI-3 cells than transfected mouse 3T3 fibroblasts).

Based on the results such as those discussed above and herein, the presence of cis-acting regulatory elements the 5′ flanking region of a gene, and/or in the first intron of such gene, and especially of the serglycin gene, may be established. Such serglycin gene elements preferentially enhance the constitutive transcription of a gene of interest in hematopoietic cells or preferentially suppress transcription of a gene of interest in fibroblasts, although small differences may be present, due to other factors.

The sequences of intron 1 of the serglycin gene may act in concert to regulate transcription of a gene that is operably linked to the serglycin gene promoter in different cell types. When it is desired to utilize this concerted action, intron 1 sequences of the serglycin gene may be inserted into the coding sequence of a gene of interest such that what becomes exon 1 has approximately the same size as exon 1 of serglycin, and in a manner such that the reading frame of the coding sequence is not altered, and the normal recognition sequences at the flanking regions of the intron are provided, so as to allow subsequent excision of the intron.

To locate the cis-acting elements of the invention more precisely, additional plasmid constructs may be prepared that contain progressively less of the 5′ flanking region of the serglycin gene. For example, the transfection of rat basophilic leukemia-1 cells and rat-1 fibroblasts with these shortened constructs of the 5′ flanking region of the mouse serglycin gene reveal that a cis-acting element resides between residues −250 and −190 and suppresses transcription of this gene, and that this suppressor element is more dominantly active in rat-1 fibroblasts than in rat basophilic leukemia-1 cells.

In a similar manner, such experiments revealed that an enhancer element resides between residues −118 and −81 of the mouse serglycin gene that not only appears to be important for the positive constitutive transcription of this gene but also is dominantly active in rat basophilic leukemia-1 cells.

Rat basophilic leukemia-1 cells and fibroblasts produce substantially more reporter protein when transfected with a construct containing the enhancer and promoter of the invention (for example, pPG(−118/−44)-SV40-hGH) than with a control that provides a foreign element (for example pSV40-hGH). Typical of other enhancers, the enhancer activity of the enhancer of the invention is not diminished by changing its orientation and its distance from the SV40 early promoter in the plasmid.

The promoter element of the invention is a unique sequence that provides an alternate to the classical TATA box. For most genes, transcription is initiated −30 bp downstream of the proximal end of the promoter, which usually is a TATA box. Because no reporter protein is detected when rat basophilic leukemia-1 cells and rat-1 fibroblasts are transfected with constructs containing only 20 nucleotides of the proximal end of the serglycin gene, (pPG(−20/+24)hGH), but some reporter protein is produced by cells transfected with constructs containing at least 40 nucleotides (pPG(−40/+24)hGH), the proximal element of the promoter of the invention resides between residues −40 and −20. Inasmuch as no TATA box is present in this region (Avraham et al., J. Biol. Chem. 264:16719–16726 (1989); Nicodemus et al., J. Biol. Chem. 265:5889–5896 (1990)), the TCTAAAA sequence at residues −31 to −25 may serve as an alternative element.

To demonstrate the important residues of the elements of the invention, they may be mutated, using techniques known in the art. For example, to demonstrate the important residues of the promoter element of the invention, residues −28, −30, or −38 were mutated. Based on the relative amount of reporter produced in the transfected cells, it was shown that the 5′ flanking region containing the TCTAAAA sequence functions as a TATA box equivalent.

Alternatively to using promoter probe vectors for the cloning of the regulatory elements of the invention, the coding sequence of the serglycin gene (previously called the secretory granule proteoglycan peptide core protein) may be cloned and used to identify clones or DNA containing the desired regulatory elements operably linked to the cloned coding sequence. The discussion below, while it specifically refers to cloning of the serglycin gene, may also be adapted by those of skill in the art for the cloning of the trans-acting factors of the invention.

The regulatory elements of the genomic DNA of the invention may be obtained in association with the 5′ promoter region of the serglycin gene. For example, when rat-1 fibroblasts were stably transfected with the mouse genomic clone, λ-MG-PG1, two cell lines were obtained that expressed low levels of the 1.0-kb serglycin mRNA (Avraham et al., J. Biol. Chem. 264:16719–16726 (1989)). This finding indicated that λ-MG-PG 1 contained the entire mouse serglycin gene, including, perhaps, some of the regulatory elements within its promoter region. S1 nuclease mapping and primer extension analysis revealed that the primary transcription-initiation site for this gene in mouse bone marrow-derived mast cells (BMC) resides ∼40 nucleotides upstream of the translation-initiation site (Avraham et al., J. Biol. Chem. 264:16719-16726 (1989)).

As used herein, the term "genetic sequences" is intended to refer to a nucleic acid molecule (preferably DNA). Genetic sequences that are capable of providing the regulatory elements of the invention are derived from a variety of sources, including genomic DNA, synthetic DNA, and combinations thereof. Genetic sequences that are capable of encoding serglycin may further be derived from mRNA or cDNA.

Genomic DNA containing the serglycin gene can be extracted and purified from any eukaryotic and especially mammalian cell that has this gene in its genome by means well known in the art (for example, see Guide to Molecular Cloning Techniques, S. L. Berger et al., eds., Academic Press (1987)).

Serglycin mRNA can be isolated from any cell which produces or expresses this protein. Serglycin mRNA can also be used to produce cDNA by means well known in the art (for example, see Guide to Molecular Cloning Techniques, S. L. Berger et al., eds., Academic Press (1987)). Such cell sources include, but are not limited to, fresh cell preparations and cultured cell lines, especially fresh or cultured connective tissue mast cells, mucosal mast cells, basophils, natural killer cells, cytotoxic T lymphocytes, eosinophils, neutrophils, macrophages and platelets.

Preferably, the mRNA preparation used will be enriched in mRNA coding for serglycin, either naturally, by isolation from a cells which are producing large amounts of the protein, or in vitro, by techniques commonly used to enrich mRNA preparations for specific sequences, such as sucrose gradient centrifugation, or both.

For cloning into a vector, suitable DNA preparations (genomic DNA containing the regulatory elements of the invention or cDNA encoding the serglycin) are randomly sheared or enzymatically cleaved, respectively, and ligated into appropriate vectors to form a recombinant gene (either genomic or cDNA) library.

A DNA sequence providing the regulatory elements of the invention, or the serglycin coding sequence, may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well known in the art.

A serglycin clone may be identified by any means which specifically selects for serglycin DNA such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated serglycin protein product produced by the host containing the clone. The ability to specifically bind antibody against serglycin or its proteoglycan, the ability to elicit the production of antibody capable of binding to serglycin as its proteoglycan, and/or the ability to provide a serglycin proteoglycan-associated function to a recipient cell, are all examples of the biological properties of the serglycin proteoglycan.

Oligonucleotide probes specific for the serglycin gene are useful for the identification of genomic or cDNA clones to this protein, or useful for the identification of clones to the regulatory elements of the invention, can be designed from knowledge of the amino acid sequence of the protein's peptide core, or from knowledge of the nucleotide sequence of the regulatory element, respectfully.

When designing a probe against a peptide sequence, the sequence of amino acid residues in a peptide is designated herein either through the use of their commonly employed three-letter designations or by their single-letter designations. A listing of these three-letter and one-letter designations may be found in textbooks such as Biochemistry, Lehninger, A., Worth Publishers, New York, N.Y. (1970). When the amino acid sequence is listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence.

When designing probes against a peptide sequence, because the genetic code is degenerate, more than one codon may be used to encode a particular amino acid (Watson, J. D., In: Molecular Biology of the Gene, 3rd Ed., W. A. Benjamin, Inc., Menlo Park, Calif. (1977), pp. 356-357). The peptide fragments are analyzed to identify sequences of amino acids that may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences that are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., In: Molecular Biology of the Gene, 3rd Ed., W. A. Benjamin, Inc., Menlo Park, Calif. (1977)), one or more different polynucleotides or oligonucleotides can be identified from the amino acid sequence, each of which would be capable of encoding the serglycin protein or fragments thereof. The probability that a particular polynucleotide will, in fact, constitute the actual serglycin encoding sequence can be estimated by considering abnormal base pairing relationships and the frequency with which a particular codon is actually used (to encode a particular amino acid) in eukaryotic cells. Such "codon usage rules" are disclosed by Lathe, R., et al., J. Molec. Biol. 183:1-12 (1985). Using the "codon usage rules" of Lathe, a single polynucleotide sequence, or a set of polynucleotide sequences, that contain a theoretical "most probable" nucleotide sequence capable of encoding the serglycin sequences is identified.

The suitable polynucleotide, or set of polynucleotides, that is capable of encoding the serglycin gene, or fragment thereof, may be synthesized by means well known in the art (see, for example, Synthesis and Application of DNA and RNA, S. A. Narang, ed., 1987, Academic Press, San Diego, Calif.) and employed as a probe to identify and isolate the cloned serglycin gene by techniques known in the art. Techniques of nucleic acid hybridization and clone identification are disclosed by Maniatis, T., et al., (In: Molecular Cloning A Laboratory Manual, Cold Spring Harbor Laboratories, Cold Spring Harbor, N.Y. (1982)), and by Hames, B. D., et al., (In: Nucleic Acid Hybridization, A Practical Approach, IRL Press, Wash., DC (1985)), which references are herein incorporated by reference. Those members of the above-described gene library that are found to be capable of such hybridization are then analyzed to determine the extent and nature of the serglycin encoding sequences that they contain.

To facilitate the detection of the desired serglycin DNA encoding sequence, the above-described DNA probe may be labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., J. Mol. Biol. 113:237 (1977) and by T4 DNA polymerase replacement synthesis as described in, for example, Deen, K. C., et al., Anal. Biochem. 135:456 (1983).

Alternatively, polynucleotides are also useful as nucleic acid hybridization probes when labeled with a non-radioactive marker such as biotin, an enzyme or a fluorescent group. See, for example, Leary, J. J., et al., Proc. Natl. Acad. Sci. USA 80:4045 (1983); Renz, M., et al., Nucl. Acids Res. 12:3435 (1984); and Renz, M., EMBO J. 6:817 (1983).

Thus, in summary, the actual identification of the amino acid sequence of serglycin permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the serglycin gene, and thus the regulatory elements of the invention.

In an alternative way of cloning the serglycin gene, a library is prepared using an expression vector, by cloning DNA prepared from a cell possessing, and preferably, capable of expressing, serglycin, into an expression vector. The cDNA library is then screened for members that express serglycin, for example, by screening the library with antibodies to the protein, such as the antibody depicted in FIG. 6.

In another embodiment, a previously described rat L2 cell-derived cDNA of a related proteoglycan, pPG-1, (disclosed in Bourdon et al., Proc. Natl. Acad. Sci. USA 82:1322 (1985))is used to identify a sequence encoding serglycin. For example, Southern blots of digested genomic DNA may be probed with nick-translated pPG-1 or pPG-M (a gene specific 489 bp Ssp I→3'end fragment of pPG-1), Tantravahi et al., Proc. Natl. Acad. Sci. USA 83:9207 (1986), under reduced stringency if necessary, to allow for mismatch between the sequence expressed in the different species.

The above discussed methods are, therefore, capable of identifying genetic sequences that are capable of encoding the serglycin or fragments of this protein. Such coding sequences may then be used to identify clones containing the transcriptional regulatory elements of the invention.

For example, using the techniques described above, a number of DNA fragments were identified when a human genomic DNA blot was probed under conditions of low stringency with a rat serglycin cDNA (Stevens et al., J. Biol. Chem. 263:7287 (1988)). Nevertheless, by probing a human promyelomonocytic HL-60 cell-derived cDNA library under conditions of low stringency with the rat cDNA, a cDNA was isolated and characterized that encodes human serglycin (Stevens et al., J. Biol. Chem. 263:7287 (1988)). Sequence analysis of a resulting cDNA clone indicated that in the human this proteoglycan peptide core is only 17.6 kDa and contains an 18 amino acid glycosaminoglycan attachment region consisting primarily of alternating serine and glycine. A single gene that resides on chromosome 10 encodes this human protein (Stevens et al., J. Biol. Chem. 263:7287 (1988); Nicodemus et al., J. Biol. Chem. 265:5889 (1990); Mattei et al., Human Genetics 82:87 (1989)). A human genomic library was probed under conditions of high stringency with a 5' fragment of the HL-60 cell cDNA to isolate two 18-kb genomic fragments that taken together contain the entire human serglycin gene (Nicodemus et al., J. Biol. Chem. 265:5889 (1990)). A restriction map of this human gene was constructed, and the genomic fragments subcloned into Bluescript ™ plasmid, and the nucleotide sequence of the entire 16.6 kb human gene determined plus 0.7 kb of 5' flanking DNA, using techniques known in the art.

In addition, a 1.0-kb cDNA that encodes mouse serglycin was isolated from a mouse bone marrow-derived mast cells-derived cDNA library. When the predicted amino acid sequences of the mouse, rat, and human serglycin were compared, the N-terminus (not the serine-glycine rich glycosaminoglycan-attachment region) was found to be the most conserved region. This surprising finding suggests that N terminus of the translated peptide core is important for the structure, function, and/or metabolism of this family of proteoglycans. Areas of identity in the 3' and 5' untranslated regions in the human, rat, and mouse proteoglycan cDNAs were also observed (Avraham et al., Proc. Natl. Acad. Sci. USA 86:3763 (1989)). Interestingly, these 3' and 5' conserved untranslated nucleotide sequences were almost identical in the corresponding regions of the cDNAs that encode human mast cell tryptase (Miller et al., J. Clin. Invest. 84:1188 (1989)), dog mast cell tryptase (Vanderslice et al., Biochemistry 28:4148 (1989)), mouse mast cell protease-2 (Serafin et al., J. Biol. Chem. 265:423 (1990)), and rat mast cell protease-II (Benfey et al., J. Biol. Chem. 262:5377 (1987)), suggesting that these nucleotide sequences may be important for coordinated regulation of those genes that encode proteins destined to reside in the secretory granules of hematopoietic cells.

To isolate the mouse serglycin gene, a mouse genomic DNA library was probed under conditions of high stringency with a 3' gene specific fragment of the mouse bone marrow-derived mast cells-derived cDNA. An ~18 kb genomic clone (kMG-PG1) which contains the entire gene that encodes mouse serglycin was isolated. The exon/intron organization of the mouse gene was determined, as well as the transcription-initiation site and the 504-bp nucleotide sequence that is upstream of the gene.

Typically, transcription is initiated ~30 bp downstream of an element within the proximal end of a gene's promoter (defined in this case as the smallest amount of nucleotide sequence that must be present to get minimal transcription of a gene in a cell). In most eukaryotic genes, their promoters contain either a TATA box (Breathnach et al., Ann. Rev. Biochem. 50:349 (1981)) or a GC-rich element (Sehgal et al., Mol. Cell Biol. 8:3160 (1988)). In rarer cases, such as the terminal deoxynucleotidyltransferase gene (Smale, S. T., and Baltimore, D. (1989) Cell 57:103 (1988)), a third type of promoter region is present which lacks these specific transcription-initiation control sequences.

The mouse serglycin gene does not contain either a classical TATA box or a GC-rich element ~30 bp upstream of the transcription-initiation site. Therefore, its promoter appears to belong to the rarer, third class of promoters.

Accordingly, the above discussed methods are also capable of directly identifying clones containing genetic sequences containing the transcriptional regulatory elements of the invention.

The above discussed methods are also capable of being adapted for the identification of clones directed to the trans-acting factors of the invention. Especially, clones capable of expressing such trans-acting factors may be identified utilizing the target sequence to which they bind (in a double-stranded DNA form) to detect their presence in protein-DNA binding assays. Such assays are well known in the art.

In order to further characterize such genetic sequences, and, in order to produce recombinant protein under the transcriptional control of such sequences, such transcriptional regulatory elements must be provided to an appropriate host.

III. Expression of Proteins Operably-linked to the Transcriptional Regulatory Elements of the Invention As used herein, "heterologous protein" is intended to refer to a peptide sequence that is heterologous to the transcriptional regulatory elements of the invention. A skilled artisan will recognize that, if desired, the teaching herein will also apply to the expression of genetic sequences encoding serglycin homologous to such regulatory elements.

To express a heterologous protein under the control of the transcriptional regulatory elements of the invention, the heterologous protein must be "operably-linked" to the regulatory element. An operable linkage is a linkage in which a desired sequence is connected to a transcriptional or translational regulatory sequence (or sequences) in such a way as to place expression (or operation) of the desired sequence under the influence or control of the regulatory sequence.

Two DNA sequences (such as a sequence encoding a heterologous protein and a promoter region sequence linked to the 5' end of the encoding sequence) are said to be operably linked if induction of promoter function results in the transcription of the DNA encoding the heterologous protein and if the nature of the linkage between the two DNA sequences does not (1) result in the introduction of a frame-shift mutation, (2)interfere with the ability of the expression regulatory sequences to direct the expression of the heterologous protein DNA, or (3) interfere with the ability of the heterologous protein template to be transcribed by the promoter region sequence. Thus, a promoter region would be operably linked to a DNA sequence if the promoter were capable of effecting transcription of that DNA sequence.

In a similar manner, a transcriptional regulatory element that stimulated or repressed promoter function may be operably-linked to such promoter. Exact placement of the element in the nucleotide chain is not critical as long as the element is located at a position from which the desired effects on the operably linked promoter may be revealed. A nucleic acid molecule, such as DNA, is said to be "capable of expressing" a polypeptide if it contains expression control sequences which contain transcriptional regulatory information and such sequences are operably linked to the nucleotide sequence which encodes the polypeptide.

For the complete control of heterologous gene expression, all transcriptional and translational regulatory elements (or signals) that are operably linked to a heterologous gene should be recognizable by the appropriate host. By "recognizable" in a host is meant that such signals are functional in such host.

The cloned transcriptional regulatory elements, obtained through the methods described above, and preferably in a double-stranded form, may be operably linked to a heterologous gene, preferably in an expression vector, and introduced into a host cell, preferably eukaryote cell, and most preferably, a eukaryotic cell of the hematopoietic cell origin, to produce recombinant heterologous protein.

Expression of the heterologous protein in different hosts may result in different post-translational modifications that may or may not alter the properties of the heterologous protein. Especially preferred hosts are cells either in vivo, or in tissue culture that provide post-translational modifications to the heterologous protein that include folding and/or glycosylation at sites similar or identical to that found for the native proteoglycan.

Appropriate cells of hematopoietic cell origin include, for example, hematopoietic cells that participate in immune and inflammatory responses, including connective tissue mast cells, mucosal mast cells, basophils, natural killer cells, cytotoxic T lymphocytes, eosinophils, neutrophils, macrophages, and platelets. For example, rat basophilic leukemia-1 cells (ATCC CRL-1378), mouse bone marrow derived mast cells, mouse mast cells immortalized with Kirsten sarcoma virus, normal mouse mast cells that have been co-cultured with mouse fibroblasts, or mouse myelomonocytic WEHI-3 cells (ATCC TIB-68) are useful. Razin et al., J. Immun. 132:1479 (1984); Levi-Schaffer et al., Proc. Natl. Acad. Sci. (USA) 83:6485 (1986)and Reynolds et al., "Immortalization of Murine Connective Tissue-type Mast Cells at Multiple Stages of Their Differentiation by Coculture of Splenocytes with Fibroblasts that Produce Kirsten Sarcoma Virus," J. Biol. Chem. 263:12783–12791 (1988). See Example 5, below. Methods for the long term in vitro proliferation of pluripotent bone marrow stem cells are known (Handbook of the Hematopoietic Microenvironment, M. Tavassoli, ed., Humana Press, Inc., Clifton, N.J. 1989).

The precise nature of the regulator), regions needed for gene expression may vary between species or cell types, but shall in general include, as necessary, 5' non-transcribing and 5' non-translating (non-coding) sequences involved with initiation of transcription and translation respectively. Especially, at a minimum, such 5' non-transcribing control sequences will include a region which contains a promoter for transcriptional control of the operably linked gene.

The promoter preferably is the serglycin gene promoter of the invention. However, the enhancer and suppressor transcriptional regulatory elements of the invention may be operably linked to any promoter that is function in the desired host cell. A wide variety of transcriptional and translational regulatory sequences can be employed, operably linked to a transcriptional regulatory element of the invention, depending upon the nature of the eukaryotic host. In eukaryotes, where transcription is not linked to translation, such control regions may or may not provide an initiator methionine (AUG) codon, depending on whether the operably linked heterologous sequence contains such a methionine. Such regions will, in general, include a promoter region sufficient to direct the initiation of RNA synthesis in the host cell. Promoters from heterologous mammalian genes that encode an mRNA product capable of translation are preferred, and especially, strong promoters such as the promoter for actin, collagen, myosin, etc., can be employed provided they also function as promoters in the host cell, and provided that their function is also capable of being control by the desired positive or suppressor of the invention.

As is widely known, translation of eukaryotic mRNA is initiated at the codon that encodes the first methionine. For this reason, it is preferable to ensure that the linkage between a eukaryotic promoter and a DNA sequence that encodes the heterologous protein does not contain any intervening codons that are capable of encoding a methionine. The presence of such codons results either in a formation of a fusion protein (if the AUG codon is in the same reading frame as the DNA encoding the heterologous protein) or a frame-shift mutation (if the AUG codon is not in the same reading frame as the DNA encoding the heterologous protein.

If desired, a fusion product of the heterologous protein may be constructed. For example, the sequence coding for the heterologous protein may be linked to a signal sequence which will allow secretion of the protein from, or the compartmentalization of the protein in, a particular host. Such signal sequences may be designed with or without specific protease sites such that the signal peptide sequence is amenable to subsequent removal. Alternatively, the native signal sequence for this protein may be used.

The transcriptional initiation regulatory elements of the invention can be selected to allow for repression or activation, so that expression of the operably linked genes can be modulated. Translational signals are not necessary when it is desired to express antisense RNA sequences.

If desired, the non-transcribed and/or non-translated regions 3' to the sequence coding for the heterologous protein can be obtained by the above-described cloning methods. The 3'-non-transcribed region may be retained for its transcriptional termination regulatory sequence elements; the 3-non-translated region may be retained for its translational termination regulatory sequence elements, or for those elements that direct polyadenylation in eukaryotic cells. Where the native expression control sequences signals do not function satisfactorily host cell, then sequences functional in the host cell may be substituted.

To transform a mammalian cell with the DNA constructs of the invention many vector systems are available, depending upon whether it is desired to insert the heterologous protein DNA construct into the host cell chromosomal DNA, or to allow it to exist in an extrachromosomal form.

If the heterologous protein's DNA sequence and an operably linked promoter is introduced into a recipient eukaryotic cell as a non-replicating DNA (or RNA) molecule which may either be a linear molecule or, more preferably, a closed covalent circular molecule that is incapable of autonomous replication, the expression of the heterologous protein may occur through the transient expression of the introduced sequence.

Genetically stable transformants may be constructed with vector systems, or transformation systems, whereby the heterologous protein's DNA is integrated into the host chromosome. Such integration may occur de novo within the cell or, in a most preferred embodiment, be assisted by transformation with a vector that functionally inserts itself into the host chromosome. Vectors capable of chromosomal insertion include, for example, retroviral vectors, transposons or other DNA elements which promote integration of DNA sequences in chromosomes, especially DNA sequence homologous to a desired chromosomal insertion site.

Cells that have stably integrated the introduced DNA into their chromosomes are selected by also introducing one or more markers that allow for selection of host cells which that the desired sequence. For example, the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, and SV40. Such plasmids are well known in the art and are commonly or commercially available. For example, mammalian expression vector systems in which it is possible to cotransfect with a helper virus to amplify plasmid copy number, and, integrate the plasmid into the chromosomes of host cells have been described (Perkins, A. S. et al., Mol. Cell Biol. 3:1123 (1983); Clontech, Palo Alto, Calif.).

Once the vector or DNA sequence containing the construct(s) is prepared for expression, the DNA construct(s) is introduced into an appropriate host cell by any of a variety of suitable means, including transfection, electroporation or delivery by liposomes. DEAE-dextran, or calcium phosphate, may be useful in the transfection protocol.

After the introduction of the vector in vitro, recipient cells are grown in a selective medium, that is, medium that selects for the growth of vector-containing cells. Expression of the cloned gene sequence(s) results in the production of the heterologous protein.

According to the invention, this expression can take place in a continuous manner in the transformed cells, or in a controlled manner.

If desired, in in vitro culture, the expressed protein is isolated and purified in accordance with conventional conditions, such as extraction, precipitation, chromatography, affinity chromatography, electrophoresis, or the like.

The vectors obtained through the methods above, will provide sequences that, by definition, provide a transcriptional regulatory element of the invention (the serglycin promoter, and/or the enhancer element and/or the suppressor element). Such vectors may be designed with restriction enzyme sites that allow for the insertion of a DNA sequence encoding a heterologous protein at a site or sites operably linked to the transcriptional regulatory complex (the promoter and any additional elements that alter promoter function).

Using the techniques described above, cotransfection of rat fibroblasts with λMG-PG1 and the selectable marker pSV2 neo resulted in the establishment of fibroblast cell lines that had integrated both foreign genes into their genome (Avraham et al., J. Biol. Chem. 264:16719 (1989)). RNA blot analysis revealed that two of the rat fibroblast cell lines contained low, but detectable, levels of the 1.0-kb mRNA transcript that encodes mouse serglycin. No other gene that encodes a proteoglycan peptide core has been isolated and sequenced in its entirety. Neither has one been inserted into a foreign cell.

The ability of the transfected rat fibroblasts to transcribe the foreign mouse gene indicates that some of the regulatory elements in the gene's promoter are present in the isolated mouse genomic clone. When the 504-bp 5' flanking region of the mouse serglycin gene was compared to the corresponding 5' flanking region of the analogous human gene, a 119-bp region that immediately precedes the transcription-initiation site was found to be nearly identical. This nucleotide sequence is more highly conserved in evolution than any similar sized region of the gene that is translated into protein.

The 504-bp 5' flanking region of the mouse serglycin gene was linked to plasmid DNA that contains the structural sequences of the human growth hormone reporter gene, and the amount of growth hormone produced by different cell types transfected with the resulting plasmid construct quantified. With deletion analysis and site-directed mutagenesis, three motifs in the 5' flanking region of the mouse serglycin gene were identified that regulate its constitutive transcription. One of these elements suppressed transcription of the gene, whereas the other two elements enhanced its transcription. Due to the near identity of this 5' flanking region in the two species, it is likely the same cis-acting elements are used by all mouse and human cells that express this proteoglycan. As indicated by gel-mobility-shift assays, hematopoietic cells that transcribe the serglycin gene possess trans-acting factors in their nuclei that recognize these elements, and a different profile of trans-acting factors is present in fibroblasts that do not express the serglycin gene.

Using the enhancer that resides between nucleotide residues $-118$ and $-81$ as an enhancer, more growth hormone was produced in transiently-transfected cells than with control plasmid DNA containing a generic promoter. Because this cis-acting motif is one of the most potent enhancers now known for hematopoietic cells, it can be used as an effective tool to drive transcription (and thereby translation) of any foreign gene in hematopoietic cells.

IV. Characterization of the Trans-Acting Factors

Transcription is regulated by trans-acting factors that bind to distinct cis-acting elements usually located in the 5' flanking regions of genes, and these DNA-binding proteins can act in synergy to enhance transcription or in an opposing manner to suppress transcription. As assessed by gel mobility shift assays, rat basophilic leukemia-1 cells and rat-1 fibroblasts contain a number of DNA-binding proteins in their nuclei that specifically bind the region of DNA that contains the serglycin suppressor cis-acting element, the serglycin enhancer cis-acting element, and the proximal element of the serglycin promoter region. Based on their similar mobilities in the gel mobility shift assays, rat basophilic leukemia-1 cells and rat-1 fibroblasts contain a common trans-acting factor ($B/F_{(-250/-161)}$-I) that binds to the suppressor element and a common trans-acting factor ($B/F_{(-40/+24)}$-I) that binds to the proximal promoter. In addition, distinct trans-acting factors are present in each cell line. Rat-1 fibroblasts have distinct trans-acting factors that bind to the suppressor element ($F_{(-250/-161)}$-II), the enhancer element ($F_{(-118/-81)}$-I) and the proximal promoter ($F_{(-40/+24)}$-II), whereas rat basophilic leukemia-1 cells have distinct trans-acting factors that bind to the enhancer element ($B_{(-118/-81)}$-I) and the proximal promoter ($B_{(-40/+24)}$-II).

Stably transfected rat-1 fibroblasts that have incorporated 10-20 copies of the mouse genomic clone λ-MG-PG1 into their genome constitutively express low levels of the 1.0 kb serglycin transcript. Based on the transient transfections described herein, one reason normal fibroblasts contain no serglycin mRNA, and transfected fibroblasts contain only limited amounts, is due to the presence of the trans-acting factor of the invention in these mesenchymal cells, such trans-acting factor being very effective in suppressing transcription of this gene.

A computer search using the "Dynamics" program (Ghosh, D., Nucleic Acids Res. 18:1749–1756 (1990)) failed to reveal a conserved cis-acting element within residues $-250$ to $-118$ of the mouse and human serglycin gene that is recognized by a known suppressor DNA-binding protein, supporting the novelty of the cis-acting element present in this region of the serglycin gene. Because fibroblasts are more effective than rat basophilic leukemia-1 cells in their use of the element that resides between residues $-250$ and $-190$ to suppress transcription of the mouse serglycin gene, the responsible trans-acting factor may be more abundant, selectively expressed, or post-translationally modified to be more active. As assessed by the gel mobility shift assays with the residues $-250$ to $-161$ probe, the nuclear extracts of rat-1 fibroblasts contained at least one trans-acting factor that was not recognized in rat basophilic leukemia-1 cells.

V. Uses of the Invention

Although bacteria, yeast, and insect cells often can be transfected with foreign cDNAs or genes to obtain biologically-active recombinant proteins, in many situations it is necessary to express a protein in a mammalian cell so that it can be properly modified post-translationally. Some of the easiest cells to maintain in culture and to transfect with foreign DNA are immature hematopoietic cells such as rat basophilic leukemia-1 cells, mouse WEHI-3 monocytic cells, and mouse P815 mastocytoma cells. All three of these cell lines have their own spectrum of trans-acting DNA-binding proteins that bind to the cis-acting elements of those genes that the cells are programmed to express. Thus, in order to obtain maximal expression of a foreign gene in a transfected cell, one must use the regulatory elements of a gene that is expressed in abundance in that cell type. Serglycin mRNA is expressed in abundance in a large number of immature mouse, rat, and human hematopoietic cells that are easy to maintain in culture. The cis-acting elements of the invention, in the 5' flanking region of the mouse serglycin gene can, for the first time, be used be used to drive transcription and translation of a foreign gene in transfected rat basophilic leukemia cells and WEHI-3 monocytic cells.

Thus, the invention is useful for the expression of any protein in a mammalian, and especially a hematopoietic, cell system, especially any protein that requires the mammalian environment for post-translational modifications, including glycosylation. Proteins of interest that may be so expressed include hormones, such as insulin and growth hormone, other peptide growth factors, cytokines, interferons, interleukins, enzymes, structural proteins, albumin, actin, etc., and especially c-kit ligand, granulocyte-macrophage colony stimulating factor, interferon-γ, IL-1, IL-3, IL-4, IL-9, IL-10, nerve growth factor, and transforming growth factor-β.

Many varieties of transcriptional control may be provided to a heterologous gene by the regulatory elements of the invention. In a host cell of hematopoietic cell origin, for example, if a genetic sequence encoding the 5' flanking region of the serglycin gene (for example, the proximal 504 bp of the 5' flanking region) is operably linked to a heterologous gene, such genetic sequence may be expected to express in a manner, and to a degree similar to that of the native serglycin peptide gene.

Expression of a desired heterologous protein in a host cell of hematopoietic cell origin may be achieved by operably linking genetic sequences encoding the enhancer element of the invention to a desired promoter sequence functional in such host cell, such element being located between nucleotides −118 and −81 of the serglycin gene, and such element being dominantly active to stimulate transcription of operably linked genes in hematopoietic cells.

Expression of a desired heterologous protein in a host cell of hematopoietic cell origin may also be achieved by introducing genetic sequences encoding the unique and atypical eukaryotic promoter element operably linked to the coding sequence of the desired heterologous protein, such promoter element being located between nucleotides −40 and −20 of the serglycin gene, and such element being dominantly active for the promotion of transcription of operably linked genes in hematopoietic cells.

Expression in fibroblast hosts may be modified such that a desired gene that overexpresses an undesired protein in a fibroblast host may be "turned off" by introducing genetic sequences encoding the suppressor element of the invention, located between nucleotides −250 and −190 of the serglycin gene, on an integrating or vital vector that inserts such element into the transcriptional regulatory region of the gene.

For example, mast cell-derived glycosaminoglycans such as heparin and chondroitin sulfate di-B have potent biologic activities in different clinical situations. Unfortunately, prior to the invention, it has been difficult to obtain these glycosaminoglycans in sufficient quantity for analysis. Because of this problem, the biologic activities of mast cell-derived chondroitin sulfate E and chondroitin sulfate D have not even been tested. The ability to culture mast cells and, according to the invention, to alter the constituents of the mast cell's secretory granule using recombinant cytokines under the transcriptional control of the regulatory elements of the invention. Each cytokine or other desired factor may be examined for its ability to induce the polymerization of a specific type of glycosaminoglycan onto serglycin. Thus, mast cells may be induced to polymerize a specific type of glycosaminoglycan onto serglycin in response to specific recombinant cytokines, and, for the first time, the culture scaled up to obtain large amounts of the glycosaminoglycan of interest. Alternatively, using recombinant technology an animal may be genetically altered such that it can be induced to express large numbers of that particular mast cell that contains the desired glycosaminoglycan.

Having now generally described the invention, the same will become better understood by reference to certain specific examples which are included herein for purposes of illustration only and are not intended to be limiting unless other wise specified.

EXAMPLES

EXAMPLE 1

Construction and Screening of a HL-60 cDNA Library

Figure 1:
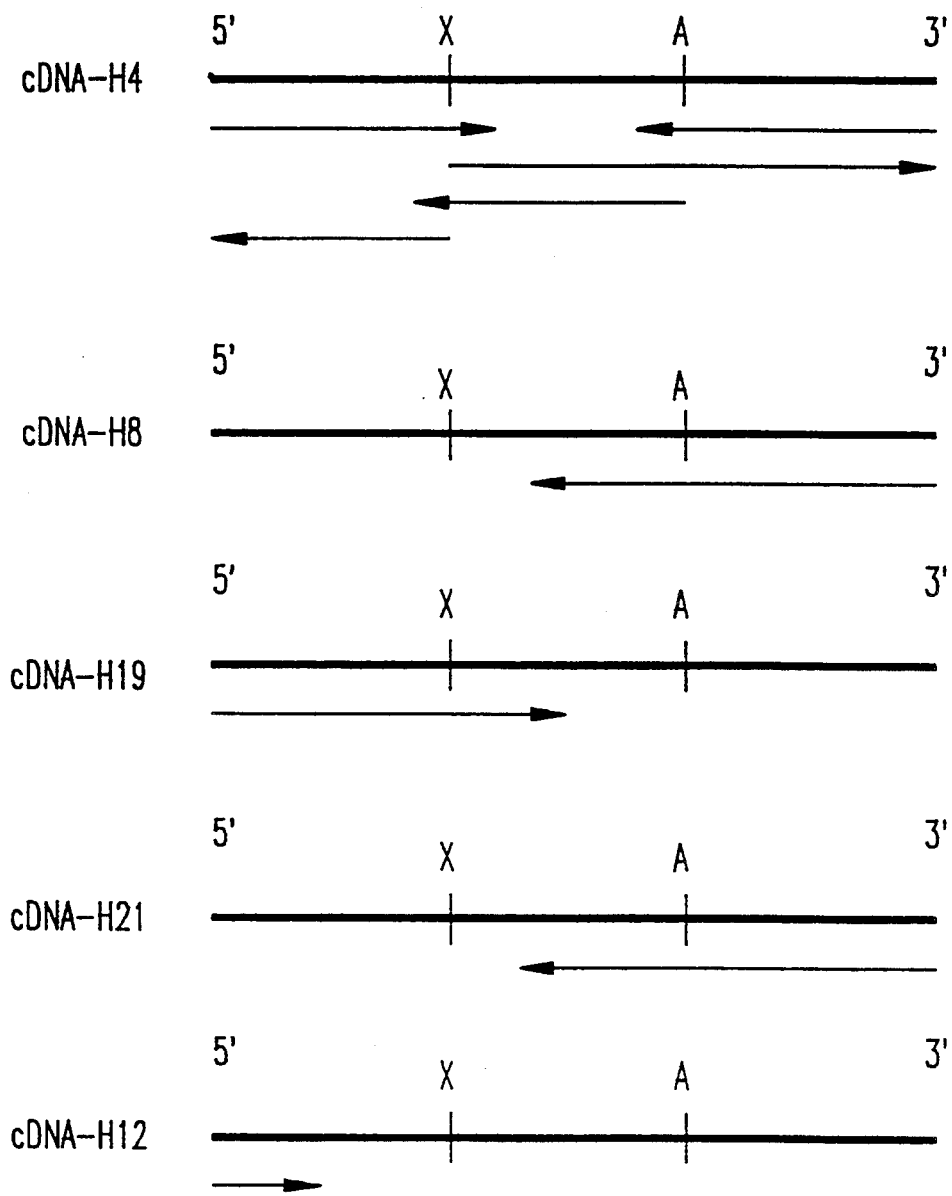
FIG. 1. Restriction map and nucleotide sequencing strategy of cDNA-H4 and its related four cDNAs. The cDNA-H4 originated from HL-60 cells (a promyelocytic leukemia cell line). "X" and "A" refer to the sites within each cDNA which are susceptible to XmnI and AccI, respectively. The arrows indicate the direction and length of each subcloned fragment of cDNA that was sequenced.

The promyelocytic leukemia cell line, HL-60, is a transformed human cell that synthesizes chondroitin sulfate proteoglycans and stores these proteoglycans in its secretory granules. Under certain in vitro conditions, this cell can be induced to differentiate into cells that resemble neutrophils, monocytes, macrophages, eosinophils, and basophils. HL-60 cells (line CCL 240; American Tissue Type Collection, Rockville, Md., USA) were lysed in the presence of guanidine isothiocynate (BRL, Gaithersburg, Md.), and total RNA was purified by the CsCl density-gradient centrifugation technique of Chirgwin et al., Biochemistry 18:5294 (1979). The poly (A)+ RNA that was obtained by oligo (dT)-cellulose (Collaborative Research, Waltham, Mass.) chromatography (Aviv, H., and Leder, P., Proc. Natl. Acad. Sci. USA 4 69:1408 (1972)) was converted into cDNA (Okakajama, H., and Berg, P., Mol. Cell Biol. 2:161–170 (1982)). The resulting cDNAs were blunt ended with T4 DNA polymerase (Biolabs, Beverly, Mass.), the internal EcoRI sites methylated, and the cDNAs ligated to EcoRI poly-linkers. After selection of cDNAs of >500 bp by Sepharose CL-4B (Pharmacia) chromatography, the cDNAs were ligated to dephosphorylated λgt10 DNA. $Escherichia\ coil$ (strain C600 Hfl) were infected with the resulting recombinant bacteriophages resulting in a library with a complexity $>1\times10^6$. The HL-60 cell-derived cDNA library was probed at 37° C. with [α-$^{32}$P]dCTP (3000 Ci/mmol; New England Nuclear, Boston, Mass.) nick-translated pPG-1 in hybridization buffer (50% formamide, 5X SSC (0.15M NaCl/15 mM sodium citrate), 2X Denhardt's buffer, 0.1% sodium dodecyl sulfate (SDS), 1 mM EDTA, 100 μml salmon sperm DNA carrier, and 10 mM sodium phosphate). The filters were washed at 37° C. under conditions of low stringency of 1.0X SSC, 0.1% SDS, 1 mM EDTA, and 10 mM sodium phosphate, pH 7.0. Approximately 500,000 recombinants in the library were plated to isolate the clone designated cDNA-H4 (FIG. 1). The HL-60 cell-derived cDNA library (~500,000 recombinants) were rescreened using cDNA-H4 as the probe. Thirty clones that hybridized under conditions of high stringency (55° C.; 0.2X SSC, 1 mM EDTA, 0.1% SDS, and 10 mM sodium phosphate, pH 7.0) with cDNA-H4 were isolated from the secondary screening of the library.

The individual HL-60 cell-derived cDNAs and their subcloned fragments were inserted into M13mp18 and M13mp19 (Amersham, Arlington Heights, Ill.) and sequenced by the dideoxy chain termination method of Sanger et al., Proc. Natl. Acad. Sci. USA 74:5463 (1977). Both strands of cDNA-H4 were sequenced. The sequencing strategy is presented in FIG. 1. The consensus nucleotide sequence of the HL-60 derived secretory granule proteoglycan peptide core cDNAs is shown in FIG. 2.

A 249 bp EcoRI→EcoRI fragment has been isolated from a EcoRI digest of cDNA-H19. The nucleotide sequence of this fragment (Table I) contains the sequence expected for a polyadenylation site (underlined) and the poly(A)+ tail (underlined). This fragment hybridizes to a genomic fragment that encodes the gene for this proteoglycan peptide core, and thus probably represents the next 249 bp of the transcript.

TABLE I

Consensus nucleotide sequence of the 3' end of the cDNA that encodes serglycin, the peptide core of the HL-60 cell secretory granule proteoglycan (Avraham, S. et al., Proc. Natl. Acad. Sci. USA 86:3763-3767 (1989)).

GAATTCTTAA—AGGATTATGC—TTTAATGCTG—TTATCTATCT—
TATTGTTCTT—GAAAATACCT—GCATTTTTTG—GTATCATGTT—
CAACCAACAT—CATTATGAAA—TTAATTAGAT—TCCCATGGCC—
ATAAAATGGC—TTTAAAGAAT—ATATATATAT—TTTTAAAGTA—
GCTTGAGAAG—CAAATTGGCA—GGTAATATTT—CATACCTAAA—
TTAAGACTCT—GACTTGGATT—GTGAATTATA—ATGATATGCC—
CCTTTTCTTA—TAAAAACAAA—AAAAAAATAA—T [SEQ ID No. 1]

EXAMPLE 2

Chromosomal Localization of the Human Serglycin Gene

For the chromosome localization of the human gene that encodes cDNA-H4, DNA from five different human/mouse (lines 13C2, 24B2, 1711, 462TG, and 175) and 12 different human/hamster (lines 35A2, 35A4, 35B5, 35C1, 35D3, 35D5, 35E4, 35F1, 35F3, 35F5, 89E5, and 95A 4) somatic cell hybrids were digested with BamHI. The resulting fragments were resolved by agarose gel electrophoresis, and the DNA blots were analyzed under conditions of high stringency using cDNA-H4 as a probe. The percent discordance of the cDNA-H4 probe to each human chromosome was determined as described in Table II; a discordant fraction of 0.00 indicates that, in HL-60 cells, the serglycin gene is located on chromosome 10.

TABLE II

Segregation Pattern of cDNA-H4 with DNA from Human/Rodent Somatic Cell Hybrids

The DNA from different human/hamster and human/mouse somatic hybrid cell lines and the DNA from the controls were analyzed for their hybridization to cDNA-H4. The column designations are: +/+, both hybridization to cDNA/cDNA-H4 and the specific human chromosome are present; −/−, hybridization to the cDNA-H4 and the chromosome are both absent; +/−, hybridization is present but the chromosome is absent; and −/+, hybridization is absent but the chromosome is present. For calculation of the discordant fraction for each chromosome, the sum of the +/− and −/+ columns are divided by the sum of the +/+, −/−, +/−, and −/− columns.

The 19q+ category represents the der 19 translocation chromosomes for the hybrid clones derived from fusions with leukocytes from the two different X/19 translocation carriers. The X and Xq− categories represent the intact X and the der X translocation chromosomes. Bruns et al., Biochem Genet. 17:1031-1059 (1979).

| Human Chromosome | +/+ | −/− | +/− | −/+ | Discordant Fraction |
|---|---|---|---|---|---|
| 1 | 1 | 8 | 7 | 1 | 0.47 |
| 2 | 3 | 8 | 5 | 0 | 0.31 |
| 3 | 3 | 6 | 3 | 3 | 0.40 |
| 4 | 2 | 4 | 5 | 3 | 0.57 |
| 5 | 4 | 8 | 4 | 3 | 0.47 |
| 6 | 3 | 5 | 4 | 3 | 0.47 |
| 7 | 6 | 7 | 2 | 2 | 0.24 |
| 8 | 2 | 6 | 6 | 3 | 0.53 |
| 9 | 0 | 5 | 7 | 4 | 0.69 |
| 10 | 8 | 9 | 0 | 0 | 0.00 |
| 11 | 3 | 6 | 5 | 3 | 0.47 |
| 12 | 2 | 7 | 5 | 1 | 0.40 |
| 13 | 5 | 7 | 5 | 1 | 0.40 |
| 14 | 6 | 4 | 1 | 4 | 0.33 |
| 15 | 4 | 8 | 3 | 1 | 0.25 |
| 16 | 3 | 6 | 3 | 3 | 0.40 |
| 17 | 2 | 6 | 5 | 3 | 0.50 |
| 18 | 5 | 7 | 3 | 2 | 0.29 |
| 19 and 19q+ | 6 | 2 | 2 | 7 | 0.53 |
| 20 | 3 | 3 | 3 | 6 | 0.60 |
| 21 | 3 | 4 | 4 | 5 | 0.56 |
| 22 | 3 | 6 | 2 | 3 | 0.36 |
| X and Xq− | 2 | 4 | 6 | 4 | 0.63 |
| Y | 0 | 9 | 7 | 0 | 0.44 |

EXAMPLE 3

Identification of Nucleotide Sequences in the Human Genome that Encode Serglycin The rat L2 cell-derived cDNA, pPG-1, disclosed in Bourdon et al., Proc. Natl. Acad. Sci. USA 82:1322 (1985) was used to identify the genomic fragments encoding human serglycin from a BamHI digest of human genomic DNA. While no hybridization occurred when the DNA blot was probed under conditions of high stringency with either pPG-1 or pPG-M, or probed under conditions of low stringency with pPG-M, at least 10 DNA fragments were visualized when the blot was probed under conditions of low stringency with pPG-1. The large number of DNA fragments detected suggested that there was a multi-gene family in the human which contained repetitive sequences similar to those which encode the serine-glycine repeat region of the L2 cell proteoglycan peptide.

EXAMPLE 4

Isolation and Characterization of the Human Serglycin Gene

Subcloned fragments of the HL-60 cell-derived proteoglycan cDNA, cDNA-H4, were radiolabeled with [$\alpha^{32}$P]dCTP (3000 Ci/mmol; DuPont-New England Nuclear) to a specific activity of $>10^8$ cpm/μg by either nick translation (Maniatis, T. et al., Molecular Cloning. A Laboratory Manual, Cold Spring Harbor Laboratory, Cold Spring Harbor, N.Y., pp. 109-114 (1985)) or random priming (Feinberg, A. P. et al., Anal. Biochem 166:224-229 (1983)), and then were used to screen $\approx 10^6$ recombinants in a EMBL3 human genomic library (Klickstein, L. B. et al., J. Exp. Med. 165:1095-1112 (1987)) by plaque hybridization. Nitrocellulose filters (Millipore, Bedford, Mass.) were probed at 42° C. in 50% formamide, 0.75M NaCl, 75 mM sodium citrate, 5X Denhardt's buffer, 0.1% SDS, 1 mM EDTA, 100 μg/ml salmon sperm DNA carrier, and 10 mM sodium phosphate. The nitrocellulose filters were washed at 55° C. with 30 mM NaCl, 3 mM sodium citrate, 0.1% SDS, 1 mM EDTA, and 10 mM sodium phosphate, pH 7.0. Several independent clones were obtained using the entire 650 bp HL-60 cell-derived cDNA, cDNA-H4 (FIG. 2). However, in order to obtain better representation of the 5' flanking region of the gene, the human genomic library was rescreened using the 136 bp 5'→KpnI fragment of cDNA-H4 to isolate 2 additional clones. The restriction maps of the clones were determined by incubating samples of their DNA separately with AccI, BamHI, EcoRI, HindIII, KpnI, or SalI (New England Biolabs, Beverly, Mass.). The digests were electrophoresed in 1% agarose gels, and the separated DNA fragments were transferred to Nytran membranes (Schleicher and Schuell, Keene, N. H.) (Southern, E. M., J. Mol. Biol. 98:503-517 (1975)). The resulting DNA blots were probed with specific 5' (5'→KpnI and 5'→XmnI) and 3' (XmnI→3' and AccI→3') fragments of cDNA-H4.

Nucleotide Sequence Analysis of the Human Serglycin Gene

Human genomic fragments (FIG. 3) were subcloned into the Bluescript (Stratagene, La Jolla, Calif.) plasmid vector using double enzyme polarized shotgun ligations to improve the efficiency of recombination and to maintain the orientation of the subclones (Kurtz, D. T. et al., Gene 13:145-152 (1980)). Recombinant transformants were identified by colony hybridization and were restriction mapped by the same method as that used above for the phage clones. Double stranded DNA sequencing (Sanger, F. et al., Proc. Natl. Acad. Sci. USA 74:5463-5467 (1977); Zhang, H. et al., Nuc. Acid. Res. 16:1220-7 (1988)) was performed directly on the plasmid subclones using a Sequenase nucleotide sequencing kit (United States Biochemical, Cleveland, Ohio) and $\alpha$-$^{35}$S]dATP (1000 Ci/mmol; Amersham). Universal oligonucleotide primers (SK, KS, T3, T7 and M13rev; Stratagene) were used to determine the sequence of the first and last 300 nucleotides in each the subcloned fragment. Based on the nucleotide sequences of the sense strand and the antisense strand of the genomic fragment, two oligonucleotides that were each 18 nucleotides in length were synthesized on an Applied Biosystems 380A Oligonucleotide Synthesizer at the Harvard Microchemistry Facility, Cambridge, Mass. These oligonucleotides were then used as primers to determine the contiguous nucleotide sequence of the next 200-250 nucleotides in each direction of the double stranded DNA. Additional oligonucleotides complementary to different regions of the cDNA were used as primers to extend the sequence from the exons in both directions. Nucleotide sequence data was entered and edited on an IBM-PC using the Clatech molecular biology software package. Data base searches and homology comparisons with the mouse serglycin gene and other genes were performed using the computers at the Molecular Biology Computer Research Resource at Dana-Farber Cancer Institute, Boston, Mass.

When a human genomic library was screened using the entire 650 bp cDNA-H4 probe, six independent clones were isolated (designated as λHG-PG1 to λHG-PG6). Restriction mapping of these clones revealed that all six of the clones lacked a 5' 12 kb EcoRI→EcoRI fragment and failed to hybridize to a 136 bp 5'→KpnI fragment of cDNA-H4. Rescreening of the genomic library with the 5' fragment of cDNA-H4 resulted in the isolation of two additional clones that were designated as λHG-PG7 and λHG-PG8, respectively. When analyzed by restriction mapping, clones λHG-PG6, 80 HG-PG7, and λHG-PG8 contained overlapping genomic sequences which taken together include the entire gene which encodes human serglycin.

Figure 3:
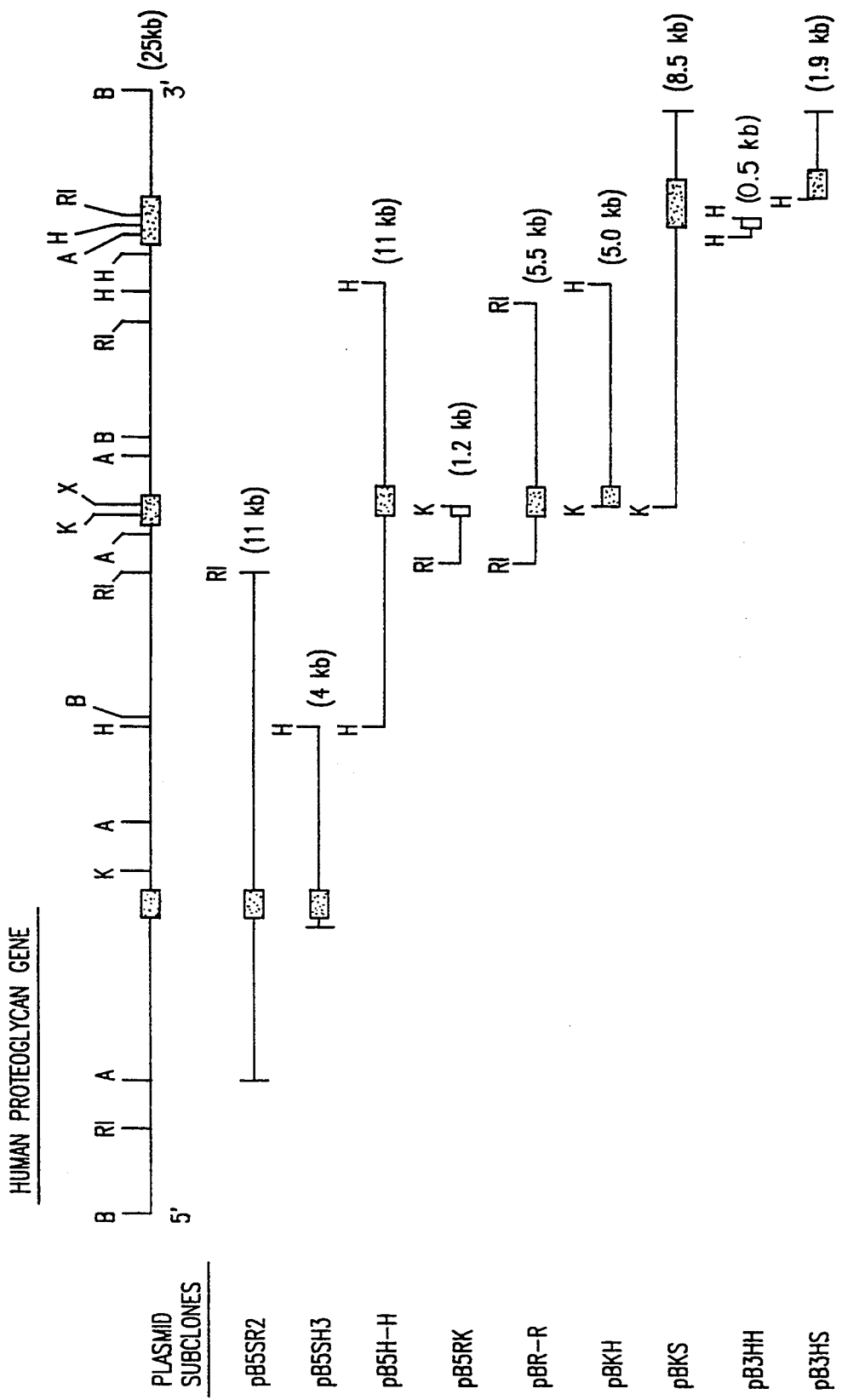
FIG. 3. Restriction map of the human serglycin gene isolated from a human leukocyte genomic DNA library (Klickstein, L. B. et al., J. Exp. Med. 165:1095–1112 (1987)).

Detailed restriction mapping of these subclones revealed that this gene spans at least 16.6 kb and consists of 3 exons (FIGS. 3 and 4). Between the first and second exon is a 8.4 kb intron, and between the second and third exon is a 6.7 kb intron. Both introns begin with the nucleotide sequence "GTAAG" and end with the sequence "CAG". Analysis of the nucleotide sequence of this gene revealed that exon 1 encodes the 5' untranslated region of the mRNA transcript and the entire 27 amino acid hydrophobic signal peptide of the translated molecule. Exon 2 encodes a 49 amino acid portion of the peptide core (amino acid residues 28 to 76) which would be predicted to be the N-terminus of the molecule after the hydrophobic signal peptide is removed in the endoplasmic reticulum. Exon 3 (634 bp) is the largest exon and encodes the remaining 82 amino acids of the translated molecule and the entire 3' untranslated region of the mRNA transcript. These 82 amino acids encode a 17 amino acid sequence (residues 77 to 93) that immediately precedes the glycosaminoglycan attachment region, the 18 amino acid serine-glycine rich region (residues 94 to 111), the C-terminus of the translated molecule (residues 112 to 158).

Determination of the Transcription-Initiation Site of the Human Serglycin Gene.

A S1 nuclease mapping analysis was performed to identify the transcription-initiation site of the human gene that encodes the peptide core of serglycin proteoglycans in HL-60 cells. A 4 kb SalI→HindIII fragment of the genomic clone λHG-PG7 was subcloned into Bluescript (designated pB5S H3 ). An oligonucleotide (5→CTTFGAACTG AGGATTCCAGAA→3'[SEQ ID No. 2]) was synthesized that corresponded to the residues 89 to 110 of the antisense strand of cDNA-H4. Ten nanograms of this oligonucleotide were hybridized to 4 μg of alkali-denatured pB5SH3, and a complementary strand of DNA was synthesized under conditions similar to that described above except that it was labeled with [$\alpha$-$^{32}$P]dATP. A 400 bp antisense DNA probe was isolated following electrophoresis of the synthetic product on a denaturing 8M urea/8% polyacrylamide gel. The single-stranded radiolabeled DNA fragment was identified by autoradiography, electroeluted, and ethanol precipitated. A 50,000 cpm sample of the radiolabeled DNA fragment was hybridized to ≈15 μg of HL-60 cell-derived total RNA (Chirgin, J. M. et al., Biochemistry 18:5294–5299 (1979)) or 1 μg of HL-60 cell-derived poly(A)+ RNA (Aviv, H. et al., Proc. Natl. Acad. Sci. USA 69:1408–1412 (1972)) at 48° C. for 16 h in 80% formamide, 400 mM NaCl, 1 mM EDTA, and 40 mM Pipes (pH 6.4). The $^{32}$P-DNA/RNA hybrid was incubated with 100 U of S1 nuclease (Pharmacia) for 60 min. At the end of the reaction, the sample was extracted with phenol, and ethanol precipitated at −80° C. Three microliters of 1 mM EDTA and 10 mM Tris-HCl (pH 8.0) and 4 μl of formamide loading buffer were added to the precipitated sample. The sample was boiled, and loaded onto a 8M urea/8% polyacrylamide sequencing gel along side a digest of $^{32}$P-labeled pBR322 (New England Biolabs) and a sequencing ladder of pBSH3 that had been primed with the same oligonucleotide. For two negative controls, S1 nuclease reactions were concurrently preformed with 15 μg of tRNA (Bethesda Research Labs) or MBBC (Razin, E. et al., J. Biol. Chem. 257:7229–7236 (1982)) total RNA.

HL-60 cell-derived total RNA and poly(A)+ RNA protected 132 nucleotides of the probe from degradation by S1 nuclease. Therefore, it was concluded that the putative transcription-initiation site in HL-60 cells for this gene resided 53 bp upstream of the translation-initiation site. The $^{32}$P-labeled 5' antisense 400 bp DNA fragment was not protected if it was incubated with tRNA or mouse mast cell RNA prior to exposure to S1 nuclease. This deduced transcription-initiation site in HL-60 cells corresponds to the deduced transcription-initiation site of the analogous gene that is expressed in BMMC-derived mast cells and rat basophilic leukemia cells (Bourdon, M. A. et al., Mol. Cell Biol. 7:33–40 (1987)), but not in rat L2 yolk sac tumor cells (Bourdon, M. A. et al., Mol. Cell Biol. 7:33–40 (1987)).

FIG. 3 is a restriction map of the human gene. FIG. 4 is the nucleotide sequence of the gene that encodes human serglycin including 5' flanking and intron sequences.

Cloning of the Mouse Serglycin Gene

A 15 kb mouse genomic fragment containing the gene that encodes the mouse serglycin was cloned by screening a mouse genomic library derived from a Sau3AI digest of BALB/c mouse liver DNA (Avraham, S., et al., Proc. Natl. Acad. Sci. USA 86:3763–3767 (1989)), using a [α-$^{32}$P]dCTP labeled 450 bp AccI→3' gene-specific fragment of a bone marrow-derived mast cells cDNA (cDNA-M6) that encodes the peptide core of mouse secretory granule proteoglycan using methods as described above. The nucleotide sequence and the deduced amino acid sequence of this gene is presented in FIG. 5.

Neither the human nor the mouse gene have a classical TATA box (Breathnach, R. et al., Ann. Rev. Biochem. 50:349–383 (1981)) or GC-rich element (Sehgal, A. et al., Mol. Cell. Biol. 8:3160–3167 (1988)) ≈30 bp upstream of its transcription-initiation site. Therefore, the serglycin gene that is expressed in hematopoietic cells has an unusual promoter. The 5' flanking region has not been described for any other human proteoglycan peptide core gene, and thus comparisons with genes that encode other proteoglycan peptide cores cannot yet be made. Of importance is the finding that 96% of the nucleotides that are present in a 119 bp nucleotide sequence just upstream of the transcription-initiation site of the human (residues −1 to −119) and mouse (residues −1 to −123) gene are identical. This degree of conservation greatly exceeds that obtained when any other 119 bp region within the exons of the gene in these two species is compared, and suggests that important cis acting regulatory elements are present in this conserved nucleotide sequence.

EXAMPLE 5

Stable Transfection of Rat-1 Fibroblasts with the Mouse Serglycin Gene

Fisher rat-1 fibroblasts were grown in Dulbecco's modified essential medium (DMEM) supplemented with 10% fetal calf serum, 2 mM L-glutamine, 100 U/ml of penicillin, and 100 μg/ml of streptomycin, at 37° C. in a humidified atmosphere of 5% $CO_2$. DNA cotransfections were performed essentially as described elsewhere (Southern, P. J. et al., J. Mol. Appl. Gen. 1:327–341 (1982)). In brief, 3–4×10$^5$ rat-1 fibroblasts were placed into each 10-cm plastic culture dish containing DMEM for 12–24 h before cotransfection with the mouse genomic clone λMG-PG 1 and the selectable maker pSV2 neo. A calcium phosphate/DNA precipitate was created by adding 0.5 ml of a 250-mM solution of calcium phosphate containing 5 μg of the λMG-PG1 DNA and 0.5 μg of pSV2 neo drop-wise in the presence of bubbling air to 0.5 ml of 280 mM NaCl, 10 mM KCl, 12 mM dextrose, 1.5 mM sodium phosphate, and 50 mM HEPES (pH 7.1). The precipitate that formed after 30 min incubation was added to a culture dish of fibroblasts, and 10 to 18 h later, the DNA precipitate was removed. The transfected cells were washed twice with growth medium and then were allowed to recover for 24 h before being trypsinized and split at a ratio of 1:6. The resulting fibroblasts were plated into new 10-cm plastic dishes and cultured for 2 to 3 wk in DMEM containing 500 μg/ml gentamicin (Gibco); the culture medium was changed every 3 days. At the end of this period, gentamicin-resistant colonies of transfected fibroblasts were individually picked with cloning cylinders and grown as cell lines in culture medium containing 100 μg/ml gentamicin.

RNA and DNA Blot Analysis of Rat-1 Fibroblasts Stably Transfected with the Mouse Serglycin Gene Total RNA was prepared from mouse bone marrow-derived mast cells, rat-1 fibroblasts, and transfected rat-1 fibroblasts by a guanidinium thiocyanate method (Chirgin, J. M. et al., Biochemistry 18:5294–5299 (1979); Glisin, V. et al., Biochemistry 13:2633–2637 (1974)). RNA (5 μg/lane) was electrophoresed in 1% formaldehyde-agarose gels, and transferred to Zetabind (Thomas, P. S., Proc. Natl. Acad. Sci. USA 77:5201–5205 (1980)). The resulting RNA blots were incubated at 42° C. for 24 h in hybridization buffer containing a radiolabeled AccI→3' fragment of cDNA-M6. The blots were washed under conditions of high stringency, and autoradiography was performed. The mouse serglycin probe was removed from the blots by high temperature washing, and the blots were reprobed with an actin cDNA to quantitate the amount of mRNA that had been loaded in each lane.

DNA was isolated (Blin, N. et al., Nucleic Acids Res. 3:2303–2308 (1976)) from the mouse liver, rat liver, rat-1 fibroblasts, and transfected rat-1 fibroblasts, and samples were digested (10 μg/digest) separately with XmnI, BamHI, BglII, SspI, Sau3AI, HindIII, or EcoRI for 4 h at 37° C. The fragments were resolved by agarose gel electrophoresis and were transferred to Zetabind. The resulting DNA blots were analyzed for hybridization under conditions of high stringency with the ACCI→3' fragment of the mouse cDNA-M6 as a probe. Expression of the Mouse Gene that Encodes the Peptide Core of Mouse Serglycin Gene in Transfected Rat-1 Fibroblasts To demonstrate that λMG-PG1 contained the entire mouse serglycin gene, including its promoter region, and that this mouse genomic clone could be expressed in another mammalian cell, rat-1 fibroblasts were co-transfected with λMG-PG1 and the dominant neo-resistant selectable marker encoded by the plasmid pSV2 neo. Seventeen independent clones of neo-resistant transfected rat-1 fibroblasts were isolated and were expanded separately. Total RNA was isolated from bone marrow-derived mast cells, neo-transfected rat-1 fibroblasts, and the cotransfected rat-1 fibroblast cell lines.

The gene-specific serglycin probe failed to hybridize to any transcript in RNA blots of non-transfected fibroblasts; however, it did hybridize to a 1.0-kb RNA transcript in mouse bone marrow-derived mast cells and in two of the cotransfected rat-1 fibroblast cell lines. Primer extension analyses were performed using RNA from the transfected fibroblasts to determine the transcription-initiation site. When RNA from the transfected cells was used as an RNA template, $\approx 80$ nucleotides were extended onto the oligonucleotide primer that corresponded to residues 78 to 98 of cDNA-M6, resulting in a DNA product of about 100 nucleotides in length. A DNA product of $\approx 60$ nucleotides was obtain when the alternative primer that corresponded to residues 39 to 59 of cDNA-M6 was used in the assay.

Genomic DNA was prepared from the above two clones of transfected rat-1 fibroblasts, and was digested with BglII, XmnI, SalI, or BamHI. DNA blots of the digests were probed with the AccI→3' gene-specific fragment of cDNA-M6 to demonstrate that these transfected rat-1 fibroblast cell lines contained mouse serglycin genomic sequences. The mouse proteoglycan probe hybridized to a 2.7-kb fragment present in the BglII digest of mouse live DNA, and to a 7.5-kb fragment in the BglII digests of both rat liver DNA and rat-1 fibroblast DNA. The transfected fibroblasts differed from the non-transfected rat-1 fibroblasts in that they contained both the 2.7-kb and the 7.5-kb DNA fragments. Based on the relative intensity of hybridization of the gene-specific probe to the 2.7-kb fragment present in the BglII digests of equal amounts of mouse liver DNA and fibroblast DNA, the fibroblast cell lines may have incorporated 10-20 and 2-3 copies, respectively, of the mouse serglycin gene into their genome.

Transfections have been performed in Chinese hamster ovary cells with a cDNA that encodes the peptide core of the fibroblast-derived dermatan sulfate proteoglycan called decorin (Yamaguchi, Y. et al., Nature 336:244-246 (1988)) and in COS-7 cells with a cDNA that encodes the peptide core of the T-cell derived invariant chain proteoglycan that associates with Ia (Miller, J. et al., Proc. Natl. Acad. Sci. USA 85:1359-1363 (1988)), but no transfections have been reported using a genomic clone that contains an entire proteoglycan peptide core gene.

EXAMPLE 6

Preparation of Antibodies to Peptides of the Amino Acid Consensus Sequence Which Recognize Native HL-60 Cell Derived Glycin A 16 amino acid peptide 02 [Ser-Asn-Lys-Ile-Pro-Arg-Leu-Arg-Thr-Asp-Leu-Phe-Pro-Lys-Thr-Arg] [SEQ ID No. 3] was chemically synthesized, coupled to hemocyanin, and injected into a New Zealand White rabbit. This peptide corresponds to residues 64-79 of the translated molecule and was a region of the core that preceded the serine-glycine rich glycosaminoglycan attachment region.

The induction of antibodies which specifically recognize the peptide core protein of human serglycin was tested as follows. The peptide (3 mg) was coupled with 5 mg of Keyhole Limpet hemocyanin (Sigma) in the presence of 0.25% glutaraldehyde, and polyclonal antibodies were raised to the coupled peptide in New Zealand White rabbits using standard immunization methodologies. Antibody titers in whole sera were measured using an enzyme linked immunosorbent assay (ELISA). Each microtiter well was incubated overnight at 4° C. with 1 μg of synthetic peptide in phosphate buffered saline. After the remaining protein binding sites in the wells were blocked by a 1 h incubation with 1% (w/v) bovine serum albumin (Sigma), the wells were washed with phosphate buffered saline containing 1% (w/v) Tween 20. Rabbit sera that was serially diluted in phosphate buffered saline was added, followed by horseradish peroxidase-conjugated goat anti-rabbit IgG (Bio-rad, Richmond, Calif.); the wells were then assayed spectrophotometrically for development of the 2,2'azino-di-[3-ethyl-benzthiazoline sulfonate] dye (Boehringer-Mannheim, Indianapolis, Ind.). Peptide01 (Ser-Val-Gln-Gly-Tyr-Pro-Thr-Gln-Arg-Ala-Arg-Tyr-Gln-Trp-Val-Arg) [SEQ ID No. 4] that corresponded to residues 24 to 39 of the deduced amino acid of cDNA-H4 was also synthesized and used in the ELISA to confirm the specificity of the rabbit antisera. Anti-peptide IgG was partially purified by ammonium sulfate precipitation followed by ion exchange chromatography.

Anti-peptide IgG ($\sim$30 μg) was incubated with 100 μl of a 15% (w/v) suspension of the Protein A-Sepharose beads (Sigma) in RIPA buffer for 1 h at room temperature. The resulting Protein A-Sepharose-IgG complex was added to 1 ml of RIPA cell lysates containing $5 \times 10^6$ cell equivalents of [$^{35}$S]methionine-labeled or [$^{35}$S]sulfate-labeled HL-60 cells that had been precleared by incubation for 24 h with Protein A-Sepharose alone and then for 24 h with Protein A-Sepharose/preimmune IgG. After a 18-24 h incubation at 4° C. with Protein A-Sepharose/anti-peptide IgG, the beads were washed 3 times by centrifugation with 0.1% bovine serum albumin, 0.5% Tween 20, and 10 mM phosphate buffered saline (pH 7.2) containing either 10 mM unlabeled methionine or unlabeled sodium sulfate. The bound radiolabeled antigens were eluted by suspending the beads in 60 μl of Laemmli buffer and incubating for 5 min at 95° C. The eluates were electrophoresed in 15% SDS-PAGE gels, stained with Coomassie Brilliant blue, dried, and autoradiographed using Kodak XAR-5 film.

Figure 6:
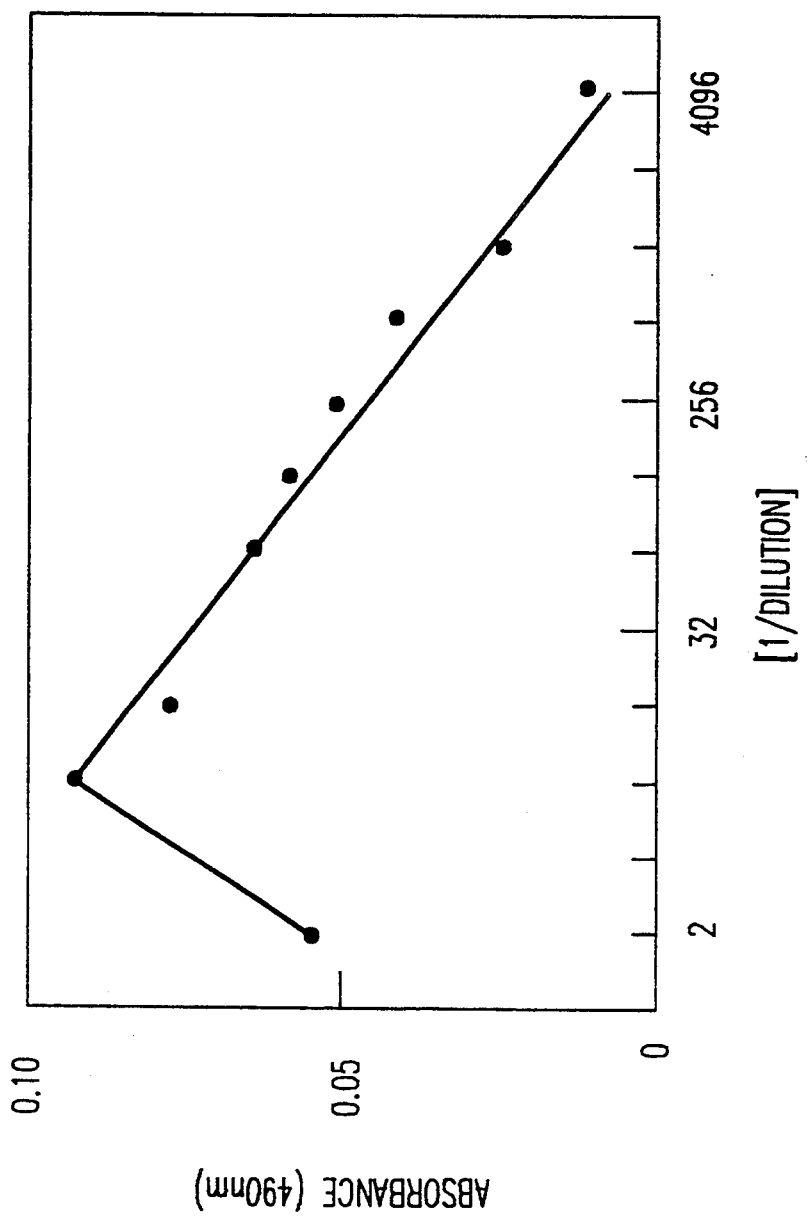
FIG. 6. ELISA of the rabbit anti-peptide 02 serum. Peptides 01 (o--o) and 02 (●--●) were coupled to separate microtiter wells and different dilutions of the rabbit anti-peptide 02 sera were examined for their reactivity against the specific peptide as detected spectrophotometrically at 490 nm after the addition of horseradish peroxidase-conjugated goat anti-rabbit antibody followed by 2,2'azino-di-[3-ethyl-benzthiazoline] sulfonate. The amino acid sequence of peptide 01 is Ser-Val-Gln-Gly-Tyr-Pro-Thr-Gln-Arg-Ala-Arg-Tyr-Gln-Trp-Val-Arg. The amino acid sequence of peptide 02 is Ser-Asn-Lys-Ile-Pro-Arg-Leu-Arg-Thr-Asp-Leu-Phe-Pro-Lys-Thr-Arg.

In the ELISA, the antiserum gave half-maximal binding at an approximate 500 fold dilution (FIG. 6). The anti-peptide 02 serum failed to recognize peptide 01 which corresponded to deduced amino acid residues 24 to 39 of the same cDNA (FIG. 6). The preimmune sera also failed to react with the coupled peptide 02. When 1 μl of the antisera was preincubated with 1 μg of peptide 02 for 60 minutes at 25° C., no immunoreactivity was detected in the ELISA.

An IgG-enriched fraction of the anti-peptide 02 sera was used to determine if Protein A-Sepharose-bound antibodies would recognize the initially-translated serglycin and the mature proteoglycan. A prominent 20,000 $M_r$ protein was specifically immunoprecipitated from lysates of 2 min [$^{35}$S]methionine-labeled HL-60 cells, whereas both a 20,000 $M_r$ protein and a macromolecule that barely entered the gel were specifically immunoprecipitated from 10 min radiolabeled cells. After a 10 min pulse and a 5 min chase, the 20,000 $M_r$[$^{35}$S]methionine-labeled protein was less apparent while the macromolecule was somewhat increased. The [$^{35}$S]methionine-labeled macromolecule corresponded in size exactly to the [$^{35}$S]sulfate-labeled proteoglycan that was precipitated after an overnight radiolabeling of the cells with [$^{35}$S]sulfate. Because precipitation was inhibitable by preincubation of the Protein A-Sepharose-immune IgG with 1 μg of the synthetic peptide 01, it was concluded that the rabbit anti-peptide 02 antibodies recognize the precursor and mature human glycin.

Figure 7A:
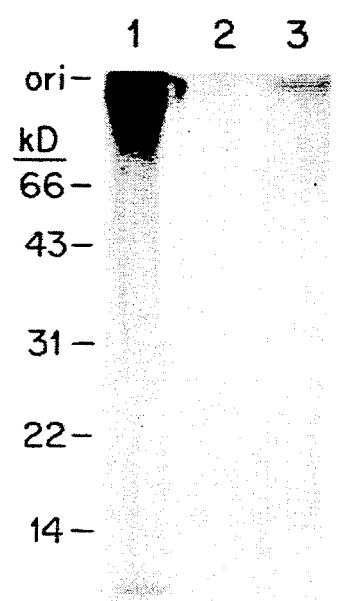
FIGS 7(A and B). SDS-PAGE analysis of immunoprecipitates of lysates of [$^{35}$S]sulfate-labeled (A) and [$^{35}$S]methionine-labeled (B) HL-60 cells. (A) Lysates of [$^{35}$S]sulfate-labeled HL-60 cells were analyzed before (lane 1) and after immunoprecipitation with anti-peptide 02 IgG in the presence (lane 2) or absence (lane 3) of peptide 02. (B) Lysates of HL-60 cells were analyzed after a 2 min (lane 1) or a 10 min (lane 2) incubation with [$^{35}$S]methionine by immunoprecipitation with anti-peptide 02 IgG. Ten min [$^{35}$S]methionine-labeled HL-60 cells were washed and then incubated for an additional 5 min in methionine-containing enriched medium before lysates were immunoprecipitated with anti-peptide 02 IgG (lane 3). Lysates of 5 min. labeled HL-60 cells were immunoprecipitated with anti-peptide peptide 02 IgG in the presence of peptide 01 (lane 4) or peptide 02 (lane 5). The [$^{35}$S]methionine-labeled proteins that were non-specifically immunoprecipitated with pre-immune IgG are depicted in lane 6. The origin (ori) and the $M_r$ markers are indicated on the far left and right of each panel. The arrows indicate the precursor peptide core and the mature proteoglycan that are immunoprecipitated with anti-peptide 02 IgG.
Figure 7B:
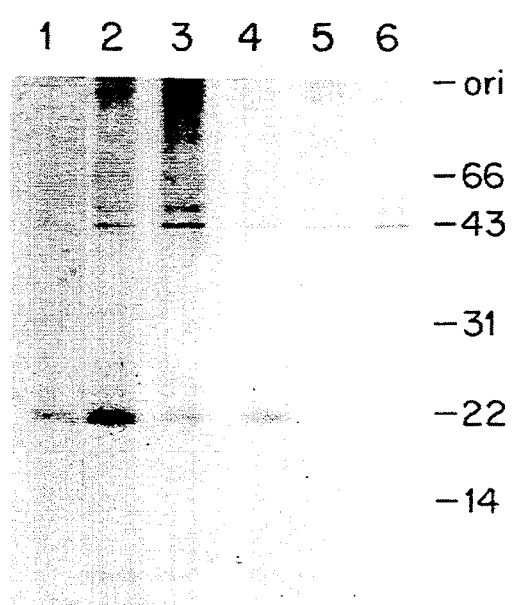

As shown in FIG. 7, the size of the immunoprecipitated peptide core protein was approximately 13,000 daltons, consistent with the size predicted by Stevens et al., J. Biol. Chem. 263:7287 (1988) for the peptide core which has lost its 27 amino acid signal peptide.

EXAMPLE 7

Isolation of Serglycin Proteoglycans

Human serglycin proteoglycans can be isolated using common protein isolation techniques known in the art such as column chromatography, gel electrophoresis, affinity chromatography, or immuno-extraction techniques using the antibody described above. For example, such proteoglycans may be extracted by the following procedure (Stevens, R. L., et al., J. Biol. Chem. 260:14194–14200 (1985)).

Bone marrow-derived mast cells pellets are lysed by resuspension for 30 s in 50 μl of 1% Zwittergent 3-12 containing protease inhibitors, followed by the addition of 2.35 ml of 4M guanidine HCl (GnHCl) containing CsCl (density 1.4 g/ml). These detergent-GnHCl proteoglycan extracts are then pooled such that in a typical experiment 48 ml of extract is obtained from approximately $2 \times 10^9$ bone marrow-derived mast cells, of which $3 \times 10^7$ are radiolabeled. The pooled extracts are centrifuged at 17° C. for 48 h at $95,000 \times g$, and the gradients are divided in most experiments into two equal fractions termed $D_1$ (bottom) and $D_2$ (top), respectively. The distribution of chondroitin sulfate E proteoglycan in fractions from the CsCl gradient or from subsequent ion exchange or gel filtration chromatography is determined by suspending a sample of each fraction in 12.5 ml of Hydrofluor and quantitating $^{35}$S or $^3$H radioactivity in the radiolabeled proteoglycan on a Tracor Analytic Mark III liquid scintillation counter. Protein is detected by the method of Lowry et al., with bovine serum albumin as a standard or by optical density at 280 nm. Nucleic acids are detected at a wavelength of 260 nm. The bottom fraction of each CsCl gradient is placed in dialysis tubing of 50,000 $M_r$ cut-off and dialyzed at 4° C. against 1M NaCl for 24 h and then for an additional 24 h against 1M urea containing 0.05M Tris-HCl, pH 7.3. The dialysate is adjusted to 4M in urea by the addition of solid urea and applied to a $0.8 \times 29$-cm column of DEAE-52 previously equilibrated in 4M urea, 0.05M Tris-HCl, pit 7.8. The ion exchange column is washed with 35 ml of 4M urea, 0.05M Tris-HCl, pit 7.8, and the chondroitin sulfate E proteoglycan eluted with a 180-ml linear gradient of NaCl (0–1.0M) in the urea buffer at a flow rate of 4 ml/h. Two-ml fractions are collected, and the proteoglycan-enriched fractions, detected by monitoring a portion of the fraction for either $^{35}$S or $^3$H radioactivity if the cells have been prelabelled, are pooled, dialyzed 48 h at 4° C. against 0.1M NH$_4$HCO$_3$, and lyophilized. This material is redissolved in 100 μl of 4M GnHCl/0.1M sodium sulfate/0.1M Tris-HCl, pH 7.0, applied to a $0.6 \times 100$-cm column of Sepharose CL-4B in this same buffer, and eluted from the column at a flow rate of 1.5 ml/h. One-half ml fractions are collected and analyzed for radioactivity and absorbance at 280 nm. The proteo-glycan-containing fractions are pooled, dialyzed against 0.1M NH$_4$HCO$_3$ and lyophilized.

EXAMPLE 8

Isolation and Protease-Resistance of HL-60 Cell Serglycin Proteoglycan

Radiolabeling of HL-60 Cells

HL-60 cells (line CCL 240; American Type Culture Collection, Bethesda, Md.) were cultured in enriched medium [RPMI-1640 medium supplemented with 10% (v/v) fetal calf serum, 2 mM L-glutamine, 0.1 mM nonessential amino acids, 100 U/ml of penicillin, and 100 μg/mi of streptomycin (Gibco, Grand Island, N.Y.)] at 37° C. in a humidified atmosphere of 5% $CO_2$. For [$^{35}$S]methionine-labeling, HL-60 cells were preincubated at a concentration of $10^7$ cells/ml for 10 min in methionine-free, enriched medium containing dialyzed fetal calf serum. Approximately 500 μCi/ml of [$^{35}$S]methionine (129 Ci/mmol; Amersham, Arlington Heights, Ill.) was then added. The HL-60 cells were incubated for an additional 2 to 10 min at 37° C., centrifuged in the cold at $120 \times g$, and washed at 4° C. in enriched medium. In the pulse-chase experiments, HL-60 cells were [$^{35}$S]methionine-labeled for 10 min, were washed as above, and were resuspended in normal enriched medium at 37° C. for an additional 5 min. Aliquots of $5 \times 10^6$ [$^{35}$S]methionine-labeled HL-60 cells were lysed in 1 ml of RIPA buffer [0.15M NaCl, 1% deoxycholate, 1% Nonident P-40, 0.1% SDS, 10 mM N-ethylmaleimide, 2 mM phenylmethylsulfonyl fluoride, 10 mM NaF, and 0.1M Tris-HCl, pH 7.2], and immunoprecipitates of the lysates were analyzed by SDS-polyacrylamide gel electrophoresis (SDS-PAGE) as described below.

For [$^{35}$S]sulfate labeling, HL-60 cells were incubated in enriched medium containing 50 μCi/ml of 35S]sulfate ($-4000$ Ci/mmol; DuPont-New England Nuclear, Boston, Mass.) for 1 h at a density of $1 \times 10^7$ cells/ml or for 18 h at a density of $2 \times 10^{\neq}$cells/ml. The radiolabeled cells were centrifuged at 4° C. for 10 min at $120 \times g$, and 150 μl of 1% (w/v) zwittergent 3-12 (Calbiochem, San Diego, Calif.) containing 100 μg of chondroitin sulfate A (Miles Scientific, Naperville, Ill.) and 100 μg of heparin (Sigma, St. Louis, Mo.) glycosaminoglycan carriers were added to each cell pellet followed by 1.35 ml of 4M GnHCl, 0.1M sodium sulfate, and 0.1M Tris-HCl. A sample of each lysate and supernatant was chromatographed on Sephadex G-25/PD-10 columns (Pharmacia, Piscataway, N.J.) to quantitate the incorporation of [$^{35}$S]sulfate into macromolecules.

In order to isolate the [$^{35}$S]sulfate-labeled HL-60 cell serglycin proteoglycans, solid CsCl was added to the remainder of the cell lysates to achieve final densities of 1.4 g/ml. Following centrifugation for 48 h at ~100,000×g, the bottom 33% of each CsCl gradient was dialyzed sequentially against 0.5M sodium acetate for 24 h and 0.1M ammonium bicarbonate for an additional 24 h. The dialysates were lyophilized and redissolved in 0.4 ml of water. Samples of partially purified [$^{35}$S]sulfate-labeled proteoglycans were incubated for 30 min with or without 10 μg of Pronase (Calbiochem), and the digests were applied sequentially to a 0.8×85 cm column of Sepharose CL-6B (Pharmacia) that had been equilibrated with 4M GnHCl, 0.1M sodium sulfate, 0.1M Tris-HCl, pH 7.2. As a control, samples of [$^{35}$S]sulfate-labeled chondrosarcoma proteoglycans were analyzed in parallel for their susceptibility to Pronase by incubation of 1 μg proteoglycan in 50 μl Hanks' balanced salt solution at 37° C. for 30 min with 5 μg Pronase. Pronase-sensitive chondrosarcoma proteoglycans are extracellular matrix proteins and are distinguished from secretory granule proteoglycans.

No substantial change in the hydrodynamic size of the HL-60 cell [$^{35}$S]sulfate-labeled serglycin proteoglycans was detected following Pronase treatment, whereas rat [$^{35}$S]sulfate-labeled chondrosarcoma proteoglycans were susceptible to degradation. These results show that the proteoglycan was resistant to Pronase digestion.

EXAMPLE 9

Identification of Transcriptional Regulatory Elements of the Serglycin Gene and the Trans-acting Proteins that Bind to these Elements A. Experimental Procedures 1. Cell Lines—Rat basophilic leukemia-1 (RBL-1) cells (line CRL-1378, American Tissue Culture Collection (ATCC), Rockville, Md.) and mouse myelomonocytic WEHI-3 cells (line TIB-68; ATCC) are cell lines of hematopoietic origin that abundantly express the serglycin transcript, whereas Fisher rat-1 fibroblasts (obtained from R. A. Weinberg, Whitehead Institute, Massachusetts Institute of Technology, Cambridge, Mass.) and mouse NIH/3T3 fibroblasts (line CRL 1658; ATCC) do not (Tantravahi et al., Proc. Natl. Acad. Sci. USA 83:9207-9210 (1986)). Rat basophilic leukemia-1 cells, WEHI-3 cells, and the two fibroblast cell lines were grown in enriched medium (Dulbecco's modified Eagle's Medium supplemented with 10% fetal calf serum, 2 mM L-glutamine, 100 U/ml penicillin, and 100 μg/ml streptomycin (GIBCO, Grand Island, N.Y.)) at 37° C. in a humidified atmosphere of 6% $CO_2$. Cells were split 1:4 every 3 days.

2. Plasmid DNA Constructs—With a polymerase chain reaction methodology (Saiki et al., Science 239:487-491 (1988)), various lengths of the 504-bp 5' flanking region of the mouse serglycin gene (Avraham et al., J. Biol. Chem. 264:16719-16726 (1989)) that all extend upstream of residue +24 were obtained. DNA constructs were prepared by ligating the various DNA fragments into the HindIII/XbaI restriction-enzyme cloning sites of pΦGH and pSV40-hGH. pΦGH is a pUC12 plasmid that contains a promoterless hGH gene (Selden et al., Mol. Cell Biol. 6:3173-3179 (1986)), and pSV40-hGH is a plasmid which contains the early SV40 promoter without its enhancer linked to the structural sequences of the hGH gene (Chung et al., Proc. Natl. Acad. Sci. USA 83:7918-7922 (1986); Sarid et al., J. Biol. Chem. 264:1022-1026 (1989)). A pUC12 plasmid that contains an enhancerless thymidine kinase promoter ligated to the hGH gene (pTKGH), and a pUC12 plasmid that contains both the enhancer and promoter of the mouse metallothionein-I gene ligated to the hGH gene (pXGH5) (Selden et al., Mol. Cell Biol. 6:3173-3179 (1986)) were used as positive control plasmids in the DNA transfections. As described for other cell types (Sarid et al., J. Biol. Chem. 264:1022-1026 (1989); Selden et al., Science 236:714-718 (1987)), the latter well-characterized metallothionein-I-hGH fusion gene was used to optimize the DNA transfections and to normalize the efficiency of expression of hGH by the different cells.

Relevant 21-mer oligonucleotides that span the mutation site were used to perform site-directed mutagenesis (Zoller et al., DNA 3:479-488 (1984)) on three nucleotides in a plasmid (designated pPG(−504/+24)hGH) containing the 504-bp 5' flanking region of the serglycin gene. In these constructs, the adenosine at residue −28 was converted to a cytosine, the cytosine at residue −30 was converted to an adenosine, or the adenosine at −38 was converted to a guanosine. The oligonucleotides used in the polymerase chain reactions, the site-directed mutagenesis, and the gel mobility shift experiments described below were synthesized on a Cyclone Plus DNA Synthesizer (Milligen/Biosearch, Novato, Calif.). The relevant nucleotide sequences within the different plasmid constructs was verified by dideoxy sequencing of the plasmid DNA, as described by Sanger and coworkers (Sanger et al., Proc. Natl. Acad. Sci. USA 74:5463-5467 (1977)) with modifications essential for double-stranded DNA sequencing (Chen et al., DNA 4:165-170 (1985)).

3. Transfection Experiments—Rat basophilic leukemia-1 cells were transiently transfected with the plasmid DNA constructs with DEAE-dextran (Lopata et al., Nucleic Acids Res. 12:5707-5717 (1984)). The day before DNA transfection, the rat basophilic leukemia-1 cells ($1 \times 10^6$/dish) were plated in 100-mm culture dishes. Immediately before transfection, cells were washed once with 3 ml of serum-free enriched medium, and then 2.5 ml of serum-free enriched medium containing 5 μg of supercoiled plasmid DNA complexed to 20 mg/ml DEAE-dextran ($M_r$ 500,000 daltons) was added. The dishes were incubated for 4 h at 37° C. in a humidified atmosphere of 6% $CO_2$, the transfection solution was removed by aspiration, 3 ml of serum-free enriched medium containing 10% dimethyl sulfoxide was added, and the cultures were incubated for 2 min more at room temperature. The transfected cells were treated with dimethyl sulfoxide, washed twice with 4 ml of serum-free enriched medium, and then cultured in 10 ml enriched medium at 37° C. in a humidified atmosphere of 6% $CO_2$. No matter which DNA construct was used in the transfection, 100 later each culture dish contained approximately $5 \times 10^6$ rat basophilic leukemia-1 cells.

Rat fibroblasts, mouse fibroblasts, and mouse WEHI-3 cells were transiently transfected with the plasmid DNA constructs using calcium phosphate (Avraham et al., J. Biol. Chem. 264:16719-16726 (1989); Southern et al., J. Mol. Appl. Gen. 1:327-341 (1982)). The cells ($1 \times 10^6$) were suspended in 2.5 ml of enriched medium, 0.2 ml of a 250 mM solution of calcium phosphate containing 5 μg of supercoiled plasmid DNA was added in a drop-wise manner, and the cultures were incubated overnight at 37° C. in a humidified atmosphere of 6% $CO_2$. The transfection media were removed the following day, and the cells were washed and cultured at 37° C. in 10 ml of fresh enriched medium in a humidified atmosphere of 6% $CO_2$. No matter which DNA construct was used in the transfection, 100 h later each culture dish contained approximately $4 \times 10^6$ fibroblasts. Approximately 100 h after the transfection by either method, 0.1 ml samples of culture medium were removed, and the levels of hGH were determined with an immunoassay kit from Nichols Institute Diagnostics (San Juan Capistrano, Calif.). The amounts of hGH in the culture media were determined by assaying the amounts of absorbed $^{125}I$-labeled anti-hGH antibody in the sandwich assays.

The results of the transfection assays were normalized for transfection efficiency using pXGH5. The amount of hGH produced by pXGH5 transfected cells was arbitrary assigned a value of 1, and then the relative amount hGH produced by each cell type transfected with the test plasmid was calculated as a ratio to that obtained with this control plasmid. In order to determine the promoter activity of various DNA constructs in dissimilar cell types transfected by different methods, a comparison of the relative amounts of hGH in the culture media for each cell type is preferable to a comparison of the absolute amounts of hGH (Sarid et al., J. Biol. Chem. 264:1022-1026 (1989)). It has been reported in other studies (Selden et al., Mol. Cell Biol. 6:3173-3179 (1986); Sarid et al., J. Biol. Chem. 264:1022-1026 (1989), Selden et al., Science 236:714-718 (1987)) that the amount of growth hormone produced by cells transfected with different hGH constructs is related to the amount of hGH mRNA in the transfected cells. To confirm that the variation in the amount of hGH in the culture media of cells transfected with the different constructs reflected a change in the level of hGH mRNA in the cells, total RNA was isolated from transfected rat basophilic leukemia-1 cells and rat-1 fibroblasts. Blots containing total RNA (10 μg/sample) were then prepared and probed with a $^{32}P$-labeled 950-bp BglII/EcoRI fragment of the hGH cDNA present in pΦGH.

4. DNA/Protein Binding Analyses—Nuclear extracts were prepared from rat basophilic leukemia-1 cells and rat-1 fibroblasts by a modification of the procedure described by Dignam and coworkers (Dignam et al., Nucleic Acids Res. 11:1475-1489 (1983)). Each preparation of pelleted cells ($10^8$) was washed once with 2.5 ml of ice-cold 10 mM Hepes (pH 7.9), 1.5 mM $MgCl_2$, 10 mM KCl, 1.0 mM dithiothreitol (DTT), 0.5 mM phenylmethylsulfonyl fluoride (PMSF), 0.1% leupeptin, 0.1% pepstatin, and 0.1% aprotonin. After a 10-min incubation at 4° C. in the same buffer, the cells were centrifuged for 3 min at $500 \times g$. The pelleted cells were resuspended in 1.0 ml of ice-cold buffer, lysed in a Dounce homogenizer, and centrifuged at 4° C. for 10 min at $900 \times g$ and then for 20 min at $16,000 \times g$. The supernatants were aspirated and the pelleted nuclear proteins were resuspended in 3 ml of 20 mM Hepes (pH 7.9), 25% glycerol, 1.5 mM $MgCl_2$, 0.42M NaCl, 0.2 mM EDTA, 0.5 mM DTT, 0.5 mM PMSF, 0.2% NP-40, 0.1% leupeptin, 0.1% pepstatin, and 0.1% aprotonin. The pellets were homogenized again in a Dounce homogenizer, agitated gently for 3 min, and centrifuged at 4° C. for 30 min at $100,000 \times g$. The solubilized nuclear proteins in each supernatant were dialyzed at 4° C. for 5 h against a 50-fold excess volume of 20 mM Hepes (pH 7.9), 20% glycerol, 0.1M KCl, 0.2 mM EDTA, 0.5 mM DTT, 0.5 mM PMSF, 0.1% leupeptin, 0.1% pepstatin, and 0.1% aprotonin, and then stored at −80° C. in this buffer. The protein concentration of each nuclear extract was determined by the Bradford method (Bradford, M. M., Anal. Biochem. 72:248-254 (1976)) using a Bio-Rad (Richmond, Calif.) protein assay kit with bovine serum albumin as standard.

DNA/protein-binding experiments were carried out in 20 μl of 10 mM Tris buffer (pH 7.5) containing 4% glycerol, 1 mM EDTA, 0.5 mM DTT, 0.1M NaCl, 4 μg of carrier poly(dI-dC) (Stratagene, La Jolla, Calif.), and 1 ng of a double-stranded $^{32}P$-end-labeled DNA probe corresponded to residues −250 to −161, residues −118 to −81, or residues −40 to +24 of the mouse serglycin gene (Avraham et al., J. Biol. Chem. 264:16719-16726 (1989)). In the binding competition assays, 5 ng of the specific serglycin-derived unlabeled oligonucleotide, 100 ng of unlabeled sonicated salmon sperm DNA, or 100 ng of a 64-mer unlabeled double-stranded oligonucleotide that binds transcription factors NF1/CTF, SP1, AP1, and AP3 (Stratagene Catalog No. 203001) was added to each reaction. After incubation at 25° C. for 30 min, gel mobility shift analyses were performed to detect the presence of specific DNA-binding proteins in the nuclear extracts. Samples were loaded onto a 5% non-denaturing polyacrylamide/bisacrylamide gel (30:1, w/w) that had been equilibrated before use by treatment for 1 h at 100 mA. The gels were run at 100 mA at 4° C. until the bromophenol blue tracking dye ran approximately two-thirds the length of the gel. The gels were then dried under vacuum and autoradiographed generally for 16 to 24 h.

Two control mixing experiments were used to confirm that the 89-bp probe corresponding to residues −250 to −161 of the mouse serglycin gene bound to distinct trans-acting factors in nuclear extracts of rat basophilic leukemia-1 cells and rat-1 fibroblasts. In the first experiment, $5 \times 10^7$ rat basophilic leukemia-1 cells and $5 \times 10^7$ rat-1 fibroblasts were mixed together, and then a nuclear extract of the pooled cells was prepared and analyzed in the gel mobility shift assay. In the second experiment, nuclear extracts were prepared separately from rat basophilic leukemia-1 cells and rat-1 fibroblasts and were mixed in 1:1, 2:1, or 3:1 proportions just before being analyzed in the gel mobility shift assay.

B. Identification by Deletion Analysis of Suppressors and Enhancers in the 5' Flanking Region of the Mouse Serglycin Gene To determine if the proximal 5' flanking region of the mouse serglycin gene contains cis acting regulatory elements, a DNA fragment that extends 504 bp upstream and 24 bp downstream of the gene's transcription-initiation site was linked to pΦGH. Preliminary experiments were performed (analyzing the kinetics of secretion and the stability of hGH) to optimize the transfection assay in rat basophilic leukemia-1 cells, WEHI-3 cells, rat fibroblasts, and mouse fibroblasts. No hGH was detected in any cell pellet, and therefore apparently all translated hGH was secreted. Additional experiments revealed that hGH was not degraded following its secretion into the culture media.

Rat basophilic leukemia-1 cells, mouse WEHI-3 cells, rat-1 fibroblasts, and mouse 3T3 fibroblasts were transiently transfected with the resulting plasmid construct, designated pPG(−504/+24)hGH. The results of the transfection experiments were normalized for transfection efficiency relative to that obtained with the reference plasmid pXGH5. As additional controls, cells were transfected with pSV40-hGH and pTKGH. As shown in Table III, the relative amount of hGH present in the 4-d conditioned medium of transfected mouse WEHI-3 cells and rat basophilic leukemia-1 cells was 20- to 18-fold higher than for transfected fibroblasts of the respective species. Therefore, the 504-bp region immediately upstream of the transcription-initiation site of the mouse serglycin gene contains cis-acting elements that preferentially enhance transcription of this gene in hematopoietic cells.

TABLE III

Relative human growth hormone (hGH) production by four cell lines that have been transiently transfected with control plasmids and a plasmid that contains the 5′ flanking region of the mouse serglycin gene fused to a promoterless human growth hormone gene.

| Plasmid Construct | Relative Expression of hGH* | | | rat basophilic leukemia-1 cells | Ratio | |
|---|---|---|---|---|---|---|
| | Mouse Fib. | Mouse WEHI-3 | Rat-1 Fib. | | WEHI-3/ Mouse Fib. | rat basophilic leukemia-1/ Rat Fib. |
| pXGH5 | 1.0 | 1.0 | 1.0 | 1.0 | 1.0 | 1.0 |
| pSV40-hGH | ND | ND | 0.29 ± 0.06 | 0.47 ± 0.16 | ND | 1.6 |
| pTKGH | 0.30 ± 0.05 | 0.11 ± 0.04 | ND | 0.72 ± 0.20 | 0.3 | ND |
| pPG(−504/+24)hGH | 0.01 ± 0.02 | 0.20 ± 0.05 | 0.04 ± 0.01 | 0.72 ± 0.12 | 20 | 18 |

Fib., fibroblasts; ND, not determined; rat basophilic leukemia-1, rat basophilic leukemia-1 cells; and WEHI-3, mouse myelomonocytic cells.
*Results are expressed as the mean ± SD of 5 to 6 experiments of 4 d duration, with each experiment performed on 2 replicate dishes of cells.

Figure 8A:
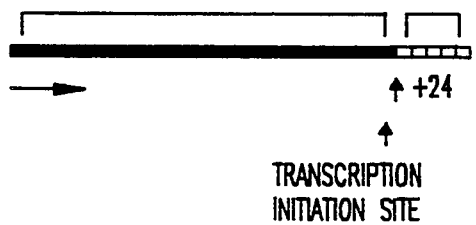
FIG. 8A. Effects of progressive deletion of the 5' flanking region of the mouse serglycin gene on its ability to direct human growth hormone (hGH) expression in transfected cells. The solid, bold horizontal lines (▬▬▬▬)represent the various lengths of the 5' flanking region of the mouse serglycin gene ligated to pΦGH, a plasmid that contains a promoterless hGH gene (▭▭▭▭). The negative and positive numbers in the various constructs refer to the length of the nucleotide sequence that extends upstream and downstream, respectively, of the transcription-initiation site of the gene. In each experiment, the amount of hGH was quantitated 4 d after transfection of rat basophilic leukemia-1 (RBL-1) cells and rat-1 fibroblasts with the specific plasmid construct. The numbers on the right are the hGH values obtained relative to the same population of cells transfected with the control plasmid construct, pXGH5. The indicated hGH activities represent the mean ±SD of data from 6 to 18 experiments. ND, not determined.

To locate more precisely these cis-acting elements, 9 additional plasmid constructs were prepared that had progressive deletions of the 5′ flanking region of this mouse gene fused to the hGH gene in pΦGH, as shown in FIG. 8A. Rat basophilic leukemia-1 cells and rat-1 fibroblasts transfected with constructs pPG(−423/+24)hGH, pPG(−333/+24)hGH, and pPG(−250/+24)hGH produced amounts of hGH comparable to the corresponding cells transfected with pXGH5. The production of hGH was enhanced ~2.5-fold when rat basophilic leukemia-1 cells were transfected with construct pPG(−190/+24) hGH; production of hGH was also enhanced when rat basophilic leukemia-1 cells were transfected with the pPG(−118/+24)hGH construct. When rat-1 fibroblasts were transfected with constructs pPG(−190/+24)hGH and pPG(−118/+24)hGH, production of hGH increased 21-fold and 24-fold, respectively. Therefore, at least one cis-acting element resides between −250 and −190 that suppresses transcription of the serglycin gene in cells, and this negative element is dominantly active in fibroblasts. Although rat basophilic leukemia-1 cells and rat-1 fibroblasts transfected with constructs pPG(−81/+24)hGH, pPG(−63/+24)hGH, and pPG(−40/+24)hGH produced some hGH, the amount was substantially less than that produced by cells transfected with construct pPG(−118/+24)hGH. Thus, at least one cis-acting element in the nucleotide sequence −118 to −81 constitutively enhances transcription of the serglycin gene in rat basophilic leukemia-1 cells and fibroblasts. When normalized for the efficiency of transfection, rat basophilic leukemia-1 cells transfected with construct pPG(−118/+24)hGH produced 2.7-fold (p<0.05) more hGH than similarly transfected fibroblasts, indicating that the enhancer between residues −118 and −81 is more dominantly active in rat basophilic leukemia-1 cells than in fibroblasts. Because no hGH was produced by rat basophilic leukemia-1 cells or rat-1 fibroblasts transfected with construct pPG(−20/+24)hGH, the proximal element in the promoter region of this gene must reside between −40 and −20.

Figure 8B:
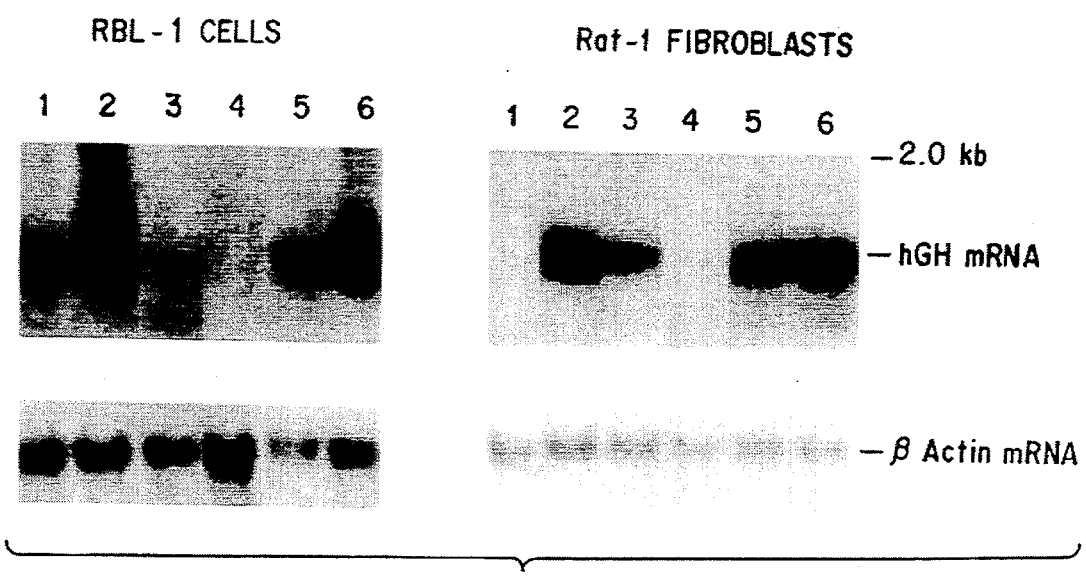
FIG. 8B. Blot analysis of hGH mRNA in rat basophilic leukemia-1 cells and rat-1 fibroblasts transfected with different DNA constructs. RNA blots containing approximately equal amounts of total RNA (10 μg/sample) from rat basophilic leukemia-1 cells and rat-1 fibroblasts transfected with pPG(−504/+24)hGH (lane 1), pPG(−118/+24)hGH (lane 2), pPG(−40/+24)hGH (lane 3), pΦGH (lane 4), pSV40-hGH (lane 5), or pXGH5 (lane 6) were probed with a $^{32}$P-labeled hGH cDNA. The arrows on the right indicate the migration positions of 2.0 kb rRNA, hGH mRNA, and β-actin mRNA. pSV40-hGH was obtained by Dr. J. Sarid, Brigham and Women's Hospital and Harvard Medical School, Boston, Mass.

As assessed by RNA blot analysis (FIG. 8B), rat basophilic leukemia-1 cells contained abundant amounts of hGH mRNA when transfected with pPG(−504/+24)hGH, pPG(−118/+24)hGH, pSV40-hGH, or pXGH5. A lesser amount of hGH mRNA was present in rat basophilic leukemia-1 cells transfected with pPG(−40/+24)hGH, and no hGH mRNA was detected in cells transfected with pΦGH. Rat-1 fibroblasts contained abundant amounts of hGH mRNA when transfected with pPG(−118/+24) hGH, pSV40-hGH, or pXGH5, but the amount was below detection when transfected with pPG(−504/+24)hGH or pΦGH (FIG. 8B). The level of hGH mRNA in rat-1 fibroblasts transfected with pPG(−40/+24)hGH was less than replicate fibroblasts transfected with pPG(−118/+24 )hGH.

Figure 9:
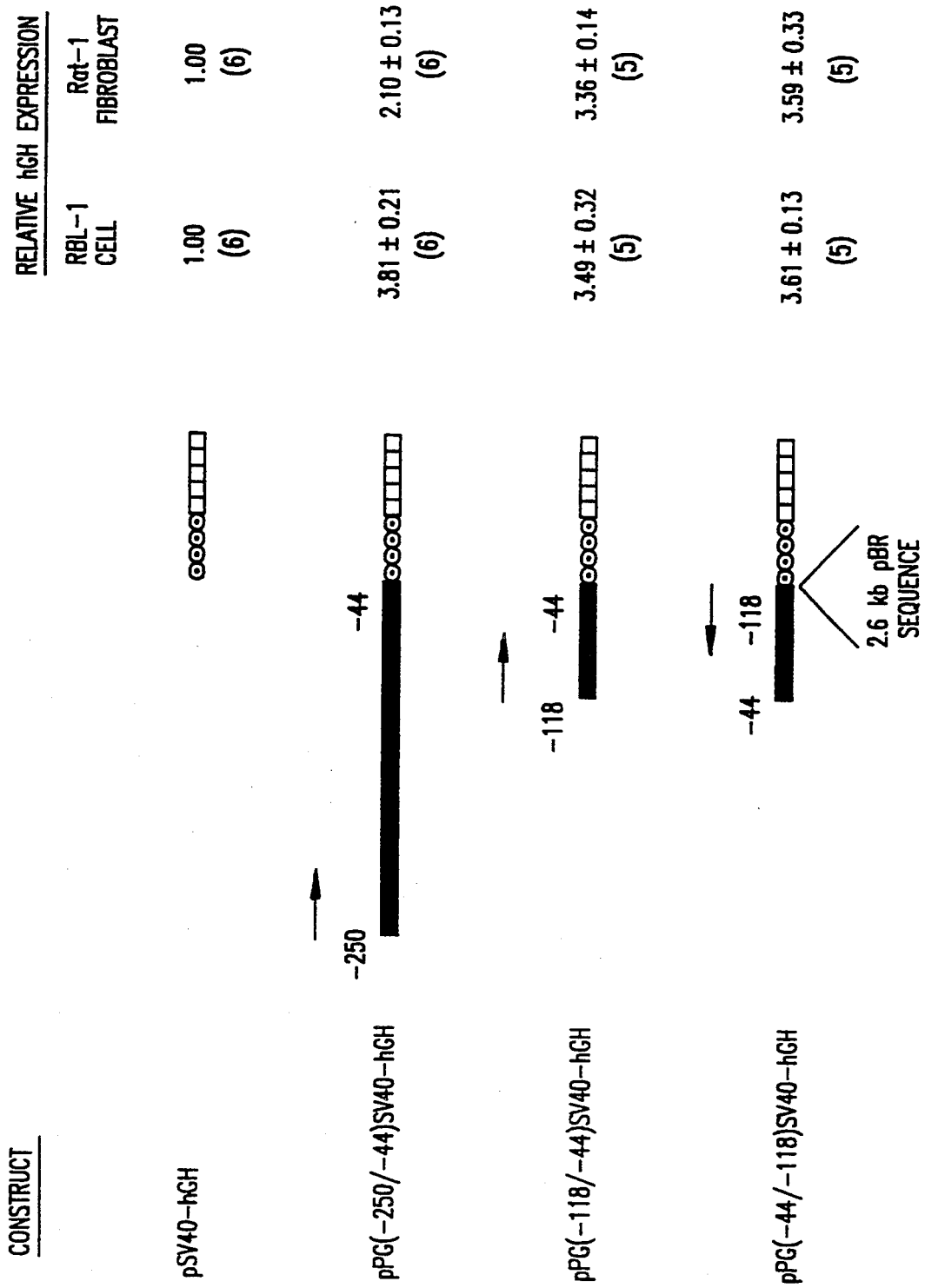
FIG. 9. Effect of two 5' flanking regions of the mouse serglycin gene on its ability to enhance and suppress hGH production in cells transfected with plasmid constructs that contain an enhancerless SV40 early promoter. The hatched lines (▭▭▭▭) and the round-dot lines (o o o o) represent the structural sequences of the hGH gene and SV40 early promoter, respectively, within the plasmid construct. The solid, bold horizontal lines (▬▬▬▬) represent the specific parts of the 5' flanking-region of the mouse serglycin gene that is inserted upstream of the SV40 promoter in pSV40-hGH.

To determine if the positive cis-acting element in residues −118 to −44 of the mouse serglycin gene functions as an enhancer and to confirm that the negative cis-acting element resides upstream of the enhancer, two 5′ flanking regions of the gene were ligated into pSV40-hGH to create constructs pPG(−250/−44)SV40-hGH and pPG(−118/−44)SV40-hGH (FIG. 9). Rat basophilic leukemia-1 cells and rat-1 fibroblasts were then transfected with pSV40-hGH or with one of the two plasmid constructs, and the relative levels of hGH in the culture media were determined. Greater than 3-fold more hGH was detected in the culture medium of rat basophilic leukemia-1 cells and rat-1 fibroblasts transfected with pPG(−118/−44)SV40-hGH relative to pSV40-hGH, indicating the enhancer in this 5′ flanking region of the gene functions as an enhancer. This regulatory element also induced rat basophilic leukemia-1 cells and rat-1 fibroblast to produce ~3.6-fold more hGH when linked in the plasmid in its opposite orientation 2.6 kb upstream of the SV40 early promoter (FIG. 9). The finding that the level of hGH produced by fibroblasts transfected with pPG(−250/−44)SV40-hGH is approximately one-half that of fibroblasts transfected with pPG(−118/−44)SV40-hGH again indicates that there is a negative cis-acting element within the more distal 5′ flanking region of the mouse serglycin gene that is active in fibroblasts.

C. Identification of the Proximal Region of the Promoter of the Mouse Serglycin Gene by Site-Directed Mutagenesis—Although no classical TATA box is present ~30 bp 5′ of the transcription-initiation site of the mouse or human serglycin gene, ACCTCTTT-CTAAAAGGG [SEQ ID No. 5] sequence is present beginning 22 nucleotides upstream of the transcription-initiation site. Site-directed mutagenesis was performed to determine whether or not this region was part of the proximal promoter of the gene. Constructs were prepared in which the adenosine at −28 of pPG(−504/+24)hGH was converted into a cytosine, the cytosine at residue −30 was converted into an adenosine, or the adenosine at −38 was converted into a guanosine (Table IV). Relative to cells transfected with pPG(−504/+24)hGH, substantially less hGH was produced by rat-1 fibroblasts and rat basophilic leukemia-1 cells transfected with any one of the three mutated constructs. The greatest inhibition occurred with the construct that had a mutated residue −30.

TABLE IV

Relative human growth hormone (hGH) production by rat basophilic leukemia-1 cells and rat-1 fibroblasts transfected with constructs containing a normal and mutated proximal promoter region of the mouse serglycin gene.

| Nucleotide Sequence | Mutation Position | Relative Expression of hGH* | |
|---|---|---|---|
| | | rat basophilic leukemia-1 cells | Rat-1 fibroblasts |
| ACCTCTTTCTAAAAGGG (native) [SEQ ID No. 5] | None | 1.00 | 1.00 |
| ACCTCTTTCT$\underline{C}$AAAGGG (mutated) [SEQ ID No. 6] | −28 bp | 0.32 ± 0.04 | 0.38 ± 0.06 |
| ACCTCTTT$\underline{A}$TAAAAGGG (mutated) [SEQ ID No. 7] | −30 bp | 0.09 ± 0.02 | 0.17 ± 0.03 |
| $\underline{G}$CCTCTTTCTAAAAGGG (mutated) [SEQ ID No. 8] | −38 bp | 0.43 ± 0.02 | 0.69 ± 0.02 |

*Results are expressed as the mean ± ½ range of two experiments with each experiment performed on 8 replicate dishes of cells.

Protein/DNA binding Analyses—Gel mobility shift assays were used to determine whether or not rat basophilic leukemia-1 cells and rat-1 fibroblasts contain trans-acting factors in their nuclei that bind specifically to the three identified cis-acting regulatory elements in the 5′ flanking region of the mouse serglycin gene. An 89-bp $^{32}$P-labeled DNA fragment containing the putative suppressor and corresponding to residues −250 to −161 of the mouse serglycin gene was gel electrophoresed before and after it had been incubated with the nuclear extracts from rat basophilic leukemia-1 cells and rat-1 fibroblasts. As shown in FIG. 10 for one of four experiments, in the absence of nuclear extract, the radioactive probe migrated to its expected position at the bottom of the gel (lane 1). When the $^{32}$P-labeled probe was incubated with the nuclear extracts from either one of the two populations of cells before electrophoresis, it was selectively retained in the gel by a putative DNA-binding protein (designated B/F$_{(-250/-161)}$-I) (lanes 2 and 5). The binding of this $^{32}$P-labeled oligonucleotide to B/F$_{(-250/-161)}$-I was specific because retention of the probe was diminished when a 5-fold excess of the same nonradioactive DNA fragment was included in the assay (lanes 3 and 6); retention was not diminished when a 100-fold excess of sonicated salmon sperm DNA (lanes 4 and 7) or the 64-mer oligonucleotide that binds NF1/CTF, SP1, AP1, and AP3 was included in the assay. Based on its differential mobility in this gel mobility shift assay, a second trans-acting factor (F$_{(250/-161)}$-II) was detected only in the nuclear extracts of rat-1 fibroblasts. Because rat basophilic leukemia-1 cells, but not fibroblasts, contain proteases in their secretory/granules (one of which is a chymase active at neutral pH (Seldin et al., Proc. Natl Acad. Sci. USA 82:3871-3875 (1985))), two control experiments were carried out to determine if the absence of F$_{(-250/-161)}$-II in rat basophilic leukemia-1 cells was a consequence of the isolation procedure used to obtain the nuclear DNA-binding proteins. When the nuclear extracts from rat basophilic leukemia-1 cells and fibroblasts were mixed in different proportions before analysis, the level of F$_{(-250/-161)}$-II detected in the gel mobility shift assay varied according to the amount of fibroblast-derived nuclear protein that was used in the assay. Furthermore, the amounts of B/F$_{(-250/-161)}$-I and F$_{(-250/-161)}$-II detected in the nuclear extract of a pooled preparation of rat basophilic leukemia-1 cells and fibroblasts were compatible with the results of the extracts of the individual cell types. Thus, the absence of F$_{(-250/-161)}$-II in the nuclear extracts of rat basophilic leukemia-1 cells was not a consequence of preferential proteolysis of this trans-acting factor in rat basophilic leukemia-1 cells.

A 37-bp $^{32}$P-labeled DNA fragment containing the putative enhancer element and corresponding to residues −118 to −81 of the mouse serglycin gene was gel electrophoresed before and after it had been incubated with the nuclear extracts from rat basophilic leukemia-1 cells and rat-1 fibroblasts. As shown in FIG. 11 for one of 3 experiments, a retarded species (B$_{(-118/-81)}$-I) was obtained when the $^{32}$P-labeled oligonucleotide was incubated with rat basophilic leukemia-1 cell-derived nuclear extracts (lane 2). B$_{(-118/-81)}$-I possessed a mobility different from that of the retarded species, F$_{(-118/-81)}$-I, present in the nuclear extracts of rat-1 fibroblasts (lane 5). The ability to inhibit binding of the $^{32}$P-labeled oligonucleotide to B$_{(-118/-81)}$-I and to F$_{(-118/-18)}$-I with a 5-fold excess of the same nonradioactive DNA probe (lanes 3 and 6), but not with a 100-fold excess of sonicated salmon sperm DNA (lanes 4 and 7) or the 64-mer oligonucleotide that binds NF1/CTF, SP1, AP1, and AP3 (data not shown), indicated that these interactions were specific. Although an additional retarded species was observed in this gel mobility shift assay when either nuclear extract was used, its binding could not be inhibited by an excess of the specific nonradioactive oligonucleotide.

A 64-bp $^{32}$P-labeled DNA fragment containing the putative proximal promoter element and corresponding to residues −40 to +24 of the mouse serglycin gene was also gel electrophoresed before and after it had been incubated with the nuclear extracts from rat basophilic leukemia-1 cells and rat-1 fibroblasts. As shown in FIG. 12 for one of 3 experiments, when the $^{32}$P-labeled probe was incubated with the nuclear extracts from either one of the two populations of cells before electrophoresis, a new species, designated B/F$_{(-40/+24)}$-I, was observed that migrated more slowly in the gel (lanes 2 and 7). The binding of this migrated oligonucleotide to B/F$_{(-40/+24)}$-I could be competitively inhibited by a 5-fold excess of the same nonradioactive DNA probe (lanes 3 and 8), but not by a 100-fold excess of sonicated salmon sperm DNA or the oligonucleotide that binds NF1/CTF, SP1, AP1, and AP3. Additional distinct trans-acting factors, designated F$_{(-40/+24)}$-II and B$_{(-40/+24)}$-II, were detected in the nuclear extracts of rat-1 fibroblasts and rat basophilic leukemia-1 cells, respectively. The binding of this 64-bp serglycin proteoglycan-derived $^{32}$P-labeled probe to F$_{(-40/+24)}$-II, B/F$_{(-40/+24)}$-I, and B$_{(-40/+24)}$-II was minimally diminished in the competition assay when nonradioactive DNA that had a mutated residue −28, −30, or −38 was used in a 50-fold excess over the nonmutated $^{32}$P-labeled probe (FIG. 12).

EXAMPLE 10

Methylation of the Human Serglycin Gene

The serglycin gene-derived Alu sequences were aligned with the Alu consensus nucleotide sequence of Jurka, J. et al., Proc. Natl. Acad. Sci. USA 85:4775–4778 (1988); their locations and characteristics are depicted in FIG. 13A and Table V.

TABLE V

Distribution and Type of Alu Elements in the Human Serglycin Gene

Twenty-one Alu elements were detected in the nucleotide seuqence of the human serglycin gene (FIG. 13A). Of these, 10 were identified in the introns. Thirteen were of the S type, and 8 were of the J type. In two instances, only approximately one-half of an Alu element was inserted in the gene. These elements were oriented in the sense (F) or anti-sense (R) direction relative to ther est of the human serglycin gene.

| Number | Location | Type | Direction |
|---|---|---|---|
| 1 | 5'-flanking region | S | R |
| 2 | 5'-flanking region | S | F |
| 3 | Intron 1 | S | F |
| 4 | Intron 1 | S | F |
| 5 | Intron 1 | S | F |
| 6 | Intron 1 | S | F |
| 7 | Intron 1 | J | R |
| 8 | Intron 1 | S | F |
| 9 | Intron 1 | S | F |
| 10 | Intron 1 | J | F |
| 11 | Intron 2 | J | R |
| 12 | Intron 2 | S | R |
| 13 | Intron 2 | J (½) | F |
| 14 | Intron 2 | J | F |
| 15 | Intron 2 | J | R |
| 16 | Intron 2 | J (½) | F |
| 17 | Intron 2 | S | F |
| 18 | Intron 2 | S | R |
| 19 | Intron 2 | J | F |
| 20 | Intron 2 | S | R |
| 21 | Intron 2 | S | F |

Fifteen diagnostic positions were examined to determine if the Alu elements were of the "S" or the "J" subfamily. Because the J subfamily of Alu elements is more similar to 7SL RNA than the S subfamily, the J type probably is a more primitive Alu element. Eleven of the Alu elements were of the S type, whereas eighth were of the J type. The two Alu elements in the 5'flanking region were of the S type. The Alu elements were present in both orientations. Thirteen were oriented in the sense direction of the gene's exons; whereas the other six were orientated in the anti-sense direction.

The deduced nucleotide sequence of the human serglycin gene was used to determine the methylation pattern of this gene in cells that do and do not transcribe it.

Because of their hybridization to corresponding regions within other genes, it was not possible to probe genomic DNA blots with short DNA fragments of the human serglycin gene that contained Alu DNA sequences. Thus, knowledge of the exact location of the Alu repetitive elements within the serglycin gene (FIG. 13A) permitted the avoidance of those sequences in the methylation study. Because HL-60 cells, but not Molt-4 cells, contain serglycin mRNA, DNA was isolated from these two cell types and the methylation patterns of their seglycin genes determined. The location of all of the sites susceptible to HpaII and MspI within the human serglycin gene were determined (FIG. 13B) and PCT methodology was used to construct 13 probes (designated A–M) to determine how many of these 5'-CCGG-3' sequences contained an internal 5' methylcytosine.

Human genomic DNA was prepared as described by Sambrook et al., Molecular Cloning: A Laboratory Manual, 2nd ed., pp. 9.16–9.19 (1989), Cold Spring Harbor Laboratory, Cold Spring Harbor, N.Y. HL-60 cells and Molt-4 cells were each centrifuged at 1500×g for 10 min at 4° C. The supernatants were removed, and the cells were washed twice with ice-cold 0.14M NaCl, 2.7 mM KCl, 25 mM Tris, pH 7.4. The cells were suspended in 10 mM Tris, pH 8.0, containing 0.1M EDTA, 0.5% SDS, and 20 μg/ml pancreatic RNase and were incubated for 1 hour at 37° C. After Proteinase K (100 μg/ml) treatment under standard conditions, the digests were extracted 4 times with Tris-saturated phenol and then with chloroform. The genomic DNAs in the resulting solutions were precipitated with ethanol. Samples containing about 10 μg jof DNA either were dissolved in 10 mM MgCl$_2$ and 20 mM Tris, pH 7.4, and digested with Hpa II (GIBCO-BRL), or were dissolved in 10 mM MgCl$_2$ and 50 mM Tris, pH8.0, and digested with MspI (GIBCO-BRL). These two restriction enzymes both cleave the unmethylated nucleotide sequence 5'-CCGG-3', but only MspI cleaves this sequence if the internal C is 5 methylcytosine (Waalwijk, C., and Flavell, R. A., Nucleic Acids Res. 5:3231–3236 (1976)). The digests were electrophoresed in 1% agarose gels and transferred (Southern, E. M., J. Mol. Biol. 98:503–517 (1975)) to Duralon membranes (Stratagene). The resulting DNA blots were hybridized with random-primed, PCR-derived, 250–880-bp probes that correspond to 13 different regions of the human sergly-cin gene. These DNA probes were generated with either the HL-60 cell-derived serglycin cDNA (Stevens et al., J. Biol. Chem. 203:7287–7291 (1988)) or the serglycin genomic subclones (Nicodemus et al., J. Biol. Chem. 265:5889–5896 (1990)) as templates. The probes used in this methylation study were specific to the human serglycin gene because each hybridized to a single genomic fragment.

When blots containing digested genomic DNA from HL-60 cells were analyzed with the intron 1 probes A–F, each probe hybridized to a DNA fragment in the MspI digest that was identical in size with the corresponding fragment in the HpaII digest. Therefore, the 5'-flanking region and intron 1 of the serglycin gene were both hypomethylated in HL-80 cells. Like the intron 1 probes, the intron 2 probe J hybridized to identically sized fragments in the HpaII and MspI digests of genomic DNA from HL-60 cells. In contrast, several of the other sites in intron 2 of the serglycin gene were at least partially methylated in HL-60 cells. Which of the five HpaII/MspI sites at the 3' end of this gene are methylated could not be conclusively determined because of their proximity to one another, but probes K and M both hybridized to larger DNA fragments in the HpaII digest, as compared with the MspI digest. Thus, some, if not all, of these sites at the 3' end of the serglycin gene are methylated in HL-60 cells. Whereas probes G, H, and I all hybridized to the expected size of DNA fragments after digestion of genomic DNA with MspI, they hybridized to two to three fragments after digestion with HpaII. The presence of a 3.2-kb DNA fragment that hybridizes to both probe H and probe I argues that the HpaII sites that reside at 11.5 and 11.8 kb in the serglycin gene are methylated in most HL-60 cells. In a second experiment, these two sites were methylated in almost all of the HL-60 cells in the culture. Exon 2 probe G hybridized to two approximately equal fragments in the HpaII-digest, indicating that the HpaII/MspI site at 9.5 kb in the serglycin gene was methylated in approximately 50% of the HL-60 in the culture. These findings are not the result of incomplete digestion of the DNA samples of nonspecific hybridization of the probes with a fragment from another gene because the same blot yielded single bands after hybridization with other probes and because single bands were detected when MspI-digested genomic DNAs were analyzed with these same serglycin-derived probes.

In contrast to the gene in HL-60 cells, the serglyein gene in Molt-4 cells was highly methylated. Probing with any of the PCR-derived DNA fragments yielded DNA genomic fragments of >10 kb, indicating that most, if not all, of the HpaII sites in the serglycin gene of Molt-4 cells were methylated.

Several genes have been reported preferentially to contain cis-acting regulatory elements in their first introns. Although it has not been determined if the transcription-regulatory activities of any of these elements in intron-1 are effected by methylation, it has been shown that CpG methylation of the cAMP response element found in the promoters of many genes abolishes its transcriptional regulatory activity (Iguchi-Ariga, S.M.M. et al., Genes & Dev. 3:612–619 (1989)). The diminished methylation of the first intron of the serglycin gene in a cell that contains abundant levels of this transcript, but not in a cell that does not transcribe the gene, suggests that specific methylation-dependent nucleotide sequences in intron 1 act in concert with the identified sequences in the 5'-flanking region (Avraham, S. et al., J. Biol. Chem. 207:610–617 (1992)) to regulate transcription of the serglycin gene in different cell types.

All references cited herein are incorporated herein fully by reference. Having now fully described the invention, it will be understood by those with skill in the art that the scope may be performed within a wide and equivalent range of conditions, parameters and the like, without affecting the spirit or scope of the invention or any embodiment thereof.

---

What is claimed is:

1. An isolated DNA sequence consisting essentially of the 5' regulatory region of the human or mouse serglycin gene, said regulatory region comprising:
   a. the promoter element of said mouse serglycin gene (SEQ ID No. 17) or the equivalent position in said human serglycin gene (nucleotides 585–604 of SEQ ID No. 11);
   b. the negative transcriptional regulatory element of said mouse serglycin gene (SEQ ID No. 18) or the equivalent position in said human serglycin gene (nucleotides 396–432 of SEQ ID No. 11);
   c. the positive transcriptional regulatory element of said mouse serglycin gene (SEQ ID No. 16) or the equivalent position in said human serglycin gene (nucleotides 508–545 of SEQ ID No. 11).

2. The sequence of claim 1, wherein said serglycin gene is the human gene.

3. The sequence of claim 2, wherein said sequence consists essentially of bases 373 through 622 of SEQ ID No. 11.

4. The sequence of claim 1, wherein said serglycin gene is the mouse gene.

5. The sequence of claim 4, wherein said sequence consists essentially of bases 255 through 504 of SEQ ID No. 13.

6. An isolated DNA sequence consisting essentially of the negative transcriptional regulatory element located between nucleotides −250 and −190 of the human or mouse serglycin gene, and said element being dominantly active to inhibit transcription of operably linked genes in fibroblast hosts.

7. The sequence of claim 6, wherein said element is from the mouse serglycin gene.

8. The sequence of claim 7, wherein said element consists essentially of SEQ ID No. 18.

9. The sequence of claim 6, wherein said element is from the human serglycin gene.

10. The sequence of claim 9, wherein said element consists essentially of bases 396 through 432 of SEQ ID No. 11.

11. An isolated DNA sequence consisting essentially of the enhancer transcriptional regulatory element located between nucleotides −118 and −77 of the human or mouse serglycin gene, and said element being dominantly active to stimulate transcription of operably linked genes in hematopoietic cells.

12. The sequence of claim 11, wherein said element is from the mouse hematopoietic serglycin gene.

13. The sequence of claim 12, wherein said element consists essentially of SEQ ID NO. 16.

14. The sequence of claim 11, wherein said element is from the human serglycin gene.

15. The sequence of claim 14, wherein said element consists essentially of bases 508–545 of SEQ ID No. 11.

16. An isolated DNA sequence consisting essentially of the eukaryotic promoter element located between nucleotides −40 and −19 of the human or mouse serglycin gene, and said element being dominantly active for the promotion of transcription in operably linked genes in hematopoietic cells.

17. The sequence of claim 16, wherein said element is from the mouse serglycin gene.

18. The sequence of claim 17, wherein said element consists essentially of SEQ ID No. 17.

19. The sequence of claim 16, wherein said element is from the human serglycin gene.

20. The sequence of claim 19, wherein said element consists essentially of bases 585–604 of SEQ ID No. 11.

21. A DNA expression vector comprising the DNA sequence of any of claims 1–20.

22. The expression vector of claim 21, wherein said vector is a plasmid.

23. The expression vector of claim 22, wherein said vector is an *E. coli*/mammalian cell shuttle vector.

24. The expression vector of claim 21, wherein said DNA sequence is operably linked to a gene of interest.

25. A host cell transformed with the DNA expression vector of claim 21.

26. A host cell transformed with the DNA expression vector of claim 24.

27. The host cell of claim 24, wherein said host is a hematopoietic cell.

28. The host cell of claim 24, wherein said host is a fibroblast.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 271 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:1:

```
GAATTCTTAA AGGATTATGC TTTAATGCTG TTATCTATCT TATTGTTCTT GAAAATACCT      60

GCATTTTTTG GTATCATGTT CAACCAACAT CATTATGAAA TTAATTAGAT TCCCATGGCC     120

ATAAAATGGC TTTAAAGAAT ATATATATAT TTTTAAAGTA GCTTGAGAAG CAAATTGGCA     180

GGTAATATTT CATACCTAAA TTAAGACTCT GACTTGGATT GTGAATTATA ATGATATGCC     240

CCTTTTCTTA TAAAAACAAA AAAAAAATAA T                                    271
```

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:2:

```
CTTGAACTGA GGATTCCAGA A                                                21
```

( 2 ) INFORMATION FOR SEQ ID NO:3:

( i ) SEQUENCE CHARACTERISTICS:
                ( A ) LENGTH: 16 amino acids
                ( B ) TYPE: amino acid
                ( C ) STRANDEDNESS: both
                ( D ) TOPOLOGY: linear ( i i ) MOLECULE TYPE: peptide ( x i ) SEQUENCE DESCRIPTION: SEQ ID NO:3:

```
Ser  Asn  Lys  Ile  Pro  Arg  Leu  Arg  Thr  Asp  Leu  Phe  Pro  Lys  Thr  Arg
1                  5                        10                       15
```

( 2 ) INFORMATION FOR SEQ ID NO:4:

( i ) SEQUENCE CHARACTERISTICS:
                ( A ) LENGTH: 16 amino acids
                ( B ) TYPE: amino acid
                ( C ) STRANDEDNESS: both
                ( D ) TOPOLOGY: linear ( i i ) MOLECULE TYPE: peptide ( x i ) SEQUENCE DESCRIPTION: SEQ ID NO:4:

```
Ser  Val  Gln  Gly  Tyr  Pro  Thr  Gln  Arg  Ala  Arg  Tyr  Gln  Trp  Val  Arg
1                  5                        10                       15
```

( 2 ) INFORMATION FOR SEQ ID NO:5:

( i ) SEQUENCE CHARACTERISTICS:
                ( A ) LENGTH: 17 base pairs
                ( B ) TYPE: nucleic acid
                ( C ) STRANDEDNESS: both
                ( D ) TOPOLOGY: linear ( i i ) MOLECULE TYPE: DNA ( x i ) SEQUENCE DESCRIPTION: SEQ ID NO:5:

ACCTCTTTCT AAAAGGG                                                           17

( 2 ) INFORMATION FOR SEQ ID NO:6:

( i ) SEQUENCE CHARACTERISTICS:
                ( A ) LENGTH: 17 base pairs
                ( B ) TYPE: nucleic acid
                ( C ) STRANDEDNESS: both
                ( D ) TOPOLOGY: linear ( i i ) MOLECULE TYPE: DNA ( x i ) SEQUENCE DESCRIPTION: SEQ ID NO:6:

ACCTCTTTCT CAAAGGG                                                           17

( 2 ) INFORMATION FOR SEQ ID NO:7:

( i ) SEQUENCE CHARACTERISTICS:
                ( A ) LENGTH: 17 base pairs
                ( B ) TYPE: nucleic acid
                ( C ) STRANDEDNESS: both
                ( D ) TOPOLOGY: linear ( i i ) MOLECULE TYPE: DNA ( x i ) SEQUENCE DESCRIPTION: SEQ ID NO:7:

ACCTCTTTAT AAAAGGG                                                           17

( 2 ) INFORMATION FOR SEQ ID NO:8:

( i ) SEQUENCE CHARACTERISTICS:
                ( A ) LENGTH: 17 base pairs
                ( B ) TYPE: nucleic acid
                ( C ) STRANDEDNESS: both ( D ) TOPOLOGY: linear ( i i ) MOLECULE TYPE: DNA ( x i ) SEQUENCE DESCRIPTION: SEQ ID NO:8:

GCCTCTTTCT AAAAGGG                                                                                  17

( 2 ) INFORMATION FOR SEQ ID NO:9:

( i ) SEQUENCE CHARACTERISTICS:
        ( A ) LENGTH: 659 base pairs
        ( B ) TYPE: nucleic acid
        ( C ) STRANDEDNESS: both
        ( D ) TOPOLOGY: linear ( i i ) MOLECULE TYPE: DNA ( i x ) FEATURE:
        ( A ) NAME/KEY: CDS
        ( B ) LOCATION: 32..508

( x i ) SEQUENCE DESCRIPTION: SEQ ID NO:9:

```
GTGCAGCTGG GAGAGCTAGA CTAAGTTGGT C ATG ATG CAG AAG CTA CTC AAA         52
                                  Met Met Gln Lys Leu Leu Lys
                                   1               5

TGC AGT CGG CTT GTC CTG GCT CTT GCC CTC ATC CTG GTT CTG GAA TCC       100
Cys Ser Arg Leu Val Leu Ala Leu Ala Leu Ile Leu Val Leu Glu Ser
         10                  15                  20

TCA GTT CAA GGT TAT CCT ACG CAG AGA GCC AGG TAC CAA TGG GTG CGC       148
Ser Val Gln Gly Tyr Pro Thr Gln Arg Ala Arg Tyr Gln Trp Val Arg
     25                  30                  35

TGC AAT CCA GAC AGT AAT TCT GCA AAC TGC CTT GAA GAA AAA GGA CCA       196
Cys Asn Pro Asp Ser Asn Ser Ala Asn Cys Leu Glu Glu Lys Gly Pro
 40                  45                  50                  55

ATG TTC GAA CTA CTT CCA GGT GAA TCC AAC AAG ATC CCC CGT CTG AGG       244
Met Phe Glu Leu Leu Pro Gly Glu Ser Asn Lys Ile Pro Arg Leu Arg
                 60                  65                  70

ACT GAC CTT TTT CCA AAG ACG AGA ATC CAG GAC TTG AAT CGT ATC TTC       292
Thr Asp Leu Phe Pro Lys Thr Arg Ile Gln Asp Leu Asn Arg Ile Phe
             75                  80                  85

CCA CTT TCT GAG GAC TAC TCT GGA TCA GGC TTC GGC TCC GGC TCC GGC       340
Pro Leu Ser Glu Asp Tyr Ser Gly Ser Gly Phe Gly Ser Gly Ser Gly
         90                  95                 100

TCT GGA TCA GGA TCT GGG AGT GGC TTC CTA ACG GAA ATG GAA CAG GAT       388
Ser Gly Ser Gly Ser Gly Ser Gly Phe Leu Thr Glu Met Glu Gln Asp
     105                 110                 115

TAC CAA CTA GTA GAC GAA AGT GAT GCT TTC CAT GAC AAC CTT AGG TCT       436
Tyr Gln Leu Val Asp Glu Ser Asp Ala Phe His Asp Asn Leu Arg Ser
 120                 125                 130                 135

CTT GAC AGG AAT CTG CCC TCA GAC AGC CAG GAC TTG GGT CAA CAT GGA       484
Leu Asp Arg Asn Leu Pro Ser Asp Ser Gln Asp Leu Gly Gln His Gly
                 140                 145                 150

TTA GAA GAG GAT TTT ATG TTA TAAAGAGGA TTTTCCCACC TTGACACCAG           535
Leu Glu Glu Asp Phe Met Leu
                 155

GCAATGTAGT TAGCATATTT TATGTACCAT GGTTATATGA TTAATCTTGG GACAAAGAAT     595

TTTATAGAAA TTTTTAAACA TCTGAAAAAG AAGCTTAAGT TTTATCATCC TTTTTTTTC      655

TCAT                                                                  659
```

( 2 ) INFORMATION FOR SEQ ID NO:10:

( i ) SEQUENCE CHARACTERISTICS:
        ( A ) LENGTH: 158 amino acids
        ( B ) TYPE: amino acid (D) TOPOLOGY: linear (ii) MOLECULE TYPE: protein (xi) SEQUENCE DESCRIPTION: SEQ ID NO:10:

| Met | Met | Gln | Lys | Leu | Leu | Lys | Cys | Ser | Arg | Leu | Val | Leu | Ala | Leu | Ala |
|---|---|---|---|---|---|---|---|---|---|---|---|---|---|---|---|
| 1 | | | | 5 | | | | 10 | | | | | | 15 | |
| Leu | Ile | Leu | Val | Leu | Glu | Ser | Ser | Val | Gln | Gly | Tyr | Pro | Thr | Gln | Arg |
| | | | 20 | | | | | 25 | | | | | 30 | | |
| Ala | Arg | Tyr | Gln | Trp | Val | Arg | Cys | Asn | Pro | Asp | Ser | Asn | Ser | Ala | Asn |
| | | 35 | | | | | 40 | | | | | 45 | | | |
| Cys | Leu | Glu | Glu | Lys | Gly | Pro | Met | Phe | Glu | Leu | Leu | Pro | Gly | Glu | Ser |
| | 50 | | | | | 55 | | | | | 60 | | | | |
| Asn | Lys | Ile | Pro | Arg | Leu | Arg | Thr | Asp | Leu | Phe | Pro | Lys | Thr | Arg | Ile |
| 65 | | | | | 70 | | | | 75 | | | | | | 80 |
| Gln | Asp | Leu | Asn | Arg | Ile | Phe | Pro | Leu | Ser | Glu | Asp | Tyr | Ser | Gly | Ser |
| | | | | 85 | | | | | 90 | | | | | 95 | |
| Gly | Phe | Gly | Ser | Gly | Ser | Gly | Ser | Gly | Ser | Gly | Ser | Gly | Ser | Gly | Phe |
| | | | 100 | | | | | 105 | | | | | 110 | | |
| Leu | Thr | Glu | Met | Glu | Gln | Asp | Tyr | Gln | Leu | Val | Asp | Glu | Ser | Asp | Ala |
| | | | 115 | | | | | 120 | | | | | 125 | | |
| Phe | His | Asp | Asn | Leu | Arg | Ser | Leu | Asp | Arg | Asn | Leu | Pro | Ser | Asp | Ser |
| | 130 | | | | | 135 | | | | | 140 | | | | |
| Gln | Asp | Leu | Gly | Gln | His | Gly | Leu | Glu | Glu | Asp | Phe | Met | Leu | | |
| 145 | | | | | 150 | | | | | 155 | | | | | |

(2) INFORMATION FOR SEQ ID NO:11:

(i) SEQUENCE CHARACTERISTICS:
(A) LENGTH: 1706 base pairs
(B) TYPE: nucleic acid
(C) STRANDEDNESS: both
(D) TOPOLOGY: linear (ii) MOLECULE TYPE: DNA (ix) FEATURE:
(A) NAME/KEY: CDS
(B) LOCATION: join(675..753, 820..967, 1036..1282)

(ix) FEATURE:
(A) NAME/KEY: exon
(B) LOCATION: 622..753

(ix) FEATURE:
(A) NAME/KEY: exon
(B) LOCATION: 820..967

(ix) FEATURE:
(A) NAME/KEY: exon
(B) LOCATION: 1036..1706

(ix) FEATURE:
(A) NAME/KEY: intron
(B) LOCATION: 754..819
(D) OTHER INFORMATION: /note="There is 8kb of undefined sequence between 787 and 788 of intron 1."

(ix) FEATURE:
(A) NAME/KEY: intron
(B) LOCATION: 968..1035
(D) OTHER INFORMATION: /note="There is 6 kb of undefined sequence between 998 and 999 of intron 2."

(xi) SEQUENCE DESCRIPTION: SEQ ID NO:11:

| | | | | | |
|---|---|---|---|---|---|
| GCCACTGCTC | TCCAGCCTGG | GTGACAGAGT | GAGACTCCAT | CTCAAAAAAA | AAAAAAAAA | 60 |
| AAAAAAAAG | AAGAAAAAGA | AGAAGAAGAA | GAAACTGTTC | ATCTGAAATC | CGACAACTCA | 120 |
| TTCTTGAAGG | TTAGAGCTCA | GCTTTGAAGT | TTCACTTCAC | GAGCTTGGCT | CAGTGAGGTA | 180 |

```
TGTTACTCCC CGGTGAAAAA GAAAATGAAG AGAATGTTTT ATGTTGAAAG TGCTTGGTGA        240

CGAAAAGGCA GCACCTAGAT CCCTTATCTC ATAAAAATG CAGCAGATTC TTAATATTAG         300

CAATCTAGTA TTTAGATTGT TACCTGAAGA AAGGAAAAAC AAACTGTCCC AAATGCTGAT        360

TCTACTGTTT CGGTGGGAAA AAAAAATGTC TTGCAGGCAA GTGGCAAACA ACAAAACTTT       420

TGAAAAAGCA GGCCTGGGGG GAGTCCAGTA CAGTTTCATA ATGGGTATGA ATAGTTATTT       480

TACTGTGTTC CCCCCACCCC CTTTCTTTCT GGGTTTTGAT GTGGATGTCT TTCTATTTGT       540

TCAGGAAATT GTGACGTGTG TTCTGGGCAG GGTTTGAGGT TTTGGAACAT TTTCTAAAAG      600

GGACAGAGAG CACCCTGCTA CATTTCCTAA TCAAGAAGTT GGCGTGCAGC TGGGAGAGCT      660

AGACTAAGTT GGTC ATG ATG CAG AAG CTA CTC AAA TGC AGT CGG CTT GTC         710
             Met Met Gln Lys Leu Leu Lys Cys Ser Arg Leu Val
              1               5              10

CTG GCT CTT GCC CTC ATC CTG GTT CTG GAA TCC TCA GTT CAA  G              753
Leu Ala Leu Ala Leu Ile Leu Val Leu Glu Ser Ser Val Gln
       15              20              25

GTAAGACTCA GGAGTCTTGT TCCCCAGCCA TCTTCTACTT AGTAACAATG TGGGTTCCTC       813

GGGCAG GT TAT CCT ACG CAG AGA GCC AGG TAC CAA TGG GTG CGC TGC           860
       Gly Tyr Pro Thr Gln Arg Ala Arg Tyr Gln Trp Val Arg Cys
              30              35                      40

AAT CCA GAC AGT AAT TCT GCA AAC TGC CTT GAA GAA AAA GGA CCA ATG         908
Asn Pro Asp Ser Asn Ser Ala Asn Cys Leu Glu Glu Lys Gly Pro Met
           45              50                      55

TTC GAA CTA CTT CCA GGT GAA TCC AAC AAG ATC CCC CGT CTG AGG ACT         956
Phe Glu Leu Leu Pro Gly Glu Ser Asn Lys Ile Pro Arg Leu Arg Thr
       60              65                      70

GAC CTT TTT  CC GTAAGTGGAC TTTTCTCTAA TTAATTAATT TCCACTGGTT             1007
Asp Leu Phe Pro
       75

TTTTTCCCAT TTTTCTTTCA TACTTCAG A AAG ACG AGA ATC CAG GAC TTG AAT        1060
                                Lys Thr Arg Ile Gln Asp Leu Asn
                                              80

CGT ATC TTC CCA CTT TCT GAG GAC TAC TCT GGA TCA GGC TTC GGC TCC         1108
Arg Ile Phe Pro Leu Ser Glu Asp Tyr Ser Gly Ser Gly Phe Gly Ser
85              90              95                     100

GGC TCC GGC TCT GGA TCA GGA TCT GGG AGT GGC TTC CTA ACG GAA ATG         1156
Gly Ser Gly Ser Gly Ser Gly Ser Gly Ser Gly Phe Leu Thr Glu Met
             105             110                     115

GAA CAG GAT TAC CAA CTA GTA GAC GAA AGT GAT GCT TTC CAT GAC AAC         1204
Glu Gln Asp Tyr Gln Leu Val Asp Glu Ser Asp Ala Phe His Asp Asn
        120              125                     130

CTT AGG TCT CTT GAC AGG AAT CTG CCC TCA GAC AGC CAG GAC TTG GGT         1252
Leu Arg Ser Leu Asp Arg Asn Leu Pro Ser Asp Ser Gln Asp Leu Gly
       135              140                     145

CAA CAT GGA TTA GAA GAG GAT TTT ATG TTA TAAAAGAGGA TTTTCCCACC          1302
Gln His Gly Leu Glu Glu Asp Phe Met Leu
       150              155

TTGACACCAG GCAATGTAGT TAGCATATTT TATGTACCAT GGTTATATGA TTAATCTTGG      1362

GACAAAGAAT TTATAGAAA TTTTTAAACA TCTGAAAAAG AAGCTTAAGT TTTATCATCC       1422

TTTTTTTTCT CATGAATTCT TAAAGGATTA TGCTTTAATG CTGTTATCTA TCTTATTGTT      1482

CTTGAAAATA CCTGCATTTT TTGGTATCAT GTTCAACCAA CATCATTATG AAATTAATTA     1542

GATTCCCATG GCCATAAAAT GGCTTTAAAG AATATATATA TATTTTAAA GTAGCTTGAG      1602

AAGCAAATTG GCAGGTAATA TTTCATACCT AAATTAAGAC TCTGACTTGG ATTGTGAATT     1662
```

ATAATGATAT GCCCCTTTTC TTATAAAAAC AAAAAAAAAA TAAT   1706

(2) INFORMATION FOR SEQ ID NO:12:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:12:

```
Met Met Gln Lys Leu Leu Lys Cys Ser Arg Leu Val Leu Ala Leu Ala
 1           5                  10                  15
Leu Ile Leu Val Leu Glu Ser Ser Val Gln Gly Tyr Pro Thr Gln Arg
             20                  25                  30
Ala Arg Tyr Gln Trp Val Arg Cys Asn Pro Asp Ser Asn Ser Ala Asn
         35                  40                  45
Cys Leu Glu Glu Lys Gly Pro Met Phe Glu Leu Leu Pro Gly Glu Ser
     50                  55                  60
Asn Lys Ile Pro Arg Leu Arg Thr Asp Leu Phe Pro Lys Thr Arg Ile
 65                  70                  75                  80
Gln Asp Leu Asn Arg Ile Phe Pro Leu Ser Glu Asp Tyr Ser Gly Ser
                 85                  90                  95
Gly Phe Gly Ser Gly Ser Gly Ser Gly Ser Gly Ser Gly Ser Gly Phe
                100                 105                 110
Leu Thr Glu Met Glu Gln Asp Tyr Gln Leu Val Asp Glu Ser Asp Ala
            115                 120                 125
Phe His Asp Asn Leu Arg Ser Leu Asp Arg Asn Leu Pro Ser Asp Ser
        130                 135                 140
Gln Asp Leu Gly Gln His Gly Leu Glu Glu Asp Phe Met Leu
145                 150                 155
```

(2) INFORMATION FOR SEQ ID NO:13:

(i) SEQUENCE CHARACTERISTICS:
        (A) LENGTH: 1507 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: CDS
        (B) LOCATION: join(546..618, 662..806, 846..1083)

(ix) FEATURE:
        (A) NAME/KEY: exon
        (B) LOCATION: 505..618

(ix) FEATURE:
        (A) NAME/KEY: intron
        (B) LOCATION: 619..661
        (D) OTHER INFORMATION: /note="There is 8kb of undefined
            sequence between position 643 and 644 of intron
            1."

(ix) FEATURE:
        (A) NAME/KEY: exon
        (B) LOCATION: 662..806

(ix) FEATURE:
        (A) NAME/KEY: intron
        (B) LOCATION: 807..845
        (D) OTHER INFORMATION: /note="There is 4kb of undefined
            sequence between position 826 and 827 of intron
            2."

(ix) FEATURE:

(A) NAME/KEY: exon
(B) LOCATION: 846..1507

(xi) SEQUENCE DESCRIPTION: SEQ ID NO:13:

```
AATTCTAGCA GACTCTGGAC GTTAACGGAG ACCGCTCATC CTGGGGGCTG AGAACCCAGC      60

TCGGCTCGGA ATGTTCCCTG CTTGTGCCTG ACTCTGTGCG CGCCCAGCTT CTCTTTGATG     120

TGCGCTGTGG ATGAGCCGAG CTCAGTTCTG GAACAGCTGA GTCCTCCTGT CTGTTTAGAT     180

TGTTACCTGA AGGAAGGGAG GGGGAAGAAA GTGCTGATTC GACTTTTTGA TGGGGAAAAC     240

TTTTTTTTTA AACATGCAAA TGACAGATGG CAGAGCTTTT TGGAAAAAGA AAAAATAATA     300

ACCACACAGC AAACGCCTAG GGGGAGTCCG GTGGAGTTTC ATCATGGGTA TGAACAGTTG     360

TTGTTTTTTT CAACTTTCTT CTTCTTTCTG GGTGTTGATG TGGATCTCTT TCTATTTGTT     420

CAGGAAACTG TGACGTGTGT TCTTGGGCAG GGTCTGAGGT TTTGGAACCT CTTTCTAAAA     480

GGGACAGAAA GAGCACCCTG CTACATTTGC TAATCCAGAG GCTGAGTGGA GCCGAGCTGG     540
```

```
TCAGG ATG CAG GTT CCC GTC GGC AGC AGG CTT GTC CTG GCT CTC GCC          587
      Met Gln Val Pro Val Gly Ser Arg Leu Val Leu Ala Leu Ala
      1               5                   10

TTC GTC CTG GTT TGG GGA TCT TCA GTG CAA  G GTAAGAGACC CAGGATCTTT        638
Phe Val Leu Val Trp Gly Ser Ser Val Gln
15  ,                      20

AATTCGGTTC CTTGTTCGCA CAG  GT TAT CCT GCT CGG AGA GCC AGG TAC           687
                             Gly Tyr Pro Ala Arg Arg Ala Arg Tyr
                             25                  30

CAG TGG GTC CGC TGC AAA CCG AAT GGC TTT TTT GCG AAC TGC ATC GAG        735
Gln Trp Val Arg Cys Lys Pro Asn Gly Phe Phe Ala Asn Cys Ile Glu
    35                  40                  45

GAG AAG GGA CCA CAG TTT GAC CTA ATA GAT GAA TCC AAT AAC ATC GGC        783
Glu Lys Gly Pro Gln Phe Asp Leu Ile Asp Glu Ser Asn Asn Ile Gly
50                  55                  60                  65

CCT CCC ATG AAT AAT CCT GTT  TT GTAAGTAGAC TTTCATCGAT TTTTTCTTT        836
Pro Pro Met Asn Asn Pro Val  Leu
                70

GTATTTTAG G ATG GAA GGA CCC TCA AAA GAT TTC ATC TCC AAT TAT GAT        885
            Met Glu Gly Pro Ser Lys Asp Phe Ile Ser Asn Tyr Asp
            75                  80                      85

GAC TAT GGG TCA GGT TCG GGC TCC GGC TCT GGC TCC GGC TCT GGC TCG        933
Asp Tyr Gly Ser Gly Ser Gly Ser Gly Ser Gly Ser Gly Ser Gly Ser
            90                      95                  100

GGT TCC GGC TCC GGA AGT GGC TTC CTA GGT GAC ATG GAA TGG GAA TAC        981
Gly Ser Gly Ser Gly Ser Gly Phe Leu Gly Asp Met Glu Trp Glu Tyr
        105                     110                 115

CAG CCA ACA GAT GAA AGC AAT ATT GTC TAT TTC AAC TAT AAG CCT TTT       1029
Gln Pro Thr Asp Glu Ser Asn Ile Val Tyr Phe Asn Tyr Lys Pro Phe
120                 125                     130

GAC AGG ATT CTC ACT GAG CAA AAC CAA GAC CAA CCA GAA GAC GAT TTT       1077
Asp Arg Ile Leu Thr Glu Gln Asn Gln Asp Gln Pro Glu Asp Asp Phe
135                 140                     145                 150

ATT ATA TGAATGTGAC GGTCTCTGTC TCCCCACCTC CATGTGGAAC AATGTATTCA        1133
Ile Ile
```

```
GTATACTTAG TGTACCACGT TTAAATGACC AGTCTCAGGA TAAAGAGTTT TACAGAAAAT     1193

TTAAAATGCC TGGAAAAGAC TCTTGAATCC TGTTACCCCT TTCCTCATTA ACTCGTAAGG     1253

AATTATGCTT TAATGCTGTT ACCTATCTTG TTGTTCTGGA AAATGCCTGC ATTTATGTGT     1313

ATTGAATCAA CATTTAAGAA ATTAACACAC ACCCCCATTA TTATACAATA ACTTTCAAAG     1373

CCATACTGGT TTTGAAAATT TTAATTTGAT AGCAAGTTGA TGAACAATCT TTCATACCTA     1433
```

```
AAGTGTTCAG GAACCCAACT CGCATTGTGA ATTACAAATA TATTCCTTTA TGTGATTAAA      1493

AAGAAAATAA AGTG                                                       1507
```

(2) INFORMATION FOR SEQ ID NO:14:

(i) SEQUENCE CHARACTERISTICS:
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO:14:

```
Met Gln Val Pro Val Gly Ser Arg Leu Val Leu Ala Leu Ala Phe Val
 1               5                  10                      15

Leu Val Trp Gly Ser Ser Val Gln Gly Tyr Pro Ala Arg Arg Ala Arg
            20                  25                  30

Tyr Gln Trp Val Arg Cys Lys Pro Asn Gly Phe Phe Ala Asn Cys Ile
        35                  40                  45

Glu Glu Lys Gly Pro Gln Phe Asp Leu Ile Asp Glu Ser Asn Asn Ile
    50                  55                  60

Gly Pro Pro Met Asn Asn Pro Val Leu Met Glu Gly Pro Ser Lys Asp
65                  70                  75                  80

Phe Ile Ser Asn Tyr Asp Asp Tyr Gly Ser Gly Ser Gly Ser Gly Ser
                85                  90                  95

Gly Ser Gly Ser Gly Ser Gly Ser Gly Ser Gly Ser Gly Phe Leu Gly
            100                 105                 110

Asp Met Glu Trp Glu Tyr Gln Pro Thr Asp Glu Ser Asn Ile Val Tyr
            115                 120                 125

Phe Asn Tyr Lys Pro Phe Asp Arg Ile Leu Thr Glu Gln Asn Gln Asp
        130                 135                 140

Gln Pro Glu Asp Asp Phe Ile Ile
145                 150
```

(2) INFORMATION FOR SEQ ID NO:15:

(i) SEQUENCE CHARACTERISTICS:
        (A) LENGTH: 17327 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: exon
        (B) LOCATION: 621..753

(ix) FEATURE:
        (A) NAME/KEY: intron
        (B) LOCATION: 754..9596

(ix) FEATURE:
        (A) NAME/KEY: exon
        (B) LOCATION: 9597..9744

(ix) FEATURE:
        (A) NAME/KEY: intron
        (B) LOCATION: 9745..16396

(ix) FEATURE:
        (A) NAME/KEY: exon
        (B) LOCATION: 16397..17327

(xi) SEQUENCE DESCRIPTION: SEQ ID NO:15:

```
GCCACTGCTC TCCAGCCTGG GTGACAGAGT GAGACTCCAT CTCAAAAAAA AAAAAAAAA        60

AAAAAAAAG AAGAAAAAGA AGAAGAAGAA GAAACTGTTC ATCTGAAATC CGACAACTCA      120
```

| | | | | | | |
|---|---|---|---|---|---|---|
| TTCTTGAAGG | TTAGAGCTCA | GCTTTGAAGT | TTCACTTCAC | GAGCTTGGCT | CAGTGAGGTA | 180 |
| TGTTACTCCC | CGGTGAAAAA | GAAATGAAG | AGAATGTTTT | ATGTTGAAAG | TGCTTGGTGA | 240 |
| CGAAAAGGCA | GCACCTAGAT | CCCTTATCTC | ATAAAAATG | CAGCAGATTC | TTAATATTAG | 300 |
| CAATCTAGTA | TTTAGATTGT | TACCTGAAGA | AAGGAAAAC | AAACTGTCCC | AAATGCTGAT | 360 |
| TCTACTGTTT | CGGTGGGAAA | AAAAAATGTC | TTGCAGGCAA | GTGGCAAACA | ACAAAACTTT | 420 |
| TGAAAAGCA | GGCCTGGGGG | GAGTCCAGTA | CAGTTTCATA | ATGGGTATGA | ATAGTTATTT | 480 |
| TACTGTGTTC | CCCCCACCCC | CTTTCTTTCT | GGGTTTTGAT | GTGGATGTCT | TTCTATTTGT | 540 |
| TCAGGAAATT | GTGACGTGTG | TTCTGGGCAG | GGTTTGAGGT | TTTGGAACAT | TTTCTAAAAG | 600 |
| GGACAGAGAG | CACCCTGCTA | CATTTCCTAA | TCAAGAAGTT | GGCGTGCAGC | TGGGAGAGCT | 660 |
| AGACTAAGTT | GGTCATGATG | CAGAAGCTAC | TCAAATGCAG | TCGGCTTGTC | CTGGCTCTTG | 720 |
| CCCTCATCCT | GGTTCTGGAA | TCCTCAGTTC | AAGGTAAGAC | TCAGGAGTCT | TGTTCCCCAG | 780 |
| CCATCTTCTC | TGTAAGCCCT | GTGGTCCATG | CAAGTCATTA | TATTCATTTT | AAGGCATAGA | 840 |
| ATGTATAATA | TTGTGAGAAA | GGAGGCAAAG | AAGAAGGATT | TGGGGTCGCT | GAACCCTTTA | 900 |
| ATATGAGTTC | TGTTAAGTTT | GGTACCAAGA | AAAATTAAAC | TCTGTGGCGT | GTGCAGTCTT | 960 |
| GTAAACTCTT | ACAATGATTG | AAATGTGCTA | TTTTGGGATG | AAAATGTGAG | GTTTATAAAT | 1020 |
| TTTAAAAGCT | CAAAAAGGA | ATCTAGAAAA | TGACTCCTGT | GCCTGTTGCA | TGGAGGAGAT | 1080 |
| GGCACCTTTG | ACTGTTGGGG | GGTGTCTGCC | TACCCCTAAG | TGTCTACATC | AGCCCCAAGT | 1140 |
| TTTAGTGCGC | TGTGACGGTG | TCATTGTTAT | TTTAACACTG | GGAGACGTTA | TATTCCAATT | 1200 |
| GGGGTGAATC | TGACTGTGTG | TATTTTCTTT | TCTTTTTTTT | TTTTTAAAG | ATAAACTTGG | 1260 |
| TTCTTACTGA | AAACTCAATT | ATGGTTAGAC | ATAGTTCATG | TAAAACCTCT | CAGATTTTAA | 1320 |
| AGAGAAGGCC | AAATAATTTG | GTATTTGTGC | TCTTGCTCAG | AGAAGCATCA | TATTCGGAAA | 1380 |
| TATCTTCCTA | GGTTTATCTA | CCATTTAGTG | TTGTTTAGTC | AGACTGAAAC | AACTTAAAAC | 1440 |
| CTGTAATGAC | TAAGACAATG | AAAATGATAG | GCTTGTAAGA | AAAATACAAT | TTGTTATTCT | 1500 |
| TTGGCAAATA | AGGAATCATG | TCTAAATAAG | ACGGAGGTCA | TGGCTTGATA | GAGAGATGGC | 1560 |
| TGAACCTATA | GTAGAAAAAC | ACTAGGTTCC | GCCAAATGGT | AAGGGAAATG | TTGAGTCACA | 1620 |
| ATGACACACA | TGTCCTAGAT | TTGTTTCGTC | AAAGCGACTT | TTGGTTGTCA | TGATCTTACT | 1680 |
| TCCGGTGGAG | ATGAAATCTT | ACAGATGATC | GCAGAGACAT | TCATTTTATG | TTGGAAATTT | 1740 |
| ATAAAATCAT | TTTCTTCTAG | TTATGCTAAT | GCTGAAAAAA | GAGCAAGTAA | TGTTTCTGGA | 1800 |
| ACGTTATTAA | TTTATGTATT | TTTAAAATAT | AAAACATTGT | CAATTGTAGG | GAACAGGCTT | 1860 |
| CACTGGGATC | TTTTAGGGAA | TATCTTCAGC | TTGATGAAAT | AATTCCCGAA | TAGCCAAGTG | 1920 |
| GTCTGACAAG | ATCGAGAGTA | ATGAGGCCCA | TACTTTAGTA | CAGTCTTGAA | TGGCCAGATG | 1980 |
| GTGCTGGGCA | TACCCCAACC | AGAGATATGT | AAGTCTTTAT | GTTGTCAAAA | TTTCCCAGAA | 2040 |
| ACATGAATTT | CCCACTAAGA | TTCATTAAGG | AAAACTAGAA | TGAAAACAAA | AACGTTCCTT | 2100 |
| GTATAATATT | CATTAGAAAG | AAATGAAGAA | GGCCGGGCAT | GGTGGCTCAC | GCCTGTAATC | 2160 |
| CCAGCACTTT | GAGAGGCCAA | GGTAGGCAGA | TCATGAGGTC | AGGAGTTTGA | GACCAGCCTG | 2220 |
| GCCAACATAG | TGAAATCCCG | TCTCTACCAA | AAATACAAAA | AAATTAGCCG | GGCATGGTGG | 2280 |
| CACACACCTG | TCATCCCAGC | TACTCAGGAG | GCTGAGGCAG | GAGAATTGCT | TGAACCTGGG | 2340 |
| AGGTGGAGGT | TGCAGTGAGC | TGAGATTGCA | CCACTGTACT | ACAGCCTAGG | TGACAGTGCA | 2400 |
| AGACTCTGTC | AGAAAGAAAG | AAAGAGAGAG | AGAGAGAAAG | AAAGGAAAGA | AAGAAAGAGA | 2460 |
| AGGAAAGAAA | ATAATTCATC | ATGAAATTGT | ATAGAATACT | AGCATTTATG | TCATGACCTC | 2520 |
| GTAGGTTTAG | CTCTTTGTTA | GAAAAGGAAA | CCATAGAAAG | AGACAAGGGA | GAAACTGACA | 2580 |

-continued

| | | | | | |
|---|---|---|---|---|---|
| AACTAGGGTG | TTTCCGAAAA | AAGGCTCTCA | GTATCGGGCT | CAAGGGCTTG | TGCCCACATC | 2640 |
| TGAGCATGCA | GGGAAATAGA | TGTCCCCCAC | TGGCTGCACA | TGTGAGTGAC | TGCGGCACAA | 2700 |
| GGCTGTGATG | TGAAGAGTCA | TGACACCATT | TCCTCACACC | TCCACGCAAT | GCCAGATATG | 2760 |
| ATTCGACAAC | ATTCTTCCTG | TCTTATAAAA | GTGTTTATCT | AGCCCGTTGG | TTTGGCAGAT | 2820 |
| GAAATCAACT | AGGCTTTTGG | CTTGCTTTTA | CTGAGCATAT | TCAAACCAT | TTCAGGTCAC | 2880 |
| TATAGTGGTT | TGCTCGGGTT | GCCATAACAA | AGTACCACGG | ACTGAGTGGC | TTAAATAACA | 2940 |
| GAAATGTATT | TCCTGACAGT | TCTGGAGATG | GGAGTCCAAG | ATCAAGGTGC | TGGCAGGGTC | 3000 |
| GATCGCATTC | TGAGGCCTCT | CTCCTTGGCT | TATAGATGGC | GCCTTCTCCC | TTGTCTGCAC | 3060 |
| ATGGCCTTTC | CTCCATGCAT | CCGTGTCTTA | ATACCATCTT | CTTAGAGGGT | CACCAGGCAT | 3120 |
| TGGATCAGGG | CCACCCTAAT | GGCCTCATCT | TAACTACCTA | TATCTGCAAT | GACCCTATTT | 3180 |
| CTGAACAATT | TCACATTGTG | AGATTCTGTG | GGTTAGAACT | GGAACATATG | AATTTGGTGG | 3240 |
| TGGTATATTT | TTATTATAAG | TCAAACCCAA | GTAAAGATGT | GGGGTAAGAT | TGTGTTTACC | 3300 |
| AAGCACAAAG | AAATGGAAAT | TGGGGATGT | GTAACTCTGG | AGAGCACAGA | TGACTAATCT | 3360 |
| ATTTAATGTA | GGGCTCCAGG | GGATTTGATG | AGGCCTGTGA | ATCTTCCACT | TTTATTGCCT | 3420 |
| CTCTTTTCCA | ATGACACCCA | TAAAGAAAAA | AAATGGAATA | TCCATGAACA | GGTGCAGCCA | 3480 |
| AGGAGGCCAG | GCCCGCCATG | TGTCCACTGT | ATACTGTCTC | CTAGCTCACA | GGAATGATAC | 3540 |
| TGATCCACTC | CTTGTGCTGC | TCTTTGTAAA | GTGATTTCAC | ATCCATTCTC | TGGTAATCAT | 3600 |
| CATCACATTC | CCTGTGATGA | GGAATTAGCA | CCAATTATAG | AGGAGAAAAC | TGGATCTGAC | 3660 |
| ATTTCTCATC | TCATTTGCTC | TATACATTAA | CCTCTTGCAA | AAAATTTGTG | AGTCTTGCCC | 3720 |
| AAGACCCATT | ACAACTAATT | AACGGCTGAA | CTGGTCGTCT | GATTTCAAGG | CCAGAATTAA | 3780 |
| CTTTCTACTG | CAGCTCATGG | ATCAGAGGTT | TTCTTTATTT | AAACAAACAA | ACAAAAAATC | 3840 |
| CTTTGACCGT | AGCCCTTGCT | ATAACATTTC | CCACTGAGTT | GAGGGAGAAA | TTGAAAGTAA | 3900 |
| ACTTAGGAGC | TTTTTATAGC | TTGTCAAACC | ATGCAAGAGT | GGGGGAAGCT | TATCCATCTT | 3960 |
| GTGGAATTGA | TAGACCAGGA | GGAAGTAACT | CCGGCTTAGA | TAATGCTACC | ATTTTGAATA | 4020 |
| AATCAAATGG | TCTTCTTTTC | CCCTTCATGG | TAGTTGCTGC | TTAAGTTTCT | CTAACATGCC | 4080 |
| TGCAGTAAGT | TTCCATTAAG | AATAGGAAAT | TAGGCTCGGT | ACAGTGGCTC | ACGTCTGTAG | 4140 |
| TCTTAGCACT | TTGGGAGACC | GAGGAGTGTG | GATCACTTGA | GGTCAGGAGT | TCAAGACCAG | 4200 |
| CCTGGCCAAC | ATGGTGAAAC | CCCCATCTCT | ACTAAAAATA | CAAAAATTAG | CCAGGCATAG | 4260 |
| TGGCATGCAC | CTGTAATCCC | AGCTACTCGA | GAGGCTGAGG | CAGGAGAATC | ACTTGAACCA | 4320 |
| GGGAGATGGA | GGTTGCAGTG | AGCCAAGATC | ATGCCACTGC | ACTCCAGCCT | GGGCGATAGA | 4380 |
| CTGAGACTCT | GTCTCAAAAA | AAAAAAAAA | AAAAGAAAA | AGAAAAGAA | AAAAAAAGA | 4440 |
| AATTAGTATA | TTGTGATTAT | GTTGAGGGAA | AAGTTAGTAC | CATAATATAA | AAAGGTATGG | 4500 |
| ACTATTGGAG | AAAGTTGTTT | GCTTTGGTAA | CATTTACTCA | TAGAAAGTAT | TTTGGTAAAG | 4560 |
| CAGGACTCAG | GGTGGTGGGG | GAGGTGGGCA | GTGAGGGATA | GGATTCAAAT | AAAACCATT | 4620 |
| CTTTCCCTTG | GAATCCACTA | CACAATTAAC | CAACAAATCC | CATAAGTGGA | CCTTTTAGGA | 4680 |
| AGATAACATT | TCTATCCATG | AGCATAGCCA | CTATAATCAC | AAGACATTTA | TCTCAAGCAA | 4740 |
| GATAGAGTCA | AGATACTCTC | ACAACCTCAG | GGGCTGGAAC | TGTAAATTTT | CACATCCTGC | 4800 |
| CAACACCCTT | GAATAGCTAT | GTCAAGAATT | TAGTGTCTGT | AACTTGTTCT | TTATTTAAA | 4860 |
| GTACATTTAA | CATCATCGGC | CCCAAATTAG | ATAGGCTTTT | GGAGTGGGAT | CCCTTCTACT | 4920 |
| TTTGATTTCT | TTATAAAATT | TTAAAATAGC | TTTGTTGAGA | TAGTGTTCAC | ATACCATACA | 4980 |
| GTTCACCCAT | TAAAAGTGTT | CAATTCAGTG | ATTAGGCCAG | GTGTGGTGGC | TCATGCCTGT | 5040 |

```
AATCCCAGCA TTTTGGGAGG CCAAGGCAAG TGGATCACTT GAGGTCAAGA GTTTGAGACT    5100
AGCCTGGCCA ACATGGTGAG AACTTGTCTC TACTAAAAAT ACAAAATTA ACTGGGCATG     5160
GTGGTGTGCA CCTGTAATTC CAGCTACTTG GGAGGCTGAG GCAGGAGAAT CACTTGAACC    5220
TGGGAGGTGG AGGTTGCAGT GAGCTGAGAT TGCACCACTG CACTCCAGCC TGGATGACGG    5280
AGCAAGACTC TGTCTCCAAA AAAAAAAAA AAAAAGTGT TCAATGTTTT TTAGTATATT      5340
CACAGAGTCA TGCAACCATC ACTATAATTG CTTCTAGAAC ATTTTCATCA TCCCCCAAAA    5400
GAAAGCCTTC GTTACGAATT TTAATTAGCT GAGATTCTGA ACTCTGGGGG AATTTTGTAT    5460
TCTAGAAATA TTTTTTACTA ATATGCTACA GTTGTATTTG TCATGCTGGT GAAAAGATGT    5520
GGTCTTTCAC CTGGATGCTT TCTCATTAAG CATTATTTTT CTGTTTAGCT TCCTGTGTGA    5580
GCAAACATTT TCTCAGCTTG ATACTCAGTG CATCAGCGGC TTGCAGAAGA GACTGCCTAG    5640
GCCTGCTCTG TCCAGTACGG TAGCCACAAG TCACTTGTGG CTACTGAACA CTTGAAATGT    5700
GGCCAAGGCA AATTGGGACA GGCTGTGAAT GCAAATATA CAAGATTTGG AACCCTTAGT     5760
ATGAAGAAAA GAATGCAAAA TATCCCAGTA ATAACTTTA CATTGATGAT ATGTTAAAGG     5820
ACAATATTTG AATATGTTAG GTTAAATAAA ATTAATTTCA CCTGTTTCTT TTTACTTTTA    5880
AAAATATGGC CGCTGGAACA TTTAAAACTC CCTATGTGGT TTGCTTTGTG TTTCTATTGG    5940
ACAAAGTTGG TCTAGACAGT ACAAGGTGTG AAGACACCGC CCTCTGCTGG AGAAGATGCT    6000
GGATTTTTAT TTCACCTACA GGAAGAGACG TCTAAGTAGC AATTAGATGC TAAACTAATG    6060
CTGCCTCAGG AAAGAATCAA AAGAGAAAGA GTGAAACCAG GCCGGGCGCG GTGGCTCACG    6120
CCTATAATCT CAGCCACTTT GGGAGGCCAA GGCGAGGGA TCACGAGGTC AGGAGATCGA     6180
GACCTTCCTG GCTAACCCCG TCTCTATTAA AACTACAAAA AATTAGCCGG GCATGGTGGC    6240
ACGTGCCTGT AATTCCAGCT AGTCGGGAGG CTGAGGCAGG AGAATAGCTT AAACCCAGGT    6300
GGCGGAGGGT GCAGTGAGCT GAGATGTGCC ACAGCACTCC AGCCTGGGCA ACAGAGCCAG    6360
ACTCTATCTC AAAATAAGGA AAAATAAAAA AGAAAAGAAA GAAAGTCCAT AAATTGAGAC    6420
TCCTAGAGAT ACTAAATGGT AGAATGGGAA TTTGAATTTA AATTTATAAG ATGTTCACTC    6480
TCGGAGATCA TAGGTCATTG TTGTCCTCCT CCTTTTCATG ACAGGAACTA GCAATGAAGA    6540
GCTCTGACTA TGTGCTAGGT ACTACTCTGA GAACCTAACA TTTGTATCTC CTTATTAACT    6600
CTATTACTGC CCCATCCTAC AGATGAGAAA ATTGAGGCAC AGGAAGTTTA AGTTGGCCAA    6660
GATCACACAG CCAGTAAGGG GCAGACATTG AAAGGTCATT TTGCCTGCCT TATCCCCAGC    6720
CTCCAGGCAG TGGCAGAGTT AGCTCATTTT GGACAAACAG CTCTCCCAGA CCAGACATTG    6780
TAAGCTATAC TCAGGAATCA TAGGAAAGAT TATGATAGAA TAATATATAG TTACAAAGAA    6840
AAGAAAGAAA ATCCAATGGG AGAATATTTA CTGTTTTCTA TATTAAAGTG TTTAATGTTT    6900
ATGTTTTTAG AGGAATATTG TTTATTATAG CAATTTAGAA AACAAAATGA GAAAAAAAAT    6960
CACCAAAGAT TCTACCTCCA GTTATTTTTG TGTATTTCCT TCCATTTTTC CCCCCATGTC    7020
TGTTTATATA ATTGAAACTA TTATTCATGC AAAGAGGTAT TCTGATTTTC TCAGTTATTT    7080
TTATTTATTT TTAATTTTGT AAATAAACTT TTTTCTTCTG AGACAGTCTC GCTGTGTCAC    7140
CCAGGCTGAA GTGCAGCCGT GCAATCTTGG CTCACTGTGA CCTCCAGTC TCAAGCAATC     7200
TTCCTGCCTC AGCCTCCTAA GTAGCTGGGA CTGCAGATGT GTGCTACCAC ATCCAGCTAA    7260
TTTTAAAAT CTTTTTCTC TTTTTGGTA GAATGGGAG TCTCTCTATG TTGCCCAGCC        7320
TGTATTGAAC TCCTGGGCTC AAGTGATCCT CCCACCTCAG TCTCCCAAAG TGCTGGGATT    7380
TCAGGCATGA GCTACCACAC CCAACCTAAT TTTTATTTTT ATTTTATTAA AAAAAAAGT    7440
TTTTGCCTAC CCGCCTCTCA CCCTCTCACT CATTTTTAAG TATAGGTTTT TCTACAATGC    7500
```

| | | | | | |
|---|---|---|---|---|---|
| CACATTGTCT | TTTCCATAAA | AAGTACTTTC | GGCCGGGTGT | GGTGGCTCAC | ACCTGTAATC | 7560 |
| CCAGCACTTT | GGGAGACTGA | GGCGGGTGGA | TCACCTGAGG | TCAGGAGTTC | GAGACCAGCC | 7620 |
| TGGCCAACAT | GGTGAAACCC | CATCCCTACT | AAAAATACAA | AAATTAGCTG | GATATGATTG | 7680 |
| TGGGCACCTG | TCATCCCAGC | TACTCGGGAG | GCTGAGGCAG | GAGAATCGCT | TGAACCTGGG | 7740 |
| AGGCAGAGGT | TGCAGTGAGC | CGAGATTGTG | CCACTGCATC | CAGCCAGGG | CAACAGAGCG | 7800 |
| AGACTTCATC | TCAAAAAAAA | AAAAAAAAG | TACTTTTCTT | CATTTGGTTA | GTATTCTCTT | 7860 |
| ATGAGTTGAT | GCCTTGTAAT | TTATCTGAAT | GTTTTCCATT | ATTTGTGGT | GAGCTTTAAA | 7920 |
| ACTACCCTTC | CTGACTTTCA | AGAATCCTAG | ACATGCTCCT | TCTTGCTAGG | TAATTATTAG | 7980 |
| TTGCACTCAT | TAGAATAAAG | TATATGCTTG | GAGTGGGGAG | GAGATGAACT | TTTTGAAGGG | 8040 |
| CGGTGAAGTA | TTTCTCACCA | CCAGGCCTTT | GTCTTTGCTA | AACTGAGGAA | GGAAGATTTT | 8100 |
| ATTTCATTAG | CTAACAAAGA | ACCTCCTATA | TAGGCCGGGC | ATGGTGGCTC | ACGCCTGTAA | 8160 |
| TCCTCACATT | TTCAGAGGCC | AAGGTGGGTG | GATTGCCTGA | GCTCAGGAGT | TTGAGACCAG | 8220 |
| CTTGGGCAAC | ATGGCAAAAC | CCCATCTCTA | CTAAAAATAC | TAAAAATTAG | CTGGGCGTGG | 8280 |
| TGGTGAGTGC | CTGTAATCCC | AGTTACTCCA | GAGGGTGAGG | CAGAAAATTG | CTTGAACCCG | 8340 |
| GGAGGTGGAG | GTTGCCATGA | GCCGAGATCG | TGACAGTGCA | CTCCAGCCTG | GGCGACACAG | 8400 |
| CAAGACTCTC | TCTCAATAAA | ATAAAATAAA | ATAAAATAAA | ATAAATACAT | AAATAAATCT | 8460 |
| CCTATATAAC | CTCATAATAT | CAGATTTGGA | GCCTTTTCCA | TAGAAATGAA | ATTCAGAAGA | 8520 |
| AGCTGAGACT | CAGATATTCC | AAGCTGCCTG | GTGCTCTGTG | AATAGAGGAG | ACTTGTTCTT | 8580 |
| GTGAAATCTG | AGTGCAAAGA | CACAGGACAA | ATTGTTATCT | ACTTTCATT | CCTAAGGATA | 8640 |
| CTGTATGGCC | CTAAAACACA | AGAACTAGAA | TTCTGTGATA | CCACGGGTAC | TCCACAGTGT | 8700 |
| GTTCCTTCCC | CTTTCTGAAC | CTGATTGTC | TCATCTCTAT | GAAAGATGT | GGGCTTTGGG | 8760 |
| GTCAGATGTG | GGTTGGAATC | CTAGCGCCTG | TGTGGCTGCA | ATTTTCTTTT | GTGTAAAATT | 8820 |
| GAGATAATAG | TACAAAAGTA | ACAACAGTTA | ATATTATCAA | GTGCTTACTG | TGTGCCTGGC | 8880 |
| ACTGTGTTAA | ATTCTCTAAG | TGTATTTTCT | CATTTAATTT | TTGTGATAGG | CTTATGACAC | 8940 |
| TATTAGTATC | TTCATATTAC | AGTGAGGGTT | CAGAGAAGTT | AAGGTTCCAT | AACTAGTCAG | 9000 |
| CAGACCTGGG | ACTTCACTCC | AGGCAGCTGA | TTCCAAAGCC | TATTCTAACT | TTAAACTGCT | 9060 |
| ACTTTTGGA | GTGTTGTAAG | AAGGACAATT | TATATAAAT | GTTGGCACAT | AGTGGGTGCT | 9120 |
| GCTGTTATAT | GAATGGGCAC | AAAATCTGTC | TACATTTTGC | CTTTTACCAA | ATTTAGAATC | 9180 |
| TATTTAGTTA | AAACCTTCTT | AGGGCGGGTG | GAGTGCAGTT | GCTCATTCCT | GTAATCTCAG | 9240 |
| CACACTGGGA | GGCCAAGGCA | GGAGGATTGC | TTGAGCCCAG | GTGTTTGAGA | CCAGCCTGGG | 9300 |
| CACATAGTGA | GACCCCATC | TCTCCAAAAA | ACAAACAAAC | AAACAAAAAC | AAACAAAAC | 9360 |
| TAGCTGGGCG | TTGTGGTGCC | CCTGTATTCC | CAGCTACTCA | AGAGGCTGGG | GTGGGAGAAT | 9420 |
| GGCTTGAGCC | CAGGAGTTCA | AGGTTGCAGT | GAGCTATGAT | CACAGTACTG | CACTCCAGCT | 9480 |
| TGGGCAGCCG | ACTGAGACCC | TGTCTCGAAA | AAAAATAAA | AATAAAAACT | TCTTAGGACA | 9540 |
| GAGTGATTAG | AAGCTCTCTA | GTAGATACTT | AGTAACAATG | TGGGTTCCTC | GGGCAGGTTA | 9600 |
| TCCTACGCAG | AGAGCCAGGT | ACCAATGGGT | GCGCTGCAAT | CCAGACAGTA | ATTCTGCAAA | 9660 |
| CTGCCTTGAA | GAAAAAGGAC | CAATGTTCGA | ACTACTTCCA | GGTGAATCCA | ACAAGATCCC | 9720 |
| CCGTCTGAGG | ACTGACCTTT | TTCCGTAAGT | GGACTTTTCT | CTAATTAATT | AATTAATTAC | 9780 |
| TTATTTATTT | GAGACGGAGT | TTCACTTTTC | TTGCCCAGGC | TGGAGTGCAA | TGGCGCAATC | 9840 |
| TTAGCTCACT | GCAACCTCCG | CCTCCTGGGT | TCAAGCGATT | CTCCTGCTTC | AGCCTCTGGA | 9900 |
| GCAGCTGGGA | TTTCAGGCGC | CTGCCACCAT | GCCCAGCTAA | TTTTTTTTTT | TTTTTTTTT | 9960 |

| | | | | | |
|---|---|---|---|---|---|
| TGAGACGGAG | TCTCACTCTG | TTGCTCAGGC | TGGAGTGCAG | TGGCGCAATC | TCGGCTCACT | 10020 |
| GCAAGCTCCA | CCTCCTGGAT | TCACGCCATT | CTCCGCCTC | AGCCTCCGA | GTAGCTGGGA | 10080 |
| CTACAGGCAC | CCGCCACCAC | GCCCGGCTAA | TTTTTTTGTA | TTTTTAGTAG | AGACGGGGTT | 10140 |
| TCACCTTATT | AGCCAGGATG | GTCTCGATCT | CCTGACCTAG | TGATCCGCCC | GCCTTGACCT | 10200 |
| CCCAAAATGC | TGGGATTACA | GGCGTGAGCC | ACTGCGCCTG | GCCTAATTTT | TTGTATTATT | 10260 |
| AGTAGAGACG | GGCTTTCATC | ATCTTGGCCA | GGCTGGTCTC | AAACTCCTGA | CCTCAGGTGA | 10320 |
| TCCACCCACC | TTGGCCTCCC | AAAGTGTTGG | GATTACAAGC | ATGAGCCACT | GTACCCGGCC | 10380 |
| TTTTCTCTAA | TTTTAAAGTG | TCTGTAATTT | CACAACCTCT | TGGCACAGAT | GTGGGAGTGT | 10440 |
| TTTTCTTCAA | GCTGTCCAGA | GTGTTTTGCT | TCGAGCTCTT | GCTTGGTAG | TTTGGCTCTT | 10500 |
| ACTCTGCAGT | ACATGGTAAA | AGTGTACTGT | ATATACTGGC | ATATGACATG | TGCGAGTATA | 10560 |
| CATGATTCAC | CTATGTTTTT | GAAATTTTTT | TTGTGGATGG | TAGAGAGGAG | CATTGAGGAC | 10620 |
| TTTTCATCAA | CAGGTATTGA | AAATGATTGA | ACATTGTTTT | ATTTGTGTAA | ACAGAACACA | 10680 |
| CTATATATAA | AAATCCAATA | ATTAACTGAA | TGGATAAGCA | AATGTGGTA | TAAGCATACA | 10740 |
| AAGGAATATT | ATTGGGTCAT | AAAAAGAATG | AAGTACTGAT | ACATGCTACA | ACATAGATAA | 10800 |
| ACCTTGGAAA | CATTATGCAG | AGCGAAGGAA | GGCCAGACAC | CAAAAGCCAC | ATATTGTATG | 10860 |
| ATTCCATTTA | GATGAAATGT | CCAGAATAGG | CAAATCCCTA | GAGGCAGAAA | GTAGATTAGT | 10920 |
| GGGTTACAGG | GGCTGGGGAA | AGGGAGGAAT | AAGGAGTGAC | TGCTAATGGG | TATGAGGGTT | 10980 |
| TTTTTTGGAG | GAGGTGATTA | AAATGTTCTT | CTGCCAGGTG | TGGTGGCTCA | TGCCTGTAAT | 11040 |
| CCCAGCACTT | TGGGAGGCCG | AGGCGGGAGG | ATTGTTTGAG | CCCAGGAGTT | TGAGGCCAGC | 11100 |
| CTGGGCAACA | TAGTGAGACC | CTATCTCTAT | TTCAAATACA | TTTTTTATAT | TAAAAAAATG | 11160 |
| TTCTTCAAGT | AGTTGGTAAT | TATTTTAAA | AATGGCCAGG | TGCAGAGGCT | CATGCCTGTA | 11220 |
| ATCCCAGCAC | CTTGGGAGGC | TGAGGTGGGA | GGATCCCTTG | AGCCCAGGAG | GTTTGGGACC | 11280 |
| AGCCTGGGCC | ATACAGCAAG | ACCCTGTCTC | TACAAAAAAT | ACAAAAATTA | GCTAGGCATA | 11340 |
| GTGATGTGCA | CCTGTGGTCC | CAGCTACTCG | GGAGGCTGAG | GTAGGAGAAT | CTCTTGAGCC | 11400 |
| TATGTTGAGC | CTGCAGTGAA | CCCTATTTAT | GCCATTGCAC | TCCAGCCTAG | GCAACAGAGT | 11460 |
| AAGACTCTGT | CTCAAAAAAA | GAAAAAAAAA | ATTAGGGAAA | GGAAGAATAA | TTAGCCAAGA | 11520 |
| CTTGTAAAAC | AAAAATCAAA | TCTCTTCTTT | TGATCACATA | AAACTTGCTT | TAAACTTGCA | 11580 |
| AAAAGACCT | GATATAAATT | CATAAGTAAC | AAAAAATTGA | ATTATATTAG | AAACCATTAA | 11640 |
| TTCAATGAAT | ACTAAAGCTA | TGTAGGATGT | AGCAAAATAT | ACATATTAAG | AAAAGGATTA | 11700 |
| TCATAAAAGT | TTTAATCTCC | AGGCTCAAAC | CTAGAAAATC | ACTCTCCTCA | AAGCCAGGGT | 11760 |
| TAATCATCAT | GCTCCAAACC | AGGTACATTT | CACATCACTT | TGGGATCCTG | GCAACTTTCT | 11820 |
| CTTTTGTTTT | TTTTTTTTT | TTGAGACAGG | GTCTCCTCTG | TCACCCAGGA | TGGAGTGCAG | 11880 |
| TGGTGTGATC | ATAGCTCACT | GCAGCCTCGA | ACTCCTCAAG | TGATCTTCCT | GCCTCAGCCT | 11940 |
| CCCAAGTAGC | GGGACCACAG | GCACACAGCA | CCATGCCCAT | CTAATTAAAA | AAATTTTTTT | 12000 |
| TTGTAGAGAC | AGGGGTCTCT | GTACATTTCC | CAGGCTGGTC | ATGTACTCCT | AAGCTCAAGC | 12060 |
| AGTCCTCCCA | CCTCAGCCTC | CCAAAGTGCC | GGAATTACAG | TCATGAGCCA | CCATTCCCAG | 12120 |
| CGCTGGTGAC | TTTCTCCATC | ACTGGTGACT | TTCTCCATCA | CTGGTATTCA | CTGCATTAGT | 12180 |
| GATGACATCA | TTACAATCTT | CAATATGCAA | CTTTGTAGTC | CTACTCTTGC | ATTCTTACTT | 12240 |
| TAAAGCCTCA | GCATTAAGTT | TGAATGTAAT | ATTACAGCAT | CCTTCATTAC | TTTAAATCAT | 12300 |
| TGGTTTCAAT | AGTAATTCAT | TTAAATCTAA | AATGTTAGGC | TGCAGTGGCT | CATGCCTGTA | 12360 |
| ATCCCCCCAG | TTGGGAGAC | TGAGGTGGGA | GAATCACTTG | AGGCCAAGAA | TTTGAGACCA | 12420 |

| | | | | | |
|---|---|---|---|---|---|
| GCCTGGGCAA | CACGGCAAGA | CCCCATCTCT | AAAAATTAGT | GGCCCGGCGC | CTGTGCCTCA | 12480 |
| CGCCTGTAAT | CCCAACACTT | TGGGAGGCCG | AGGCGGATAG | CTTGAGGTCA | GGAGTTCAAG | 12540 |
| ATCAGCCTGG | CCAACATGGC | GGAAACCCAT | TTCTACTAAA | AATACAAAAA | TTAGCTGGGC | 12600 |
| ATGGTGGCAC | GCCTGTAATC | CCAGCTATTG | AGAGGCCGAG | GCAGGCAGAC | TGGGAGGCCA | 12660 |
| AGGCAGGCAG | ATTGCTTTGA | GACCTGCCTG | GGTAACATGG | AGAAATCCTG | TCTCTACAGA | 12720 |
| AAAATACAAA | AATTAGCCAA | GCATGGAGAA | ACCTCGTCTC | TATAGAAAGA | CACAAAAACT | 12780 |
| AGCCATGCAT | GCCTGTGGTC | CAGCTACTCG | AAAGGCTGAG | ATGGGAGGAT | TGCTTGATCC | 12840 |
| TGAGAGGTCA | AGGCTGAAGT | GAGCCATGGT | GTGGCACTGC | ACTCCAGCCA | GGGTGACAGA | 12900 |
| CTAAAACCTT | GTCTCAAAAT | AAATAAACAC | ATTTAAAATA | AATAAATACA | ATTAAAACTA | 12960 |
| AAATTAAAAA | ATAAAATAAA | ATGTTAAGAG | AATAGCTCAA | ATTCTCCAAA | AGAACTCTTG | 13020 |
| CACACCATTC | CTCCTCTTCT | CAAATCTCTA | TTTTCCTTCC | CCAAAGCCAG | TAACTGCTTC | 13080 |
| TCACCCTGAC | CCTGTGCTTT | CTTTCCCGTC | ATTGCGAAAG | AATGGTCCTT | GCTTCTGTGC | 13140 |
| TGATCCCAAA | CCCTTTTGCC | CTCAGATCCT | CCTGTCCTTC | CCTGGCCCTG | CTCTGTATTG | 13200 |
| GCTGTGGGGT | GGGGGTGGCG | GTGGAACTGA | CCCCTGGGGT | CTGCATTTCT | CAGGCTCCCA | 13260 |
| GGGCTGTGGC | TGACTTTGGC | CAATGGGAGG | CAAGGACGGG | AGACTGAGAG | CTTGGGAGGA | 13320 |
| AGGGAGAGAG | GTATGTTTCT | TCTCCTTACT | CCCTGCCTGG | GGTGGCACCT | TGGGCAGGAC | 13380 |
| TCTGTTTTGC | CCATGGCCTC | AGCTCCCACC | AGATGCCTCT | AGTCCCTGGG | CTCAGGAAAT | 13440 |
| AGACAACCTC | CTTCCACTAT | CGCTGTAGCC | CAAGGAGGGA | AGTATTTTTT | TTCTTTCTTT | 13500 |
| CTTTCTTTCC | TTTTTTTTTT | TTACAGAGTC | TCACTCTTGT | TGCCCAGGCT | GGAGTGCAGT | 13560 |
| GGTGCGATCT | CAGCTCACTG | CCACCTCTGC | CTCCCGGGTT | CAAGTGATTC | TCCTGCCTCA | 13620 |
| GCCTCCAGGG | TGTGCCACTA | TGCCCAGCTA | ATTTTGTAT | TTTGGTAGA | GACGGGGTTT | 13680 |
| TGCCATGTTG | ACCAGGCTGG | TCTTGAACTT | CTGACCCCAA | ATGATCTGCC | TGCCTCGTCC | 13740 |
| TCCCAAAGTG | CTGGGATTAC | AGGCATGAGC | CACTGTGCCT | GGCCGAAGGA | AATATTTTCT | 13800 |
| TGCTATTGCT | AATCTCTGGG | TTACCTCGCT | ATCCCCATT | TAGCTTCACT | TCTCCTCCAT | 13860 |
| CACCTGTATG | AGGAATTCCC | TCTGTGTTAA | ATATCTGGAG | AAGTTTCCTG | ATTGGACCCT | 13920 |
| GGCTGTTGCA | GCTTCCAAGG | CCACCTCTCT | TTGTGGCTGG | TATCCTTTTC | CCATGCATCT | 13980 |
| TCTCCAGGAC | TTCCATTCTG | CAGTTATCTC | TCTGAACTCA | GTGTCTTCTT | CCCATCAGTA | 14040 |
| TAGGGGTGGA | CTTTAGTATC | TCCTATGTTT | AGGCAACATC | TCTCCTTTGA | CTCTGCGTCT | 14100 |
| TCTCCAGTGG | TTGCCCTTCT | CTGCTCCTCT | TCACAATAAC | ACCTCCTGAA | AGGGCCACCC | 14160 |
| ATGCCTGCCC | CCTCCTTTCC | TCACCCCCTC | TGTGGCTGGA | CTTCTGTTCC | TACACTCCAC | 14220 |
| CCTGGTTGAC | AAAGTCACTG | ATTACTTCTC | TATTTCAGC | TTACTTGATC | CTTAATTGCC | 14280 |
| TTCAAAAACA | GCTAACTGGG | CCATGCATGT | AATCCCAGCA | CTTCGGGAGG | CCAAGGCAGG | 14340 |
| AGGATCACTT | GAGCCCAGGA | GTTCAGGACC | AGCCTGCCTG | GCAACATAG | TGAGACCCTA | 14400 |
| TCTACAAAAA | ATAGAAAAAT | TAGCCGGGCG | TTGTGACTCA | TGCTTGTGGT | CCCAGCTACA | 14460 |
| AAGGAAGCTG | AGGTGGGAGG | ATGGCTTGAG | TCCGGGAGGG | TGAGGCTGCA | GTGAGCCATG | 14520 |
| ATCACGCCAC | TGCACTCCAG | CCTGCACAAC | AGAAGGAGGC | CCTTTCTGTA | AAAAAAAAA | 14580 |
| TGGTTGACCA | CTCCTTCCTT | GAAATGCTTT | TTCTTGAGG | CTTCCATGCC | CTGCCTTATC | 14640 |
| CTGTTTCTTC | CTACTTCTCT | GGTTGTGCTT | TTTCCTCTGC | TCAGTATTTA | ACATGTTGGT | 14700 |
| GTGACCCTGG | CTCTGGCCTG | GGCCCCCTTC | TCTATCTACG | TGCTTTCTCT | CGACGACCTC | 14760 |
| CATCGGTTGC | ATGGGTTTAA | CTACCAAATC | TGTGATTCTA | GCTCCGACAC | CCCAGGCTAA | 14820 |
| AGTAGCCACC | TGGTCACTCC | CTATTACATT | GGTCAATTTC | ATTTCTCTGT | GCCACCTATG | 14880 |

| | | | | | | |
|---|---|---|---|---|---|---|
| ATTTTCCTGA | TTTATTTATT | CACTTTTCAT | TGTCTGTCTT | CCCCACTAAA | ATAAAAACTT | 14940 |
| CTTGAGAAGG | GGCTTCATCG | ATCTGCCTCT | GTTCTATCCC | AGGCCCTCAA | ACAAGGACC | 15000 |
| AGATATTCAA | CAAATATTTA | TTGAATGCGT | ACATGAATTA | AAACTCTAAT | TGGTTGTATG | 15060 |
| CTGGTGGTTT | ATTATTTTCA | TGGAGGAAAT | GACTTGTAGG | CTGTGACACT | CAGCTTTTGT | 15120 |
| CTCTGATGCT | TTGTTGCCCT | GTTCTGTCAC | CGAGGGCTGT | CGTCATTGCT | CTGGCCATTT | 15180 |
| TGTGCTCTTT | GAATTTCTAA | TCATCACACT | CAACCCAGAA | GGCAGCCTTA | CCTTTCAGCA | 15240 |
| CTCTTCAGCT | GAATGAGTGC | AAGTTGGAGG | CAGGGTCATT | TTTTGATAGG | AAATTGAATG | 15300 |
| TTTATATGCT | GGTAAATATA | AAGCTTAGCT | TTTTACAAAG | AATTTCTCAA | AAGTGAGCTT | 15360 |
| TGTTGAAGCC | CTGTAAATTG | TTAGAACTTT | TATGGAAATT | TTAATTTAGG | AAAAAATGTC | 15420 |
| ATCTGTTTGG | GCTGACTTAG | TTGTTAGTTG | TTTGTCCTTT | CTTTTTTTTG | GTGGAGGGTA | 15480 |
| TGGAGTTTTG | CTCTTGTAAC | CCAGGCTGGA | GTGCAGTGGC | GCGATCTCGG | CTCACTGCAA | 15540 |
| CCTCCGCCTC | CTGGGTTCAA | GCGATTCTCT | CACCTCAGCC | TCCGAGTAG | CTGGGATTAC | 15600 |
| AGGCATGCAC | CACCACACTT | GGCTAATTTT | TGTATTTTAA | GTAGAGACCG | GGTTTCACTA | 15660 |
| TGTTGGTCAG | GCTGGTTTCG | AACTCCTGAC | CTCAAGTGAT | CACCCACCTT | GGCCTCCCAA | 15720 |
| AGTGCTTGGA | TTACAGACAT | GAGCCACCAC | ACCCGGCCAA | GAGGACTTCT | TTTAAAAATG | 15780 |
| ATTTCTTGGG | CCGGGTGCAG | TGGCTCACAC | CTGTAATCCC | AGCACTTTGG | GAGGCTGAGG | 15840 |
| TGGGTGGTTC | ACAAGGTCAG | GAGTTTGAGA | TCAGCCTGGC | CAATATGGTG | AAACTCCATC | 15900 |
| TCTACTAAAA | ATACAAAAAT | TAGCCAGGCA | TGGTGGCGCA | CCCCTGTTGT | CCCAGCTACT | 15960 |
| CGGGAGGCTG | AGGCAGGAGA | ATCACTTGAA | CCTGGGAGGT | GGAGGTTGCA | GTGAGCCGAG | 16020 |
| ATGGCACCAC | TGCACTCCAG | CCTGGGCAAC | AGAGCAAGAC | TCTGCCTCCA | AAAATAAAAA | 16080 |
| TTAAAATGAT | TTCTTAAGTA | AATTTCAAAT | ATAGAATGTA | TATGCTAGTG | ATAACAAAAT | 16140 |
| TAACACTGTT | TATGCAAGTC | TGCAATAGGT | AGATGTGAAG | TTGATAGGTG | CAATAAGTAT | 16200 |
| AGGCAAACAC | ATAGGAACAT | TTGACCTGTT | TTTTGTTGA | TTTTAAAACA | TTGAATAATT | 16260 |
| GGGAAGCTTT | TAAATCTCTT | AATTTGAGCA | ACTAGATGGC | TGTATTTATC | TCCTTATATT | 16320 |
| AAAAAAACTA | TTATAATTAT | CTTTCCACA | TATCAAACTC | CACTGGTTTT | TTTCCCATTT | 16380 |
| TTCTTTCATA | CTTCAGAAAG | ACGAGAATCC | AGGACTTGAA | TCGTATCTTC | CCACTTTCTG | 16440 |
| AGGACTACTC | TGGATCAGGC | TTCGGCTCCG | GCTCCGGCTC | TGGATCAGGA | TCTGGGAGTG | 16500 |
| GCTTCCTAAC | GGAAATGGAA | CAGGATTACC | AACTAGTAGA | CGAAAGTGAT | GCTTTCCATG | 16560 |
| ACAACCTTAG | GTCTCTTGAC | AGGAATCTGC | CCTCAGACAG | CCAGGACTTG | GGTCAACATG | 16620 |
| GATTAGAAGA | GGATTTTATG | TTATAAAAGA | GGATTTCCC | ACCTTGACAC | CAGGCAATGT | 16680 |
| AGTTAGCATA | TTTTATGTAC | CATGGTTATA | TGATTAATCT | TGGGACAAAG | AATTTTATAG | 16740 |
| AAATTTTTAA | ACATCTGAAA | AAGAAGCTTA | AGTTTTATCA | TCCTTTTTTT | TCTCATGAAT | 16800 |
| TCTTAAAGGA | TTATGCTTTA | ATGCTGTTAT | CTATCTTATT | GTTCTTGAAA | ATACCTGCAT | 16860 |
| TTTTTGGTAT | CATGTTCAAC | CAACATCATT | ATGAAATTAA | TTAGATTCCC | ATGGCCATAA | 16920 |
| AATGGCTTTA | AAGAATATAT | ATATATTTTT | AAAGTAGCTT | GAGAAGCAAA | TTGGCAGGTA | 16980 |
| ATATTTCATA | CCTAAATTAA | GACTCTGACT | TGGATTGTGA | ATTATAATGA | TATGCCCCTT | 17040 |
| TTCTTATAAA | AACAAAAAAA | AAATAATGAA | ACACAGTGAA | TTTGTAGAGT | GGGGGTATTT | 17100 |
| GACATATTTT | ACAGGGTGGA | GTGTACTATA | TACTATTACC | TTTGAATGTG | TTTGCAGAGC | 17160 |
| TAGTGGATGT | GTTTGTCTAC | AAGTATGATT | GCTGTTACAT | AACACCCCAA | ATTAACTCCC | 17220 |
| AAATTAAAAC | ACAGTTGTGC | TGTCAATACC | TCATACTGCT | TTACCTTTTT | TTCCTGGATA | 17280 |
| TCTGTGTATT | TTCAAATGTT | ACTATATATT | AAAGCAGAAA | TATAACC | | 17327 |

(2) INFORMATION FOR SEQ ID NO:16:

(i) SEQUENCE CHARACTERISTICS:
(A) LENGTH: 38 base pairs
(B) TYPE: nucleic acid
(C) STRANDEDNESS: both
(D) TOPOLOGY: linear (ii) MOLECULE TYPE: DNA (xi) SEQUENCE DESCRIPTION: SEQ ID NO:16:

TCTGGGTGTT GATGTGGATC TCTTTCTATT TGTTCAGG     38

(2) INFORMATION FOR SEQ ID NO:17:

(i) SEQUENCE CHARACTERISTICS:
(A) LENGTH: 21 base pairs
(B) TYPE: nucleic acid
(C) STRANDEDNESS: both
(D) TOPOLOGY: linear (ii) MOLECULE TYPE: DNA (xi) SEQUENCE DESCRIPTION: SEQ ID NO:17:

GAACCTCTTT CTAAAGGGA C     21

(2) INFORMATION FOR SEQ ID NO:18:

(i) SEQUENCE CHARACTERISTICS:
(A) LENGTH: 61 base pairs
(B) TYPE: nucleic acid
(C) STRANDEDNESS: both
(D) TOPOLOGY: linear (ii) MOLECULE TYPE: DNA (xi) SEQUENCE DESCRIPTION: SEQ ID NO:18:

TGCAAATGAC AGATGGCAGA GCTTTTGGA AAAAGAAAAA ATAATAACCA CACAGCAAAC     60
G     61